(12) United States Patent
Viitanen et al.

(10) Patent No.: US 7,135,326 B2
(45) Date of Patent: Nov. 14, 2006

(54) UDP-GLUCOSYLTRANSFERASES

(75) Inventors: Paul V. Viitanen, West Chester, PA (US); Knut Meyer, Wilmington, DE (US); Drew E. Van Dyk, Wilmingtion, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 509 days.

(21) Appl. No.: 10/359,369

(22) Filed: Feb. 6, 2003

(65) Prior Publication Data
US 2003/0215927 A1 Nov. 20, 2003

Related U.S. Application Data

(60) Provisional application No. 60/355,511, filed on Feb. 7, 2002.

(51) Int. Cl.
*C12N 1/22* (2006.01)
*C07H 21/04* (2006.01)
*C12P 21/06* (2006.01)

(52) U.S. Cl. .......................... 435/252.1; 435/4; 435/6; 435/69.1; 435/183; 435/193; 435/320.1; 536/23.2; 536/23.4; 536/23.5; 536/23.7; 530/350

(58) Field of Classification Search .................. 435/4, 435/6, 69.1, 183, 192, 193, 252–3, 320.1, 435/325, 410; 536/23.2, 23.4, 23.5, 23.6, 536/23.7; 800/295
See application file for complete search history.

(56) References Cited

U.S. PATENT DOCUMENTS

2002/0106769 A1* 8/2002 Omura et al. ................ 435/193

OTHER PUBLICATIONS

GenBank Accession No. AA171187 NORQ, Jan. 22, 2002.*
GenBank Accession No. AA171192, NORQ, Jan. 22, 2002.*
Kita et al. FEBS Lett. 2000, vol. 469(2-3), 173-178.*
Gen Bank Accession No. AB033758, Kita et al. Mar. 31, 2000.*
Sandermann,; Higher plant metabolism of xenobiotics: the green liver concept; Pharmacogenetics (4) :225-241 (1994).
Coleman; Detoxification of xenobiotics by plants: chemical modification and vacuolar compartmentation Trends Plant Sci. Detoxification vol. 2: No. 4 p. 144-151 (1997).
Meech and Mackenzie; Structure and function of Uridine Diphosphate Glucuronosyltransferases, Clinical and Experimental Pharmacology and Physiology 24:907-915 (1997).
Mackenzie et al.; The UDP glycosyltansferase gene superfamily: recommended nomenclature update based on evolutionary divergence Pharmacogenetics 7:255-269 (1997).
Lim et al.; Identification of Glucosyltransferase Genes Involved in Sinapate Metabolism and Lignin Synthesis in Arabidopsis J. Biol. Chem. vol. 276 No. 6:4344-4349 (2001).
Jackson et al., Identification and Biochemical Characterization of an Arabidopsis Indole-3-acetic Acid Glucosyltransferase J Biol. Chem. vo. 267 No. 6:4350-4356 (2001).

Ford et al., Cloning and Characterization of Vitis vinifera UDP-Glucose: Flavonoid 3-O—Glucosyltransferase, a Homologue of the Enzyme Encoded by the Maise Bronze-1 Locus that may Primarily Serve to Glucosylate Anthocyanidins in Vivo J Biol. Chem. 273:9224-9233 (1998).
Lee and Raskin, Purification, Cloning, and Expression of a Pathogen Inducible UDP-glucose:Salicylic Acid Glucosyltransferase from Tabacco J. Biol. Chem. vol. 274 No. 51:36637-36642 (1999).
Siebert et al.; Cloning of the genes coding for chorismate pyruvatelyase and 4-hydroxybenzoate octaprenyl transferase from *Escherichia coli*, Lett vol. 307 (3):347-350 (1992).
Wink, M.; Compartmentation of Secondary Metabolites and Xenobiotics in Plant Vacuoles vol. 25 pp. 142-169 In the Plant Vacuole: Advances in Botanical Research (1997).
Callow, J.A. et al.;Advances in Botanical Research incorporating Advances in Plant Pathology Eds.; Academic Press: London, New York.; vol. 25, pp. 141-169 (1997).
Siebert et al.; Genetic Engineering of Plant Secondary Metabolism,Plant Physiol. 112: 811-819 (1996).
Li et al.; An acyltransferase catalyzing the formation of diacylglucose is a serine caroxypeptidase-like protein, Proc. Natl. Acad. U.S. A. vol. 97, No. 12:6902-6907 (2000).
Klick et al.;Glucosides and Glucose Esters of Hydroxybenzoic Acids in Plants, Phytochemistry vol. 27 (7):2177-2180 (1988).
Gross et al.; Partial Purification and Properties of UDP-Glucose: Vanillate 1-0-Glucosyl Transferase from Oak Leaves, Phytochemisrty vol. 22 No. 10:2179-2182 (1983).
Bechthold et al.;Partial Purification, Properties, and Kinetic Studies of UDP-Glucose:p-Hydroxybenzoate Glucosyltransferase from Cell Cultures of Lithospermum erythrohizon Archives of Biochemistry and Biophysics vol. 288(1):39-47 (1991).
Li et al.; Purification of UDP-Glucose: 4-Hydroxybensoate Glucosyltransferase from Cell Cultures of Lithospermum Erthrorhizon, Phytochemistry vol. 46 (1):27-32 (1997).
Mayer et al.;Rerouting the Plant Phenylpropaniod Pathway by Expression of a Novel Bacterial Enoyl-CoA Hydratase/Lyase Enzyme Function, Plant Cell vol. 13:1669-1682 (2001).
Li et al.; Metabolization of the Artificial Secondary Metabolite 4-Hydroxybenzoate in ubiC-Transformed Tobacco, (Plant Cell Physiol. 38(7):844-850 (1997).
Fraissinet-Tachet et al.; Two Tobacco genes induced by infection, elicitor and salicylic acid encode glucosultransferases acting on phenylpropanoids and benzoic acid derivatives, including salicylic acid, (FEBS lett. 437(3):319-323 (1998).
Lim et al.; The Activity of Arabidopsis Glycosyltransferases toward Salicylic Acid, 4-Hydroxybenzoic Acid, and Other Benzoates, J. Biol. Chem. vol. 277(1):586-592 (2002).

(Continued)

*Primary Examiner*—Manjunath N. Rao

(57) ABSTRACT

This invention pertains to nucleic acid fragments encoding plant glucosyltransferases, heretofore undescribed, that exhibit catalytic activity with p-hydroxybenzoic acid (pHBA) as a substrate and only attach glucose to the aromatic carboxyl group of pHBA, to form the pHBA glucose ester. These enzymes have potential applications both in vitro and in vivo, and their primary amino acid sequences can be used to identify other proteins that have similar kinetic properties.

11 Claims, 4 Drawing Sheets

OTHER PUBLICATIONS

Milkowski et al.; Cloning and heterologous expression of a rape cDNA encoding UDP-glucose:sinapate glucosyltransferase, Planta 211 (6):883-886 (2000).

Milkowski et al.;Correspondence Identification of four Aragidopsis genes encoding hydroxycinnamate glucosyltransferases, FEBS Lett. 486 (2):183-184 (2000).

Vogt et al.; Cloning and expression of a cDNA encoding betanidin 5-O-glucosyltransferases, a betanidin-and flavonoid-specific enzyme with high homology to inducible glucosyltransferases from the Solanaceae, Plant J. 19(5):509-519 (1999).

Lehfeldt et al.; Cloning of the SNGL Gene of Arabidopsis Reveals a Role for a Serine Carboxypeptidase-like Protein as an Acyltransferase in Secondary Metabolism, Plant Cell 12.(8):1295-1306 (2000).

Nichols et al.; Cloning and Sequencing of *Escherichia coli* ubiC and Purification of Chorismate Lyase, J. Bacteriol. vol. 174 No. 16 :5309-5316 (1992).

Mukeim and Learch; Towards a high-yield bioconversion of ferulic acid to vanillin, App. Microbiol. Biotechnol. 51:456-461 (1999).

Kita et al.; Molecular cloning and characterization of a novel gene encoding limonoid UDP-glucosyltransferase in Citrus1, FEBS Lett. 469:173-178 (2000).

Sugita et al.; Genomic organization, sequence analysis and expression of all five genes encoding the small subunit of ribulose-1,5-bisphosphate carboxylase/oxygenase from tomato, Mol Gen Genet. 209:247:256 (1987).

Sommer et al.;Expression of Baterial Chorismate Pyruvate-Lyase in Tobacco: Evidence for the Presence of Chorismate in the Plant Cytoso, Plant Cell Physiol. 39 (11): 1240-1244 (1998).

Sommer et al.; Specific induction of secondary product formation in transgenic plant cell cultures using an inducible promoter, Plant Cell Reports 17:891-896 (1998).

Holden et al.; Chorismate lyase: kinetics and engineering for stability, Biochimica et Biophysica Acta 1594:160-167 (2002).

S. Kobayashi et al., Myb-related genes of the Kyoho grape (*V. labruscana*) regulate anthocyanin biosynthesis, Planta, Oct. 2002, vol. 215:924-933.

T. Endo et al., Modification of limonoid metabolism in suspension cell culture of citrus, Plant Biotechnology, 2002, vol. 19(5):397-403.

C. A. McIntosh et al., Biosynthesis of naringin in Citrus paradasi:UDP-glucosyltransferase activity in grapefruit seedlings, Phytochemistry, 1999, vol. 29(5):1533-1538.

\* cited by examiner

```
                         SEQUENCE LISTING

<160> NUMBER OF SEQ ID NOS: 46

<210> SEQ ID NO 1
<211> LENGTH: 35
<212> TYPE: DNA
<213> ORGANISM: artificial sequence
<220> FEATURE:
<223> OTHER INFORMATION: Primer 1

<400> SEQUENCE: 1
ctactcattt catatggaac tatcatcttc tcctt                            35

<210> SEQ ID NO 2
<211> LENGTH: 40
<212> TYPE: DNA
<213> ORGANISM: artificial sequence
<220> FEATURE:
<223> OTHER INFORMATION: Primer 2

<400> SEQUENCE: 2
catcttactg gatccttatg acttttgcaa taaaagtttt                       40

<210> SEQ ID NO 3
<211> LENGTH: 1494
<212> TYPE: DNA
<213> ORGANISM: Brassica napus
<220> FEATURE:
<221> NAME/KEY: CDS
<222> LOCATION: (1)..(1494)

<400> SEQUENCE: 3 atg gaa cta tca tct tct cct tta cct cct cat gtt atg ctt tta tcg      48
Met Glu Leu Ser Ser Ser Pro Leu Pro Pro His Val Met Leu Leu Ser
1               5                  10                  15 ttc cca ggg caa ggc cat gtt aat cca ctt ctt cgt ctc ggc aag ctc      96
Phe Pro Gly Gln Gly His Val Asn Pro Leu Leu Arg Leu Gly Lys Leu
            20                  25                  30 ttg gct tcg aag ggt tta ctc gtc act ttt gtc acc aca gaa tca tgg    144
Leu Ala Ser Lys Gly Leu Leu Val Thr Phe Val Thr Thr Glu Ser Trp
        35                  40                  45 ggc aaa aag atg cga acc gcc aac aag att caa gac cga gcc ctc aaa    192
Gly Lys Lys Met Arg Thr Ala Asn Lys Ile Gln Asp Arg Ala Leu Lys
    50                  55                  60 cct atc ggt aaa ggt tat ctc cgg ttc gat ttc ttc gac gac ggt ctc    240
Pro Ile Gly Lys Gly Tyr Leu Arg Phe Asp Phe Phe Asp Asp Gly Leu
65                  70                  75                  80 cct gaa gac gac gat gca agc aga acc aac tta acc atc ctc cga cca    288
Pro Glu Asp Asp Asp Ala Ser Arg Thr Asn Leu Thr Ile Leu Arg Pro
                85                  90                  95 caa cta gag ctg gtc gga caa caa gag atc aaa aac ctg gtg aaa cgt    336
Gln Leu Glu Leu Val Gly Gln Gln Glu Ile Lys Asn Leu Val Lys Arg
            100                 105                 110 tac aag gaa gtg atg aaa cag ccc gtg acg tgt ctc atc aac aac cct    384
Tyr Lys Glu Val Met Lys Gln Pro Val Thr Cys Leu Ile Asn Asn Pro
        115                 120                 125 ttc gtc tct tgg gtc tgt gac gta gcc gaa gat ctt caa atc ccc tgt    432
Phe Val Ser Trp Val Cys Asp Val Ala Glu Asp Leu Gln Ile Pro Cys
    130                 135                 140
```

```
gct gtt ctc tgg gtc cag tct tgt gct tgc cta gct tct tat tat tat          480
Ala Val Leu Trp Val Gln Ser Cys Ala Cys Leu Ala Ser Tyr Tyr Tyr
145                 150                 155                 160 tac cac cac aag ctt gtc gac ttc ccg act gaa aca gat ccc aag atc          528
Tyr His His Lys Leu Val Asp Phe Pro Thr Glu Thr Asp Pro Lys Ile
                165                 170                 175 gat gtc cag atc cca tgc atg cct gtc ttg aaa cac gac gag atc cct          576
Asp Val Gln Ile Pro Cys Met Pro Val Leu Lys His Asp Glu Ile Pro
            180                 185                 190 tct ttc att cat cct ttt tca cct tat tcg ggt tta aga gaa gtg atc          624
Ser Phe Ile His Pro Phe Ser Pro Tyr Ser Gly Leu Arg Glu Val Ile
        195                 200                 205 att gat cag atc aaa cgt ctc cac aag cct ttc gtt gtt ctc atc gat          672
Ile Asp Gln Ile Lys Arg Leu His Lys Pro Phe Val Val Leu Ile Asp
    210                 215                 220 act ttc tac tcc ttg gag aaa gat atc atc gac cac atg aca aac ctc          720
Thr Phe Tyr Ser Leu Glu Lys Asp Ile Ile Asp His Met Thr Asn Leu
225                 230                 235                 240 tct cgc acc ggc gtt gtc aga ccg ctc gga ccg ctt tac aaa atg gcc          768
Ser Arg Thr Gly Val Val Arg Pro Leu Gly Pro Leu Tyr Lys Met Ala
                245                 250                 255 aaa acg ttg att tgt gat gac atc aaa gga gat atg tct gag acg agg          816
Lys Thr Leu Ile Cys Asp Asp Ile Lys Gly Asp Met Ser Glu Thr Arg
                260                 265                 270 gat gac tgc atg gag tgg tta gac tcg cag cct gtt tcc tcc gtt gtt          864
Asp Asp Cys Met Glu Trp Leu Asp Ser Gln Pro Val Ser Ser Val Val
            275                 280                 285 tac atc tca ttt ggt acc atg gct tac gtg aca caa gaa cag atc agc          912
Tyr Ile Ser Phe Gly Thr Met Ala Tyr Val Thr Gln Glu Gln Ile Ser
        290                 295                 300 gag att gcg ttt ggc gtt tta aac gct ggc gtt tcg ttt ttg tgg gtg          960
Glu Ile Ala Phe Gly Val Leu Asn Ala Gly Val Ser Phe Leu Trp Val
305                 310                 315                 320 ata aga caa caa gaa tta ggt gta aac aaa gag cga cat gtt ttg cct         1008
Ile Arg Gln Gln Glu Leu Gly Val Asn Lys Glu Arg His Val Leu Pro
                325                 330                 335 gaa gaa ctc aaa ggg aaa ggt aaa gtc gtt gaa tgg tgt tca caa gag         1056
Glu Glu Leu Lys Gly Lys Gly Lys Val Val Glu Trp Cys Ser Gln Glu
                340                 345                 350 aaa gtc ttg gct cat cct tct gtg gtt tgt ttc gtg act cat tgt gga         1104
Lys Val Leu Ala His Pro Ser Val Val Cys Phe Val Thr His Cys Gly
            355                 360                 365 tgg aac tca acg atg gaa gct ttg tct agt gga gtc cca acg gtc tgt         1152
Trp Asn Ser Thr Met Glu Ala Leu Ser Ser Gly Val Pro Thr Val Cys
370                 375                 380 ttt cct cag tgg gga gat caa gtc acc gac gct gct tac atg agc gac         1200
Phe Pro Gln Trp Gly Asp Gln Val Thr Asp Ala Ala Tyr Met Ser Asp
385                 390                 395                 400 gtg ttc aag acg gga gtg agg ctt agc cgt gga gag acg gag gag aga         1248
Val Phe Lys Thr Gly Val Arg Leu Ser Arg Gly Glu Thr Glu Glu Arg
                405                 410                 415 gtg gtg cct agg gag gaa gta gcg gag agg ctg aga gaa gtt acg aaa         1296
Val Val Pro Arg Glu Glu Val Ala Glu Arg Leu Arg Glu Val Thr Lys
            420                 425                 430 gga gag aaa gcg acg gag ctg aag aag aat gct tta aaa tgg aag gag         1344
Gly Glu Lys Ala Thr Glu Leu Lys Lys Asn Ala Leu Lys Trp Lys Glu
        435                 440                 445 gag gcg gaa gcg gcc gtg gct cgc cgt ggc tcg tcg gat cgg aat ctt         1392
Glu Ala Glu Ala Ala Val Ala Arg Arg Gly Ser Ser Asp Arg Asn Leu
```

```
                  450                 455                 460
gat gag ttt gtg gaa aag ttg tgc gtc aaa cat gtg gct aaa cag aac    1440
Asp Glu Phe Val Glu Lys Leu Cys Val Lys His Val Ala Lys Gln Asn
465                 470                 475                 480 gga agt ctc aat caa aac gga agt att caa aaa ctt tta ttg caa aag    1488
Gly Ser Leu Asn Gln Asn Gly Ser Ile Gln Lys Leu Leu Leu Gln Lys
                485                 490                 495 tca taa                                                            1494
Ser

<210> SEQ ID NO 4
<211> LENGTH: 497
<212> TYPE: PRT
<213> ORGANISM: Brassica napus

<400> SEQUENCE: 4
```

| Met | Glu | Leu | Ser | Ser | Pro | Leu | Pro | His | Val | Met | Leu | Leu | Ser |
|-----|-----|-----|-----|-----|-----|-----|-----|-----|-----|-----|-----|-----|-----|
| 1   |     |     |     | 5   |     |     |     |     | 10  |     |     |     | 15  |

Phe Pro Gly Gln Gly His Val Asn Pro Leu Leu Arg Leu Gly Lys Leu
                20                  25                  30

Leu Ala Ser Lys Gly Leu Leu Val Thr Phe Val Thr Thr Glu Ser Trp
            35                  40                  45

Gly Lys Lys Met Arg Thr Ala Asn Lys Ile Gln Asp Arg Ala Leu Lys
50                  55                  60

Pro Ile Gly Lys Gly Tyr Leu Arg Phe Asp Phe Phe Asp Asp Gly Leu
65                  70                  75                  80

Pro Glu Asp Asp Asp Ala Ser Arg Thr Asn Leu Thr Ile Leu Arg Pro
                85                  90                  95

Gln Leu Glu Leu Val Gly Gln Gln Glu Ile Lys Asn Leu Val Lys Arg
            100                 105                 110

Tyr Lys Glu Val Met Lys Gln Pro Val Thr Cys Leu Ile Asn Asn Pro
        115                 120                 125

Phe Val Ser Trp Val Cys Asp Val Ala Glu Asp Leu Gln Ile Pro Cys
    130                 135                 140

Ala Val Leu Trp Val Gln Ser Cys Ala Cys Leu Ala Ser Tyr Tyr Tyr
145                 150                 155                 160

Tyr His His Lys Leu Val Asp Phe Pro Thr Glu Thr Asp Pro Lys Ile
                165                 170                 175

Asp Val Gln Ile Pro Cys Met Pro Val Leu Lys His Asp Glu Ile Pro
            180                 185                 190

Ser Phe Ile His Pro Phe Ser Pro Tyr Ser Gly Leu Arg Glu Val Ile
        195                 200                 205

Ile Asp Gln Ile Lys Arg Leu His Lys Pro Phe Val Val Leu Ile Asp
    210                 215                 220

Thr Phe Tyr Ser Leu Glu Lys Asp Ile Ile Asp His Met Thr Asn Leu
225                 230                 235                 240

Ser Arg Thr Gly Val Val Arg Pro Leu Gly Pro Leu Tyr Lys Met Ala
                245                 250                 255

Lys Thr Leu Ile Cys Asp Asp Ile Lys Gly Asp Met Ser Glu Thr Arg
            260                 265                 270

Asp Asp Cys Met Glu Trp Leu Asp Ser Gln Pro Val Ser Ser Val Val
        275                 280                 285

Tyr Ile Ser Phe Gly Thr Met Ala Tyr Val Thr Gln Glu Gln Ile Ser
    290                 295                 300

Glu Ile Ala Phe Gly Val Leu Asn Ala Gly Val Ser Phe Leu Trp Val

-continued

```
                    305                 310                 315                 320
        Ile Arg Gln Gln Glu Leu Gly Val Asn Lys Glu Arg His Val Leu Pro
                        325                 330                 335

Glu Glu Leu Lys Gly Lys Gly Lys Val Val Glu Trp Cys Ser Gln Glu
                    340                 345                 350

Lys Val Leu Ala His Pro Ser Val Cys Phe Val Thr His Cys Gly
                    355                 360                 365

Trp Asn Ser Thr Met Glu Ala Leu Ser Ser Gly Val Pro Thr Val Cys
                370                 375                 380

Phe Pro Gln Trp Gly Asp Gln Val Thr Asp Ala Ala Tyr Met Ser Asp
        385                 390                 395                 400

Val Phe Lys Thr Gly Val Arg Leu Ser Arg Gly Glu Thr Glu Arg
                        405                 410                 415

Val Val Pro Arg Glu Glu Val Ala Glu Arg Leu Arg Glu Val Thr Lys
                    420                 425                 430

Gly Glu Lys Ala Thr Glu Leu Lys Lys Asn Ala Leu Lys Trp Lys Glu
                    435                 440                 445

Glu Ala Glu Ala Ala Val Ala Arg Arg Gly Ser Ser Asp Arg Asn Leu
                450                 455                 460

Asp Glu Phe Val Glu Lys Leu Cys Val Lys His Val Ala Lys Gln Asn
        465                 470                 475                 480

Gly Ser Leu Asn Gln Asn Gly Ser Ile Gln Lys Leu Leu Leu Gln Lys
                        485                 490                 495

Ser

<210> SEQ ID NO 5
<211> LENGTH: 28
<212> TYPE: DNA
<213> ORGANISM: artificial sequence
<220> FEATURE:
<223> OTHER INFORMATION: Primer 3

<400> SEQUENCE: 5
ccatatcagt catgatgttc gaaacttg                                              28

<210> SEQ ID NO 6
<211> LENGTH: 24
<212> TYPE: DNA
<213> ORGANISM: artificial sequence
<220> FEATURE:
<223> OTHER INFORMATION: Primer 4

<400> SEQUENCE: 6
gtcaaagacg tcgacctagt atcc                                                  24

<210> SEQ ID NO 7
<211> LENGTH: 1455
<212> TYPE: DNA
<213> ORGANISM: Arabidopsis thaliana
<220> FEATURE:
<221> NAME/KEY: CDS
<222> LOCATION: (1)..(1455)

<400> SEQUENCE: 7 atg atg ttc gaa act tgt cca tct cca aac cca att cat gta atg ctc        48
Met Met Phe Glu Thr Cys Pro Ser Pro Asn Pro Ile His Val Met Leu
1               5                   10                  15 gtc tcg ttt caa gga caa ggc cac gtc aac cct ctt ctt cgt ctc ggc        96
Val Ser Phe Gln Gly Gln Gly His Val Asn Pro Leu Leu Arg Leu Gly
            20                  25                  30
```

-continued

| | |
|---|---|
| aag tta att gct tca aag ggt tta ctc gtt acc ttc gtt aca acg gag<br>Lys Leu Ile Ala Ser Lys Gly Leu Leu Val Thr Phe Val Thr Thr Glu<br>35                         40                     45 | 144 |
| ctt tgg ggc aag aaa atg aga caa gcc aac aaa atc gtt gac ggt gaa<br>Leu Trp Gly Lys Lys Met Arg Gln Ala Asn Lys Ile Val Asp Gly Glu<br>50                      55                   60 | 192 |
| ctt aaa ccg gtt ggt tcc ggt tca atc cgg ttt gag ttc ttt gat gaa<br>Leu Lys Pro Val Gly Ser Gly Ser Ile Arg Phe Glu Phe Phe Asp Glu<br>65                     70                 75               80 | 240 |
| gaa tgg gca gag gat gat gac cgg aga gct gat ttc tct ttg tac att<br>Glu Trp Ala Glu Asp Asp Asp Arg Arg Ala Asp Phe Ser Leu Tyr Ile<br>                  85                   90               95 | 288 |
| gct cac cta gag agc gtt ggg ata cga gaa gtg tct aag ctt gtg aga<br>Ala His Leu Glu Ser Val Gly Ile Arg Glu Val Ser Lys Leu Val Arg<br>            100                 105               110 | 336 |
| aga tac gag gaa gcg aac gag cct gtc tcg tgt ctt atc aat aac ccg<br>Arg Tyr Glu Glu Ala Asn Glu Pro Val Ser Cys Leu Ile Asn Asn Pro<br>          115                 120               125 | 384 |
| ttt atc cca tgg gtc tgc cac gtg gcg gaa gag ttc aac att cct tgt<br>Phe Ile Pro Trp Val Cys His Val Ala Glu Glu Phe Asn Ile Pro Cys<br>130                     135                   140 | 432 |
| gcg gtt ctc tgg gtt cag tct tgt gct tgt ttc tct gct tat tac cat<br>Ala Val Leu Trp Val Gln Ser Cys Ala Cys Phe Ser Ala Tyr Tyr His<br>145                   150                 155             160 | 480 |
| tac caa gat ggc tct gtt tca ttc cct acg gaa aca gag cct gag ctc<br>Tyr Gln Asp Gly Ser Val Ser Phe Pro Thr Glu Thr Glu Pro Glu Leu<br>                  165               170               175 | 528 |
| gat gtg aag ctt cct tgt gtt cct gtc ttg aag aac gac gag att cct<br>Asp Val Lys Leu Pro Cys Val Pro Val Leu Lys Asn Asp Glu Ile Pro<br>                180               185               190 | 576 |
| agc ttt ctc cat cct tct tct agg ttc acg ggt ttt cga caa gcg att<br>Ser Phe Leu His Pro Ser Ser Arg Phe Thr Gly Phe Arg Gln Ala Ile<br>                195               200               205 | 624 |
| ctt ggg caa ttc aag aat ctg agc aag tcc ttc tgt gtt cta atc gat<br>Leu Gly Gln Phe Lys Asn Leu Ser Lys Ser Phe Cys Val Leu Ile Asp<br>210                     215                   220 | 672 |
| tct ttt gac tca ttg gaa caa gaa gtt atc gat tac atg tca agt ctt<br>Ser Phe Asp Ser Leu Glu Gln Glu Val Ile Asp Tyr Met Ser Ser Leu<br>225                   230                 235               240 | 720 |
| tgt ccg gtt aaa acc gtt gga ccg ctt ttc aaa gtt gct agg aca gtt<br>Cys Pro Val Lys Thr Val Gly Pro Leu Phe Lys Val Ala Arg Thr Val<br>                  245               250               255 | 768 |
| act tct gac gta agc ggt gac att tgc aaa tca aca gat aaa tgc ctc<br>Thr Ser Asp Val Ser Gly Asp Ile Cys Lys Ser Thr Asp Lys Cys Leu<br>                260               265               270 | 816 |
| gag tgg tta gac tcg agg cct aaa tcg tca gtt gtc tac att tcg ttc<br>Glu Trp Leu Asp Ser Arg Pro Lys Ser Ser Val Val Tyr Ile Ser Phe<br>275                     280                   285 | 864 |
| ggg aca gtt gca tat ttg aag caa gaa cag atc gaa gag atc gct cac<br>Gly Thr Val Ala Tyr Leu Lys Gln Glu Gln Ile Glu Glu Ile Ala His<br>          290                 295               300 | 912 |
| gga gtt ttg aag tcg ggt tta tcg ttc ttg tgg gtg att aga cct cca<br>Gly Val Leu Lys Ser Gly Leu Ser Phe Leu Trp Val Ile Arg Pro Pro<br>305                   310                 315               320 | 960 |
| cca cac gat ctg aag gtc gag aca cat gtc ttg cct caa gaa ctt aaa<br>Pro His Asp Leu Lys Val Glu Thr His Val Leu Pro Gln Glu Leu Lys<br>                325               330               335 | 1008 |
| gag agt agt gct aaa ggt aaa ggg atg att gtg gat tgg tgc cca caa<br>Glu Ser Ser Ala Lys Gly Lys Gly Met Ile Val Asp Trp Cys Pro Gln | 1056 |

-continued

```
                340                 345                 350
gag caa gtc ttg tct cat cct tca gtg gca tgc ttc gtg act cat tgt      1104
Glu Gln Val Leu Ser His Pro Ser Val Ala Cys Phe Val Thr His Cys
        355                 360                 365 gga tgg aac tcg aca atg gaa tct ttg tct tca ggt gtt ccg gtg gtt      1152
Gly Trp Asn Ser Thr Met Glu Ser Leu Ser Ser Gly Val Pro Val Val
370                 375                 380 tgt tgt ccg caa tgg gga gat caa gtg act gat gca gtg tat ttg atc      1200
Cys Cys Pro Gln Trp Gly Asp Gln Val Thr Asp Ala Val Tyr Leu Ile
385                 390                 395                 400 gat gtt ttc aag acc ggg gtt aga cta ggc cgt gga gcg acc gag gag      1248
Asp Val Phe Lys Thr Gly Val Arg Leu Gly Arg Gly Ala Thr Glu Glu
                405                 410                 415 agg gta gtg cca agg gag gaa gtg gcg gag aag ctt ttg gaa gcg aca      1296
Arg Val Val Pro Arg Glu Glu Val Ala Glu Lys Leu Leu Glu Ala Thr
            420                 425                 430 gtt ggg gag aag gca gag gag ttg aga aag aac gct ttg aaa tgg aag      1344
Val Gly Glu Lys Ala Glu Glu Leu Arg Lys Asn Ala Leu Lys Trp Lys
        435                 440                 445 gcg gag gcg gaa gca gcg gtg gct cca gga ggt tcg tcg gat aag aat      1392
Ala Glu Ala Glu Ala Ala Val Ala Pro Gly Gly Ser Ser Asp Lys Asn
450                 455                 460 ttt agg gag ttt gtg gag aag tta ggt gcg gga gta acg aag act aaa      1440
Phe Arg Glu Phe Val Glu Lys Leu Gly Ala Gly Val Thr Lys Thr Lys
465                 470                 475                 480 gat aat gga tac tag                                                  1455
Asp Asn Gly Tyr
```

<210> SEQ ID NO 8
<211> LENGTH: 484
<212> TYPE: PRT
<213> ORGANISM: Arabidopsis thaliana

<400> SEQUENCE: 8

```
Met Met Phe Glu Thr Cys Pro Ser Pro Asn Pro Ile His Val Met Leu
1               5                   10                  15

Val Ser Phe Gln Gly Gln Gly His Val Asn Pro Leu Leu Arg Leu Gly
            20                  25                  30

Lys Leu Ile Ala Ser Lys Gly Leu Leu Val Thr Phe Val Thr Thr Glu
        35                  40                  45

Leu Trp Gly Lys Lys Met Arg Gln Ala Asn Lys Ile Val Asp Gly Glu
    50                  55                  60

Leu Lys Pro Val Gly Ser Gly Ser Ile Arg Phe Glu Phe Phe Asp Glu
65                  70                  75                  80

Glu Trp Ala Glu Asp Asp Arg Arg Ala Asp Phe Ser Leu Tyr Ile
                85                  90                  95

Ala His Leu Glu Ser Val Gly Ile Arg Glu Val Ser Lys Leu Val Arg
            100                 105                 110

Arg Tyr Glu Glu Ala Asn Glu Pro Val Ser Cys Leu Ile Asn Asn Pro
        115                 120                 125

Phe Ile Pro Trp Val Cys His Val Ala Glu Phe Asn Ile Pro Cys
    130                 135                 140

Ala Val Leu Trp Val Gln Ser Cys Ala Cys Phe Ser Ala Tyr Tyr His
145                 150                 155                 160

Tyr Gln Asp Gly Ser Val Ser Phe Pro Thr Glu Thr Glu Pro Glu Leu
                165                 170                 175

Asp Val Lys Leu Pro Cys Val Pro Val Leu Lys Asn Asp Glu Ile Pro
```

-continued

```
                    180                 185                 190
Ser Phe Leu His Pro Ser Ser Arg Phe Thr Gly Phe Arg Gln Ala Ile
            195                 200                 205

Leu Gly Gln Phe Lys Asn Leu Ser Lys Ser Phe Cys Val Leu Ile Asp
210                 215                 220

Ser Phe Asp Ser Leu Glu Gln Glu Val Ile Asp Tyr Met Ser Ser Leu
225                 230                 235                 240

Cys Pro Val Lys Thr Val Gly Pro Leu Phe Lys Val Ala Arg Thr Val
                245                 250                 255

Thr Ser Asp Val Ser Gly Asp Ile Cys Lys Ser Thr Asp Lys Cys Leu
                260                 265                 270

Glu Trp Leu Asp Ser Arg Pro Lys Ser Ser Val Val Tyr Ile Ser Phe
            275                 280                 285

Gly Thr Val Ala Tyr Leu Lys Gln Glu Gln Ile Glu Glu Ile Ala His
            290                 295                 300

Gly Val Leu Lys Ser Gly Leu Ser Phe Leu Trp Val Ile Arg Pro Pro
305                 310                 315                 320

Pro His Asp Leu Lys Val Glu Thr His Val Leu Pro Gln Glu Leu Lys
                325                 330                 335

Glu Ser Ser Ala Lys Gly Lys Gly Met Ile Val Asp Trp Cys Pro Gln
                340                 345                 350

Glu Gln Val Leu Ser His Pro Ser Val Ala Cys Phe Val Thr His Cys
            355                 360                 365

Gly Trp Asn Ser Thr Met Glu Ser Leu Ser Ser Gly Val Pro Val Val
            370                 375                 380

Cys Cys Pro Gln Trp Gly Asp Gln Val Thr Asp Ala Val Tyr Leu Ile
385                 390                 395                 400

Asp Val Phe Lys Thr Gly Val Arg Leu Gly Arg Gly Ala Thr Glu Glu
                405                 410                 415

Arg Val Val Pro Arg Glu Val Ala Glu Lys Leu Leu Glu Ala Thr
                420                 425                 430

Val Gly Glu Lys Ala Glu Glu Leu Arg Lys Asn Ala Leu Lys Trp Lys
            435                 440                 445

Ala Glu Ala Glu Ala Val Ala Pro Gly Gly Ser Ser Asp Lys Asn
450                 455                 460

Phe Arg Glu Phe Val Glu Lys Leu Gly Ala Gly Val Thr Lys Thr Lys
465                 470                 475                 480

Asp Asn Gly Tyr
```

<210> SEQ ID NO 9
<211> LENGTH: 27
<212> TYPE: DNA
<213> ORGANISM: Artificial sequence
<220> FEATURE:
<223> OTHER INFORMATION: Primer 5

<400> SEQUENCE: 9
ctagaaattc atgaacccgt ctcgtca       27

<210> SEQ ID NO 10
<211> LENGTH: 25
<212> TYPE: DNA
<213> ORGANISM: Artificial sequence
<220> FEATURE:
<223> OTHER INFORMATION: Primer 6

<400> SEQUENCE: 10

```
<210> SEQ ID NO 11
<211> LENGTH: 1440
<212> TYPE: DNA
<213> ORGANISM: Arabidopsis thaliana
<220> FEATURE:
<221> NAME/KEY: CDS
<222> LOCATION: (1)..(1440)

<400> SEQUENCE: 11
```

| | | | | | | | | | | | | | | | | |
|---|---|---|---|---|---|---|---|---|---|---|---|---|---|---|---|---|
| atg | aac | ccg | tct | cgt | cat | act | cat | gtg | atg | ctc | gta | tct | ttc | ccc | ggc | 48 |
| Met | Asn | Pro | Ser | Arg | His | Thr | His | Val | Met | Leu | Val | Ser | Phe | Pro | Gly | |
| 1 | | | | 5 | | | | | 10 | | | | | 15 | | |
| caa | ggt | cac | gta | aac | cct | cta | ctt | cgt | ctc | gga | aag | ctc | ata | gcc | tct | 96 |
| Gln | Gly | His | Val | Asn | Pro | Leu | Leu | Arg | Leu | Gly | Lys | Leu | Ile | Ala | Ser | |
| | | | 20 | | | | | 25 | | | | | 30 | | | |
| aaa | ggc | tta | ctc | gtc | acc | ttt | gtc | acc | aca | gag | aag | cca | tgg | ggc | aag | 144 |
| Lys | Gly | Leu | Leu | Val | Thr | Phe | Val | Thr | Thr | Glu | Lys | Pro | Trp | Gly | Lys | |
| | 35 | | | | | 40 | | | | | 45 | | | | | |
| aag | atg | cgt | caa | gcc | aac | aag | att | caa | gac | ggt | gtg | ctc | aaa | ccg | gtc | 192 |
| Lys | Met | Arg | Gln | Ala | Asn | Lys | Ile | Gln | Asp | Gly | Val | Leu | Lys | Pro | Val | |
| 50 | | | | | 55 | | | | | 60 | | | | | | |
| ggt | cta | ggt | ttc | atc | cgg | ttt | gag | ttc | ttc | tct | gac | ggc | ttc | gcc | gac | 240 |
| Gly | Leu | Gly | Phe | Ile | Arg | Phe | Glu | Phe | Phe | Ser | Asp | Gly | Phe | Ala | Asp | |
| 65 | | | | | 70 | | | | | 75 | | | | | 80 | |
| gac | gat | gaa | aaa | aga | ttc | gac | ttc | gat | gcc | ttc | cga | cca | cac | ctt | gaa | 288 |
| Asp | Asp | Glu | Lys | Arg | Phe | Asp | Phe | Asp | Ala | Phe | Arg | Pro | His | Leu | Glu | |
| | | | | 85 | | | | | 90 | | | | | 95 | | |
| gct | gtc | gga | aaa | caa | gag | atc | aag | aat | ctc | gtt | aag | aga | tat | aac | aag | 336 |
| Ala | Val | Gly | Lys | Gln | Glu | Ile | Lys | Asn | Leu | Val | Lys | Arg | Tyr | Asn | Lys | |
| | | | 100 | | | | | 105 | | | | | 110 | | | |
| gag | ccg | gtg | acg | tgt | ctc | ata | aac | aac | gct | ttt | gtc | cca | tgg | gta | tgt | 384 |
| Glu | Pro | Val | Thr | Cys | Leu | Ile | Asn | Asn | Ala | Phe | Val | Pro | Trp | Val | Cys | |
| | 115 | | | | | 120 | | | | | 125 | | | | | |
| gat | gtc | gcc | gag | gag | ctt | cac | atc | cct | tcg | gct | gtt | cta | tgg | gtc | cag | 432 |
| Asp | Val | Ala | Glu | Glu | Leu | His | Ile | Pro | Ser | Ala | Val | Leu | Trp | Val | Gln | |
| 130 | | | | | 135 | | | | | 140 | | | | | | |
| tct | tgt | gct | tgt | ctc | acg | gct | tat | tac | tat | tac | cac | cac | cgg | tta | gtt | 480 |
| Ser | Cys | Ala | Cys | Leu | Thr | Ala | Tyr | Tyr | Tyr | Tyr | His | His | Arg | Leu | Val | |
| 145 | | | | | 150 | | | | | 155 | | | | | 160 | |
| aag | ttc | ccg | acc | aaa | acc | gag | ccg | gac | atc | agc | gtt | gaa | atc | cct | tgc | 528 |
| Lys | Phe | Pro | Thr | Lys | Thr | Glu | Pro | Asp | Ile | Ser | Val | Glu | Ile | Pro | Cys | |
| | | | | 165 | | | | | 170 | | | | | 175 | | |
| ttg | cca | ttg | tta | aag | cat | gac | gag | atc | cca | agc | ttt | ctt | cac | cct | tcg | 576 |
| Leu | Pro | Leu | Leu | Lys | His | Asp | Glu | Ile | Pro | Ser | Phe | Leu | His | Pro | Ser | |
| | | | 180 | | | | | 185 | | | | | 190 | | | |
| tct | ccg | tat | aca | gct | ttt | gga | gat | atc | att | tta | gac | cag | tta | aag | aga | 624 |
| Ser | Pro | Tyr | Thr | Ala | Phe | Gly | Asp | Ile | Ile | Leu | Asp | Gln | Leu | Lys | Arg | |
| | | 195 | | | | | 200 | | | | | 205 | | | | |
| ttc | gaa | aac | cac | aag | tct | ttc | tat | ctt | ttc | atc | gac | act | ttt | cgc | gaa | 672 |
| Phe | Glu | Asn | His | Lys | Ser | Phe | Tyr | Leu | Phe | Ile | Asp | Thr | Phe | Arg | Glu | |
| | 210 | | | | | 215 | | | | | 220 | | | | | |
| cta | gaa | aaa | gac | atc | atg | gac | cac | atg | tca | caa | ctt | tgt | cct | caa | gcc | 720 |
| Leu | Glu | Lys | Asp | Ile | Met | Asp | His | Met | Ser | Gln | Leu | Cys | Pro | Gln | Ala | |
| 225 | | | | | 230 | | | | | 235 | | | | | 240 | |
| atc | atc | agt | cct | gtc | ggt | ccg | ctc | ttc | aag | atg | gct | caa | acc | ttg | agt | 768 |
| Ile | Ile | Ser | Pro | Val | Gly | Pro | Leu | Phe | Lys | Met | Ala | Gln | Thr | Leu | Ser | |
| | | | | 245 | | | | | 250 | | | | | 255 | | |
| tct | gac | gtt | aag | gga | gat | ata | tcc | gag | cca | gcg | agt | gac | tgc | atg | gaa | 816 |

```
Ser Asp Val Lys Gly Asp Ile Ser Glu Pro Ala Ser Asp Cys Met Glu
            260                 265                 270 tgg ctt gac tca aga gaa cca tcc tca gtc gtt tac atc tcc ttt ggg        864
Trp Leu Asp Ser Arg Glu Pro Ser Ser Val Val Tyr Ile Ser Phe Gly
        275                 280                 285 act ata gcc aac ttg aag caa gag cag atg gag gag atc gct cat ggc        912
Thr Ile Ala Asn Leu Lys Gln Glu Gln Met Glu Glu Ile Ala His Gly
    290                 295                 300 gtt ttg agc tct ggc ttg tcg gtc tta tgg gtg gtt cgg cct ccc atg        960
Val Leu Ser Ser Gly Leu Ser Val Leu Trp Val Val Arg Pro Pro Met
305                 310                 315                 320 gaa ggg aca ttt gta gaa cca cat gtt ttg cct cga gag ctc gaa gaa       1008
Glu Gly Thr Phe Val Glu Pro His Val Leu Pro Arg Glu Leu Glu Glu
                325                 330                 335 aag ggt aaa atc gtg gaa tgg tgt ccc caa gag aga gtc ttg gct cat       1056
Lys Gly Lys Ile Val Glu Trp Cys Pro Gln Glu Arg Val Leu Ala His
            340                 345                 350 cct gcg att gct tgt ttc tta agt cac tgc gga tgg aac tcg aca atg       1104
Pro Ala Ile Ala Cys Phe Leu Ser His Cys Gly Trp Asn Ser Thr Met
        355                 360                 365 gag gct tta act gcc gga gtc ccc gtt gtt tgt ttt ccg caa tgg gga       1152
Glu Ala Leu Thr Ala Gly Val Pro Val Val Cys Phe Pro Gln Trp Gly
    370                 375                 380 gat caa gtg act gat gcg gtg tac ttg gct gat gtt ttc aag aca gga       1200
Asp Gln Val Thr Asp Ala Val Tyr Leu Ala Asp Val Phe Lys Thr Gly
385                 390                 395                 400 gtg aga cta ggc cgc gga gcc gct gag gag atg att gtt tcg agg gag       1248
Val Arg Leu Gly Arg Gly Ala Ala Glu Glu Met Ile Val Ser Arg Glu
                405                 410                 415 gtt gta gca gag aag ctg ctt gag gcc aca gtt ggg gaa aag gcg gtg       1296
Val Val Ala Glu Lys Leu Leu Glu Ala Thr Val Gly Glu Lys Ala Val
            420                 425                 430 gag ctg aga gaa aac gct cgg agg tgg aag gcg gag gcc gag gcc gcc       1344
Glu Leu Arg Glu Asn Ala Arg Arg Trp Lys Ala Glu Ala Glu Ala Ala
        435                 440                 445 gtg gcg gac ggt gga tca tct gat atg aac ttt aaa gag ttt gtg gac       1392
Val Ala Asp Gly Gly Ser Ser Asp Met Asn Phe Lys Glu Phe Val Asp
    450                 455                 460 aag ttg gtt acg aaa cat gtg acg aga gaa gac aac gga gaa cac tag       1440
Lys Leu Val Thr Lys His Val Thr Arg Glu Asp Asn Gly Glu His
465                 470                 475

<210> SEQ ID NO 12
<211> LENGTH: 479
<212> TYPE: PRT
<213> ORGANISM: Arabidopsis thaliana

<400> SEQUENCE: 12

Met Asn Pro Ser Arg His Thr His Val Met Leu Val Ser Phe Pro Gly
1               5                   10                  15

Gln Gly His Val Asn Pro Leu Leu Arg Leu Gly Lys Leu Ile Ala Ser
            20                  25                  30

Lys Gly Leu Leu Val Thr Phe Val Thr Thr Glu Lys Pro Trp Gly Lys
        35                  40                  45

Lys Met Arg Gln Ala Asn Lys Ile Gln Asp Gly Val Leu Lys Pro Val
    50                  55                  60

Gly Leu Gly Phe Ile Arg Phe Glu Phe Phe Ser Asp Gly Phe Ala Asp
65                  70                  75                  80

Asp Asp Glu Lys Arg Phe Asp Phe Asp Ala Phe Arg Pro His Leu Glu
```

```
                    85                  90                  95
Ala Val Gly Lys Gln Glu Ile Lys Asn Leu Val Lys Arg Tyr Asn Lys
                100                 105                 110

Glu Pro Val Thr Cys Leu Ile Asn Asn Ala Phe Val Pro Trp Val Cys
            115                 120                 125

Asp Val Ala Glu Leu His Ile Pro Ser Ala Val Leu Trp Val Gln
        130                 135                 140

Ser Cys Ala Cys Leu Thr Ala Tyr Tyr Tyr His His Arg Leu Val
145                 150                 155                 160

Lys Phe Pro Thr Lys Thr Glu Pro Asp Ile Ser Val Glu Ile Pro Cys
                165                 170                 175

Leu Pro Leu Leu Lys His Asp Glu Ile Pro Ser Phe Leu His Pro Ser
            180                 185                 190

Ser Pro Tyr Thr Ala Phe Gly Asp Ile Ile Leu Asp Gln Leu Lys Arg
        195                 200                 205

Phe Glu Asn His Lys Ser Phe Tyr Leu Phe Ile Asp Thr Phe Arg Glu
    210                 215                 220

Leu Glu Lys Asp Ile Met Asp His Met Ser Gln Leu Cys Pro Gln Ala
225                 230                 235                 240

Ile Ile Ser Pro Val Gly Pro Leu Phe Lys Met Ala Gln Thr Leu Ser
                245                 250                 255

Ser Asp Val Lys Gly Asp Ile Ser Glu Pro Ala Ser Asp Cys Met Glu
            260                 265                 270

Trp Leu Asp Ser Arg Glu Pro Ser Ser Val Val Tyr Ile Ser Phe Gly
        275                 280                 285

Thr Ile Ala Asn Leu Lys Gln Glu Gln Met Glu Glu Ile Ala His Gly
    290                 295                 300

Val Leu Ser Ser Gly Leu Ser Val Leu Trp Val Val Arg Pro Pro Met
305                 310                 315                 320

Glu Gly Thr Phe Val Glu Pro His Val Leu Pro Arg Glu Leu Glu Glu
                325                 330                 335

Lys Gly Lys Ile Val Glu Trp Cys Pro Gln Glu Arg Val Leu Ala His
            340                 345                 350

Pro Ala Ile Ala Cys Phe Leu Ser His Cys Gly Trp Asn Ser Thr Met
        355                 360                 365

Glu Ala Leu Thr Ala Gly Val Pro Val Val Cys Phe Pro Gln Trp Gly
    370                 375                 380

Asp Gln Val Thr Asp Ala Val Tyr Leu Ala Asp Val Phe Lys Thr Gly
385                 390                 395                 400

Val Arg Leu Gly Arg Gly Ala Ala Glu Glu Met Ile Val Ser Arg Glu
                405                 410                 415

Val Val Ala Glu Lys Leu Leu Glu Ala Thr Val Gly Glu Lys Ala Val
            420                 425                 430

Glu Leu Arg Glu Asn Ala Arg Arg Trp Lys Ala Glu Ala Glu Ala Ala
        435                 440                 445

Val Ala Asp Gly Gly Ser Ser Asp Met Asn Phe Lys Glu Phe Val Asp
        450                 455                 460

Lys Leu Val Thr Lys His Val Thr Arg Glu Asp Asn Gly Glu His
465                 470                 475

<210> SEQ ID NO 13
<211> LENGTH: 29
<212> TYPE: DNA
<213> ORGANISM: Artificial sequence
```

```
<220> FEATURE:
<223> OTHER INFORMATION: Primer 7

<400> SEQUENCE: 13
caaaaaaaaa atcatgaaga tggaatcgt                                29

<210> SEQ ID NO 14
<211> LENGTH: 29
<212> TYPE: DNA
<213> ORGANISM: Artificial sequence
<220> FEATURE:
<223> OTHER INFORMATION: Primer 8

<400> SEQUENCE: 14
atattgtcga cttacacgac attattaat                                29

<210> SEQ ID NO 15
<211> LENGTH: 1428
<212> TYPE: DNA
<213> ORGANISM: Arabidopsis thaliana
<220> FEATURE:
<221> NAME/KEY: CDS
<222> LOCATION: (1)..(1428)

<400> SEQUENCE: 15 atg aag atg gaa tcg tcg tta cct cat gtg atg ctc gta tca ttc cca      48
Met Lys Met Glu Ser Ser Leu Pro His Val Met Leu Val Ser Phe Pro
  1               5                  10                  15 ggg caa ggt cac ata agc cct ctt ctt cgt ctc gga aag atc att gcc      96
Gly Gln Gly His Ile Ser Pro Leu Leu Arg Leu Gly Lys Ile Ile Ala
             20                  25                  30 tct aaa ggc tta atc gtc acc ttt gta acc aca gag gaa cca ttg ggc     144
Ser Lys Gly Leu Ile Val Thr Phe Val Thr Thr Glu Glu Pro Leu Gly
         35                  40                  45 aag aag atg cgt caa gcc aac aat att caa gac ggt gtg ctc aaa ccg     192
Lys Lys Met Arg Gln Ala Asn Asn Ile Gln Asp Gly Val Leu Lys Pro
     50                  55                  60 gtc ggg cta ggt ttt ctc cgg ttc gag ttc ttc gag gat gga ttt gtc     240
Val Gly Leu Gly Phe Leu Arg Phe Glu Phe Phe Glu Asp Gly Phe Val
 65                  70                  75                  80 tac aaa gaa gac ttt gat ttg tta caa aaa tca ctt gaa gtt tcc gga     288
Tyr Lys Glu Asp Phe Asp Leu Leu Gln Lys Ser Leu Glu Val Ser Gly
                 85                  90                  95 aaa cga gag atc aag aat ctt gtc aag aaa tat gag aag caa cca gtg     336
Lys Arg Glu Ile Lys Asn Leu Val Lys Lys Tyr Glu Lys Gln Pro Val
            100                 105                 110 aga tgt ctc ata aat aat gcc ttt gtt cca tgg gtt tgt gac ata gcc     384
Arg Cys Leu Ile Asn Asn Ala Phe Val Pro Trp Val Cys Asp Ile Ala
        115                 120                 125 gag gag ctt caa atc cca tca gct gtt ctt tgg gtc cag tct tgt gct     432
Glu Glu Leu Gln Ile Pro Ser Ala Val Leu Trp Val Gln Ser Cys Ala
    130                 135                 140 tgc ctc gcc gct tat tac tat tac cac cac cag tta gtt aag ttt ccg     480
Cys Leu Ala Ala Tyr Tyr Tyr Tyr His His Gln Leu Val Lys Phe Pro
145                 150                 155                 160 acc gaa acc gag ccg gaa ata acc gtt gac gtc cct ttc aag cca tta     528
Thr Glu Thr Glu Pro Glu Ile Thr Val Asp Val Pro Phe Lys Pro Leu
                165                 170                 175 aca ttg aag cat gac gag atc cct agc ttt ctt cac cct tcc tct ccg     576
Thr Leu Lys His Asp Glu Ile Pro Ser Phe Leu His Pro Ser Ser Pro
            180                 185                 190 ctg tcc tct ata gga ggt acc att tta gag cag atc aag cga ctt cac     624
```

```
                                                                -continued

Leu Ser Ser Ile Gly Gly Thr Ile Leu Glu Gln Ile Lys Arg Leu His
        195                 200                 205 aag cct ttc tct gtt ctc atc gaa act ttt caa gaa ctt gaa aaa gat        672
Lys Pro Phe Ser Val Leu Ile Glu Thr Phe Gln Glu Leu Glu Lys Asp
    210                 215                 220 acc att gac cac atg tcc cag ctc tgc cct caa gtc aac ttc aac ccc        720
Thr Ile Asp His Met Ser Gln Leu Cys Pro Gln Val Asn Phe Asn Pro
225                 230                 235                 240 atc ggt ccg ctt ttt act atg gct aaa acc ata agg tct gac atc aag        768
Ile Gly Pro Leu Phe Thr Met Ala Lys Thr Ile Arg Ser Asp Ile Lys
                245                 250                 255 gga gac atc tcc aag cca gat agt gac tgc ata gag tgg ctt gac tcg        816
Gly Asp Ile Ser Lys Pro Asp Ser Asp Cys Ile Glu Trp Leu Asp Ser
            260                 265                 270 aga gaa cca tcc tcc gtt gtt tac atc tct ttt ggg act ttg gct ttc        864
Arg Glu Pro Ser Ser Val Val Tyr Ile Ser Phe Gly Thr Leu Ala Phe
        275                 280                 285 ttg aag caa aac cag atc gac gag att gct cac ggc att ctc aac tcc        912
Leu Lys Gln Asn Gln Ile Asp Glu Ile Ala His Gly Ile Leu Asn Ser
    290                 295                 300 ggg ttg tcc tgc tta tgg gtt ttg cgg cct ccc tta gaa ggc tta gcc        960
Gly Leu Ser Cys Leu Trp Val Leu Arg Pro Pro Leu Glu Gly Leu Ala
305                 310                 315                 320 ata gaa ccg cat gtc ttg cct cta gag ctt gaa gag aaa ggg aag att       1008
Ile Glu Pro His Val Leu Pro Leu Glu Leu Glu Glu Lys Gly Lys Ile
                325                 330                 335 gtg gaa tgg tgt caa caa gag aaa gtt ttg gct cat cct gcg gtt gct       1056
Val Glu Trp Cys Gln Gln Glu Lys Val Leu Ala His Pro Ala Val Ala
            340                 345                 350 tgc ttc tta agt cac tgt gga tgg aac tca acc atg gag gct tta act       1104
Cys Phe Leu Ser His Cys Gly Trp Asn Ser Thr Met Glu Ala Leu Thr
        355                 360                 365 tca gga gtt ccc gtt att tgt ttc ccg cag tgg gga gat cag gtg aca       1152
Ser Gly Val Pro Val Ile Cys Phe Pro Gln Trp Gly Asp Gln Val Thr
    370                 375                 380 aat gcg gtg tac atg att gat gtt ttc aag aca gga ttg aga ctc agc       1200
Asn Ala Val Tyr Met Ile Asp Val Phe Lys Thr Gly Leu Arg Leu Ser
385                 390                 395                 400 cgt gga gct tcc gat gag agg att gtt cca agg gag gag gtt gct gag       1248
Arg Gly Ala Ser Asp Glu Arg Ile Val Pro Arg Glu Glu Val Ala Glu
                405                 410                 415 cga ctg ctt gag gcc acc gtt gga gag aag gcg gtg gag ctg aga gaa       1296
Arg Leu Leu Glu Ala Thr Val Gly Glu Lys Ala Val Glu Leu Arg Glu
            420                 425                 430 aac gct cgg agg tgg aag gag gag gcg gag tct gcc gtg gct tac ggt       1344
Asn Ala Arg Arg Trp Lys Glu Glu Ala Glu Ser Ala Val Ala Tyr Gly
        435                 440                 445 gga aca tcg gaa agg aat ttt caa gag ttt gtt gac aag ttg gtt gat       1392
Gly Thr Ser Glu Arg Asn Phe Gln Glu Phe Val Asp Lys Leu Val Asp
    450                 455                 460 gtc aag aca atg aca aac att aat aat gtc gtg taa                       1428
Val Lys Thr Met Thr Asn Ile Asn Asn Val Val
465                 470                 475

<210> SEQ ID NO 16
<211> LENGTH: 475
<212> TYPE: PRT
<213> ORGANISM: Arabidopsis thaliana

<400> SEQUENCE: 16
```

```
Met Lys Met Glu Ser Ser Leu Pro His Val Met Leu Val Ser Phe Pro
1               5                   10                  15
Gly Gln Gly His Ile Ser Pro Leu Leu Arg Leu Gly Lys Ile Ile Ala
                20                  25                  30
Ser Lys Gly Leu Ile Val Thr Phe Val Thr Thr Glu Glu Pro Leu Gly
            35                  40                  45
Lys Lys Met Arg Gln Ala Asn Asn Ile Gln Asp Gly Val Leu Lys Pro
        50                  55                  60
Val Gly Leu Gly Phe Leu Arg Phe Glu Phe Phe Glu Asp Gly Phe Val
65                  70                  75                  80
Tyr Lys Glu Asp Phe Asp Leu Leu Gln Lys Ser Leu Glu Val Ser Gly
                85                  90                  95
Lys Arg Glu Ile Lys Asn Leu Val Lys Lys Tyr Glu Lys Gln Pro Val
            100                 105                 110
Arg Cys Leu Ile Asn Asn Ala Phe Val Pro Trp Val Cys Asp Ile Ala
        115                 120                 125
Glu Glu Leu Gln Ile Pro Ser Ala Val Leu Trp Val Gln Ser Cys Ala
        130                 135                 140
Cys Leu Ala Ala Tyr Tyr Tyr His His Gln Leu Val Lys Phe Pro
145                 150                 155                 160
Thr Glu Thr Glu Pro Glu Ile Thr Val Asp Val Pro Phe Lys Pro Leu
                165                 170                 175
Thr Leu Lys His Asp Glu Ile Pro Ser Phe Leu His Pro Ser Ser Pro
                180                 185                 190
Leu Ser Ser Ile Gly Gly Thr Ile Leu Glu Gln Ile Lys Arg Leu His
            195                 200                 205
Lys Pro Phe Ser Val Leu Ile Glu Thr Phe Gln Glu Leu Glu Lys Asp
        210                 215                 220
Thr Ile Asp His Met Ser Gln Leu Cys Pro Gln Val Asn Phe Asn Pro
225                 230                 235                 240
Ile Gly Pro Leu Phe Thr Met Ala Lys Thr Ile Arg Ser Asp Ile Lys
                245                 250                 255
Gly Asp Ile Ser Lys Pro Asp Ser Asp Cys Ile Glu Trp Leu Asp Ser
                260                 265                 270
Arg Glu Pro Ser Ser Val Val Tyr Ile Ser Phe Gly Thr Leu Ala Phe
            275                 280                 285
Leu Lys Gln Asn Gln Ile Asp Glu Ile Ala His Gly Ile Leu Asn Ser
        290                 295                 300
Gly Leu Ser Cys Leu Trp Val Leu Arg Pro Pro Leu Glu Gly Leu Ala
305                 310                 315                 320
Ile Glu Pro His Val Leu Pro Leu Glu Leu Glu Glu Lys Gly Lys Ile
                325                 330                 335
Val Glu Trp Cys Gln Gln Glu Lys Val Leu Ala His Pro Ala Val Ala
                340                 345                 350
Cys Phe Leu Ser His Cys Gly Trp Asn Ser Thr Met Glu Ala Leu Thr
            355                 360                 365
Ser Gly Val Pro Val Ile Cys Phe Pro Gln Trp Gly Asp Gln Val Thr
        370                 375                 380
Asn Ala Val Tyr Met Ile Asp Val Phe Lys Thr Gly Leu Arg Leu Ser
385                 390                 395                 400
Arg Gly Ala Ser Asp Glu Arg Ile Val Pro Arg Glu Glu Val Ala Glu
                405                 410                 415
Arg Leu Leu Glu Ala Thr Val Gly Glu Lys Ala Val Glu Leu Arg Glu
```

```
                    420             425             430
Asn Ala Arg Arg Trp Lys Glu Glu Ala Glu Ser Ala Val Ala Tyr Gly
            435                 440                 445

Gly Thr Ser Glu Arg Asn Phe Gln Glu Phe Val Asp Lys Leu Val Asp
    450                 455                 460

Val Lys Thr Met Thr Asn Ile Asn Asn Val Val
465                 470                 475

<210> SEQ ID NO 17
<211> LENGTH: 1437
<212> TYPE: DNA
<213> ORGANISM: Vitis ssp.
<220> FEATURE:
<221> NAME/KEY: CDS
<222> LOCATION: (1)..(1437)

<400> SEQUENCE: 17 atg gga tct gaa tca aag cta gtt cat gtg ttt ttg gtt tcc ttc cct      48
Met Gly Ser Glu Ser Lys Leu Val His Val Phe Leu Val Ser Phe Pro
1               5                   10                  15 gga caa ggg cat gtc aac cct ttg ctc agg ctg ggg aag cgt ctg gct      96
Gly Gln Gly His Val Asn Pro Leu Leu Arg Leu Gly Lys Arg Leu Ala
            20                  25                  30 tca aag ggc ttg ctt gtt acc ttc tcc act cca gag agt atc ggg aag     144
Ser Lys Gly Leu Leu Val Thr Phe Ser Thr Pro Glu Ser Ile Gly Lys
        35                  40                  45 cag atg agg aaa gcc agt aac att act gac cag ccg aca ccg gtc gga     192
Gln Met Arg Lys Ala Ser Asn Ile Thr Asp Gln Pro Thr Pro Val Gly
    50                  55                  60 gaa ggt ctg atc agg ttc gag ttt ttc gaa gat gag tgg gac gag aac     240
Glu Gly Leu Ile Arg Phe Glu Phe Phe Glu Asp Glu Trp Asp Glu Asn
65                  70                  75                  80 gag ccc aag cgc caa gat ttg gac ctt tac ttg ccc cag ctg gag ctc     288
Glu Pro Lys Arg Gln Asp Leu Asp Leu Tyr Leu Pro Gln Leu Glu Leu
                85                  90                  95 gtg ggc aaa aag gtt ctt cct cag atg atc aaa aaa cac gca gag cag     336
Val Gly Lys Lys Val Leu Pro Gln Met Ile Lys Lys His Ala Glu Gln
            100                 105                 110 gat cga cct gtc tcc tgc ctc atc aac aac cca ttt att cca tgg gtt     384
Asp Arg Pro Val Ser Cys Leu Ile Asn Asn Pro Phe Ile Pro Trp Val
        115                 120                 125 tct gat gta gca gct gat ctt gga atc ccc agt gcc atg ctt tgg gtt     432
Ser Asp Val Ala Ala Asp Leu Gly Ile Pro Ser Ala Met Leu Trp Val
    130                 135                 140 caa tct tgc gct tgc ttt tct acg tat tac cac tac tac cat ggc tta     480
Gln Ser Cys Ala Cys Phe Ser Thr Tyr Tyr His Tyr Tyr His Gly Leu
145                 150                 155                 160 gtc cct ttt ccc tcc gaa gct gag cct gaa atc gat gtt caa ttg cca     528
Val Pro Phe Pro Ser Glu Ala Glu Pro Glu Ile Asp Val Gln Leu Pro
                165                 170                 175 tgt atg cct ctc ttg aag tat gat gaa gtc gct agc ttc ttg tac ccg     576
Cys Met Pro Leu Leu Lys Tyr Asp Glu Val Ala Ser Phe Leu Tyr Pro
            180                 185                 190 acc act ccc tac cca ttc ctg agg aga gct atc tta ggc cag tac agg     624
Thr Thr Pro Tyr Pro Phe Leu Arg Arg Ala Ile Leu Gly Gln Tyr Arg
        195                 200                 205 aac ctg gac aag ccc ttc tgt ata ttg atg gac acg ttc caa gaa ctg     672
Asn Leu Asp Lys Pro Phe Cys Ile Leu Met Asp Thr Phe Gln Glu Leu
    210                 215                 220 gaa ccc gaa gtc atc gaa tac atg tcc aag atc tgc ccg atc aag cct     720
```

-continued

```
Glu Pro Glu Val Ile Glu Tyr Met Ser Lys Ile Cys Pro Ile Lys Pro
225                 230                 235                 240 gta gga cct tta tac aag aac cct aaa gtg cca aac gcc gct gtc cgt    768
Val Gly Pro Leu Tyr Lys Asn Pro Lys Val Pro Asn Ala Ala Val Arg
                245                 250                 255 ggc gac ttc atg aag gcc gac gac tgc atc gag tgg ctc gac tcc aag    816
Gly Asp Phe Met Lys Ala Asp Asp Cys Ile Glu Trp Leu Asp Ser Lys
            260                 265                 270 cct ccc tcc tcc atc gtc tac gtc tct ttt gga agc gtc gtg tac ctg    864
Pro Pro Ser Ser Ile Val Tyr Val Ser Phe Gly Ser Val Val Tyr Leu
        275                 280                 285 aaa caa gac caa gta gac gag atc gct tat ggg ctc tta aac tcc ggc    912
Lys Gln Asp Gln Val Asp Glu Ile Ala Tyr Gly Leu Leu Asn Ser Gly
    290                 295                 300 ctg caa ttc tta tgg gtg atg aaa ccg ccg cac aaa gac gcc ggc ctg    960
Leu Gln Phe Leu Trp Val Met Lys Pro Pro His Lys Asp Ala Gly Leu
305                 310                 315                 320 gaa ctc cta gtt ctt cca gaa ggg ttc ttg gaa aag gcc ggt gac aaa    1008
Glu Leu Leu Val Leu Pro Glu Gly Phe Leu Glu Lys Ala Gly Asp Lys
                325                 330                 335 ggc aag gtg gtg caa tgg agc ccg caa gag caa gtc tta gct cac ccc    1056
Gly Lys Val Val Gln Trp Ser Pro Gln Glu Gln Val Leu Ala His Pro
            340                 345                 350 tcc gtt gcc tgt ttc gtt acc cac tgt gga tgg aac tca tcc atg gag    1104
Ser Val Ala Cys Phe Val Thr His Cys Gly Trp Asn Ser Ser Met Glu
        355                 360                 365 gct ctc agc tcc ggc atg ccg gtg gtg gcg ttc cca cag tgg gga gat    1152
Ala Leu Ser Ser Gly Met Pro Val Val Ala Phe Pro Gln Trp Gly Asp
370                 375                 380 caa gtc acc gac gcc aag tac ttg gtg gac gaa ttc aaa att gga gtg    1200
Gln Val Thr Asp Ala Lys Tyr Leu Val Asp Glu Phe Lys Ile Gly Val
385                 390                 395                 400 aga atg tgc aga ggc gag gcc gaa aac aag ctc atc acc cgg gac gag    1248
Arg Met Cys Arg Gly Glu Ala Glu Asn Lys Leu Ile Thr Arg Asp Glu
                405                 410                 415 gtg gag aag tgt ttg atc gag gcc acc acc gga cca aag gca gcg gag    1296
Val Glu Lys Cys Leu Ile Glu Ala Thr Thr Gly Pro Lys Ala Ala Glu
            420                 425                 430 ttg aag caa aac gcc atg aag tgg aag aag gcg gca gag cag gcg gtg    1344
Leu Lys Gln Asn Ala Met Lys Trp Lys Lys Ala Ala Glu Gln Ala Val
        435                 440                 445 gcg gag ggc ggt tcc tcc gaa cgg aat cta cag ggt ttt gtc gac gag    1392
Ala Glu Gly Gly Ser Ser Glu Arg Asn Leu Gln Gly Phe Val Asp Glu
450                 455                 460 gtt cgg aga agg agc att gag atc att tac aaa aca aaa att taa        1437
Val Arg Arg Arg Ser Ile Glu Ile Ile Tyr Lys Thr Lys Ile
465                 470                 475
```

<210> SEQ ID NO 18
<211> LENGTH: 478
<212> TYPE: PRT
<213> ORGANISM: Vitis ssp.

<400> SEQUENCE: 18

```
Met Gly Ser Glu Ser Lys Leu Val His Val Phe Leu Val Ser Phe Pro
1               5                   10                  15

Gly Gln Gly His Val Asn Pro Leu Leu Arg Leu Gly Lys Arg Leu Ala
                20                  25                  30

Ser Lys Gly Leu Leu Val Thr Phe Ser Thr Pro Glu Ser Ile Gly Lys
            35                  40                  45
```

-continued

Gln Met Arg Lys Ala Ser Asn Ile Thr Asp Gln Pro Thr Pro Val Gly
     50                  55                  60

Glu Gly Leu Ile Arg Phe Glu Phe Phe Glu Asp Glu Trp Asp Glu Asn
65                   70                  75                  80

Glu Pro Lys Arg Gln Asp Leu Asp Leu Tyr Leu Pro Gln Leu Glu Leu
                 85                  90                  95

Val Gly Lys Lys Val Leu Pro Gln Met Ile Lys Lys His Ala Glu Gln
             100                 105                 110

Asp Arg Pro Val Ser Cys Leu Ile Asn Asn Pro Phe Ile Pro Trp Val
            115                 120                 125

Ser Asp Val Ala Ala Asp Leu Gly Ile Pro Ser Ala Met Leu Trp Val
        130                 135                 140

Gln Ser Cys Ala Cys Phe Ser Thr Tyr Tyr His Tyr Tyr His Gly Leu
145                 150                 155                 160

Val Pro Phe Pro Ser Glu Ala Glu Pro Glu Ile Asp Val Gln Leu Pro
                165                 170                 175

Cys Met Pro Leu Leu Lys Tyr Asp Glu Val Ala Ser Phe Leu Tyr Pro
            180                 185                 190

Thr Thr Pro Tyr Pro Phe Leu Arg Arg Ala Ile Leu Gly Gln Tyr Arg
        195                 200                 205

Asn Leu Asp Lys Pro Phe Cys Ile Leu Met Asp Thr Phe Gln Glu Leu
    210                 215                 220

Glu Pro Glu Val Ile Glu Tyr Met Ser Lys Ile Cys Pro Ile Lys Pro
225                 230                 235                 240

Val Gly Pro Leu Tyr Lys Asn Pro Lys Val Pro Asn Ala Ala Val Arg
                245                 250                 255

Gly Asp Phe Met Lys Ala Asp Asp Cys Ile Glu Trp Leu Asp Ser Lys
            260                 265                 270

Pro Pro Ser Ser Ile Val Tyr Val Ser Phe Gly Ser Val Val Tyr Leu
        275                 280                 285

Lys Gln Asp Gln Val Asp Glu Ile Ala Tyr Gly Leu Leu Asn Ser Gly
    290                 295                 300

Leu Gln Phe Leu Trp Val Met Lys Pro Pro His Lys Asp Ala Gly Leu
305                 310                 315                 320

Glu Leu Leu Val Leu Pro Glu Gly Phe Leu Glu Lys Ala Gly Asp Lys
                325                 330                 335

Gly Lys Val Val Gln Trp Ser Pro Gln Glu Gln Val Leu Ala His Pro
            340                 345                 350

Ser Val Ala Cys Phe Val Thr His Cys Gly Trp Asn Ser Ser Met Glu
        355                 360                 365

Ala Leu Ser Ser Gly Met Pro Val Val Ala Phe Pro Gln Trp Gly Asp
    370                 375                 380

Gln Val Thr Asp Ala Lys Tyr Leu Val Asp Glu Phe Lys Ile Gly Val
385                 390                 395                 400

Arg Met Cys Arg Gly Glu Ala Glu Asn Lys Leu Ile Thr Arg Asp Glu
                405                 410                 415

Val Glu Lys Cys Leu Ile Glu Ala Thr Thr Gly Pro Lys Ala Ala Glu
            420                 425                 430

Leu Lys Gln Asn Ala Met Lys Trp Lys Lys Ala Glu Gln Ala Val
        435                 440                 445

Ala Glu Gly Gly Ser Ser Glu Arg Asn Leu Gln Gly Phe Val Asp Glu
    450                 455                 460

```
Val Arg Arg Arg Ser Ile Glu Ile Ile Tyr Lys Thr Lys Ile
465                 470                 475

<210> SEQ ID NO 19
<211> LENGTH: 35
<212> TYPE: DNA
<213> ORGANISM: Artificial sequence
<220> FEATURE:
<223> OTHER INFORMATION: Primer 9

<400> SEQUENCE: 19
ctactcattt catatgggat ctgaatcaaa gctag                           35

<210> SEQ ID NO 20
<211> LENGTH: 36
<212> TYPE: DNA
<213> ORGANISM: Artificial sequence
<220> FEATURE:
<223> OTHER INFORMATION: Primer 10

<400> SEQUENCE: 20
catcttactg gatccacttc acacgtgtcc cttcaa                          36

<210> SEQ ID NO 21
<211> LENGTH: 1536
<212> TYPE: DNA
<213> ORGANISM: Eucalyptus grandis
<220> FEATURE:
<221> NAME/KEY: CDS
<222> LOCATION: (1)..(1536)

<400> SEQUENCE: 21 atg ggg tcg gag gca ctt gtc cac gtc ctc ttg gtc tca ttc cct ggc    48
Met Gly Ser Glu Ala Leu Val His Val Leu Leu Val Ser Phe Pro Gly
1               5                   10                  15 cag ggc cac gtc aac ccg ctc ctg agg ctt ggc aag cgc ctc gcc tcc    96
Gln Gly His Val Asn Pro Leu Leu Arg Leu Gly Lys Arg Leu Ala Ser
                20                  25                  30 aag ggc ctg ctc gtc acc ttc acg acc cca gag agc atc ggg aag gca   144
Lys Gly Leu Leu Val Thr Phe Thr Thr Pro Glu Ser Ile Gly Lys Ala
            35                  40                  45 atg cgc aag gcg agc aac atc ggc gag gag ctc tcc ccg gtc ggt gat   192
Met Arg Lys Ala Ser Asn Ile Gly Glu Glu Leu Ser Pro Val Gly Asp
        50                  55                  60 ggc ttc atc cgg ttt gag ttc ttc gag gac ggg tgg gac gag gac gag   240
Gly Phe Ile Arg Phe Glu Phe Phe Glu Asp Gly Trp Asp Glu Asp Glu
65                  70                  75                  80 ata cgc cgc cag gac ctc gac cag tac ctc ccc cag ctc gag aag gtc   288
Ile Arg Arg Gln Asp Leu Asp Gln Tyr Leu Pro Gln Leu Glu Lys Val
                85                  90                  95 ggg aag gtc ctc atc cct gag atg atc cgg cgc aac gcc gag caa ggc   336
Gly Lys Val Leu Ile Pro Glu Met Ile Arg Arg Asn Ala Glu Gln Gly
                100                 105                 110 cgc cct atc tct tgc ctc atc aac aat cct ttc atc ccc tgg gtc tcc   384
Arg Pro Ile Ser Cys Leu Ile Asn Asn Pro Phe Ile Pro Trp Val Ser
            115                 120                 125 gat gtt gcc gat agc ctc ggc ctc ccc tcg gcg atg ctc tgg gtg caa   432
Asp Val Ala Asp Ser Leu Gly Leu Pro Ser Ala Met Leu Trp Val Gln
        130                 135                 140 tcc tgt gca tgc ttc act tcg tac tac tac tac tac cat ggc ctg gtc   480
Ser Cys Ala Cys Phe Thr Ser Tyr Tyr Tyr Tyr Tyr His Gly Leu Val
145                 150                 155                 160 ccc ttc ccg tct gag aca gcg atg gag atc gat gtg caa ctc cct tgc   528
```

```
                Pro Phe Pro Ser Glu Thr Ala Met Glu Ile Asp Val Gln Leu Pro Cys
                                165                 170                 175 atg ccg ctc cta aag cac gac gag gtc ccg agc ttc ttg tac cca acg        576
Met Pro Leu Leu Lys His Asp Glu Val Pro Ser Phe Leu Tyr Pro Thr
            180                 185                 190 acc ccg tac cct ttc ctc cgg cgg gcg atc atg ggg cag tac aag aac        624
Thr Pro Tyr Pro Phe Leu Arg Arg Ala Ile Met Gly Gln Tyr Lys Asn
        195                 200                 205 ttg gac aag cca ttc tgc atc ctg atg gac acg ttc cag gag ctc gag        672
Leu Asp Lys Pro Phe Cys Ile Leu Met Asp Thr Phe Gln Glu Leu Glu
    210                 215                 220 cat gag atc att gag tac atg tcc aag atc agc ccc atc aag aca gtc        720
His Glu Ile Ile Glu Tyr Met Ser Lys Ile Ser Pro Ile Lys Thr Val
225                 230                 235                 240 ggg ccg ctc ttc aag aac cct aag gcc ccg aac gcc act gtc aag ggc        768
Gly Pro Leu Phe Lys Asn Pro Lys Ala Pro Asn Ala Thr Val Lys Gly
                245                 250                 255 gat ttc atg aag gct gac gac tgc gtc ggc tgg ctc gac tca aag cct        816
Asp Phe Met Lys Ala Asp Asp Cys Val Gly Trp Leu Asp Ser Lys Pro
            260                 265                 270 gct tcc tcg atc gtt tac gtg tcg ttt ggg agc gtc gtg tac ttg aag        864
Ala Ser Ser Ile Val Tyr Val Ser Phe Gly Ser Val Val Tyr Leu Lys
        275                 280                 285 caa gac cag tgg gat gag att gct tat ggg ctg ttg aac tcc ggg gtc        912
Gln Asp Gln Trp Asp Glu Ile Ala Tyr Gly Leu Leu Asn Ser Gly Val
    290                 295                 300 aac ttc ttg tgg gtc atg aag cct cca cac aag gac tct ggc tat gag        960
Asn Phe Leu Trp Val Met Lys Pro Pro His Lys Asp Ser Gly Tyr Glu
305                 310                 315                 320 gtt ctc aaa atg cct gaa ggg ttc ttg gag aag gct ggt gat agg ggc       1008
Val Leu Lys Met Pro Glu Gly Phe Leu Glu Lys Ala Gly Asp Arg Gly
                325                 330                 335 aag gtg gtg cag tgg agc ccg caa gag caa gtc ctg gct cac ccc tcg       1056
Lys Val Val Gln Trp Ser Pro Gln Glu Gln Val Leu Ala His Pro Ser
            340                 345                 350 gtg gcc tgc ttc gtc acg cac tgc ggt tgg aac tcg acc atg gag gcc       1104
Val Ala Cys Phe Val Thr His Cys Gly Trp Asn Ser Thr Met Glu Ala
        355                 360                 365 ttg acc tct ggc atg cct gtg gtg gcg ttc ccg cag tgg ggt gac cag       1152
Leu Thr Ser Gly Met Pro Val Val Ala Phe Pro Gln Trp Gly Asp Gln
    370                 375                 380 gtc acc gac gcc aag tac cta gtc gac gtg ttc aag gtc ggg gtg agg       1200
Val Thr Asp Ala Lys Tyr Leu Val Asp Val Phe Lys Val Gly Val Arg
385                 390                 395                 400 atg tgc cgg ggc gag gca gag aac aag ctg atc acg cgg gac gtg gtc       1248
Met Cys Arg Gly Glu Ala Glu Asn Lys Leu Ile Thr Arg Asp Val Val
                405                 410                 415 gag cag tgc ctc cgc gag gca acc tcg ggg ccc aag gcc gag gag atg       1296
Glu Gln Cys Leu Arg Glu Ala Thr Ser Gly Pro Lys Ala Glu Glu Met
            420                 425                 430 aag cag aac gcg atg aag tgg agc gcg gca gcg gag gcg gct gtg gca       1344
Lys Gln Asn Ala Met Lys Trp Ser Ala Ala Ala Glu Ala Ala Val Ala
        435                 440                 445 gag ggt ggc tcc tca gac cgg aac atc cag gcc ttc gtg gac gag gtg       1392
Glu Gly Gly Ser Ser Asp Arg Asn Ile Gln Ala Phe Val Asp Glu Val
    450                 455                 460 aag agg agg agc ctg gag gtg ctg gct gcg agt ggc aag tca acg gcc       1440
Lys Arg Arg Ser Leu Glu Val Leu Ala Ala Ser Gly Lys Ser Thr Ala
465                 470                 475                 480
```

```
aac gga ggg gcg gac ttg gcc aac aaa gtg gcg gcc aat ggg gtt gcg    1488
Asn Gly Gly Ala Asp Leu Ala Asn Lys Val Ala Ala Asn Gly Val Ala
            485                 490                 495 gag ctg ggc gag cca aag gtc aac ggg gag tta aag gtg gtg tcg tga    1536
Glu Leu Gly Glu Pro Lys Val Asn Gly Glu Leu Lys Val Val Ser
        500                 505                 510
```

<210> SEQ ID NO 22
<211> LENGTH: 511
<212> TYPE: PRT
<213> ORGANISM: Eucalyptus grandis

<400> SEQUENCE: 22

```
Met Gly Ser Glu Ala Leu Val His Val Leu Val Ser Phe Pro Gly
1               5                   10                  15

Gln Gly His Val Asn Pro Leu Leu Arg Leu Gly Lys Arg Leu Ala Ser
                20                  25                  30

Lys Gly Leu Leu Val Thr Phe Thr Thr Pro Glu Ser Ile Gly Lys Ala
        35                  40                  45

Met Arg Lys Ala Ser Asn Ile Gly Glu Glu Leu Ser Pro Val Gly Asp
    50                  55                  60

Gly Phe Ile Arg Phe Glu Phe Phe Glu Asp Gly Trp Asp Glu Asp Glu
65                  70                  75                  80

Ile Arg Arg Gln Asp Leu Asp Gln Tyr Leu Pro Gln Leu Glu Lys Val
                85                  90                  95

Gly Lys Val Leu Ile Pro Glu Met Ile Arg Arg Asn Ala Glu Gln Gly
            100                 105                 110

Arg Pro Ile Ser Cys Leu Ile Asn Asn Pro Phe Ile Pro Trp Val Ser
        115                 120                 125

Asp Val Ala Asp Ser Leu Gly Leu Pro Ser Ala Met Leu Trp Val Gln
    130                 135                 140

Ser Cys Ala Cys Phe Thr Ser Tyr Tyr Tyr Tyr His Gly Leu Val
145                 150                 155                 160

Pro Phe Pro Ser Glu Thr Ala Met Glu Ile Asp Val Gln Leu Pro Cys
                165                 170                 175

Met Pro Leu Leu Lys His Asp Glu Val Pro Ser Phe Leu Tyr Pro Thr
            180                 185                 190

Thr Pro Tyr Pro Phe Leu Arg Arg Ala Ile Met Gly Gln Tyr Lys Asn
        195                 200                 205

Leu Asp Lys Pro Phe Cys Ile Leu Met Asp Thr Phe Gln Glu Leu Glu
    210                 215                 220

His Glu Ile Ile Glu Tyr Met Ser Lys Ile Ser Pro Ile Lys Thr Val
225                 230                 235                 240

Gly Pro Leu Phe Lys Asn Pro Lys Ala Pro Asn Ala Thr Val Lys Gly
                245                 250                 255

Asp Phe Met Lys Ala Asp Asp Cys Val Gly Trp Leu Asp Ser Lys Pro
            260                 265                 270

Ala Ser Ser Ile Val Tyr Val Ser Phe Gly Ser Val Val Tyr Leu Lys
        275                 280                 285

Gln Asp Gln Trp Asp Glu Ile Ala Tyr Gly Leu Leu Asn Ser Gly Val
    290                 295                 300

Asn Phe Leu Trp Val Met Lys Pro Pro His Lys Asp Ser Gly Tyr Glu
305                 310                 315                 320

Val Leu Lys Met Pro Glu Gly Phe Leu Glu Lys Ala Gly Asp Arg Gly
                325                 330                 335
```

```
Lys Val Val Gln Trp Ser Pro Gln Glu Gln Val Leu Ala His Pro Ser
            340                 345                 350

Val Ala Cys Phe Val Thr His Cys Gly Trp Asn Ser Thr Met Glu Ala
            355                 360                 365

Leu Thr Ser Gly Met Pro Val Ala Phe Pro Gln Trp Gly Asp Gln
            370                 375                 380

Val Thr Asp Ala Lys Tyr Leu Val Asp Val Phe Lys Val Gly Val Arg
385                 390                 395                 400

Met Cys Arg Gly Glu Ala Glu Asn Lys Leu Ile Thr Arg Asp Val Val
                405                 410                 415

Glu Gln Cys Leu Arg Glu Ala Thr Ser Gly Pro Lys Ala Glu Glu Met
            420                 425                 430

Lys Gln Asn Ala Met Lys Trp Ser Ala Ala Glu Ala Ala Val Ala
            435                 440                 445

Glu Gly Gly Ser Ser Asp Arg Asn Ile Gln Ala Phe Val Asp Glu Val
    450                 455                 460

Lys Arg Arg Ser Leu Glu Val Leu Ala Ala Ser Gly Lys Ser Thr Ala
465                 470                 475                 480

Asn Gly Gly Ala Asp Leu Ala Asn Lys Val Ala Ala Asn Gly Val Ala
            485                 490                 495

Glu Leu Gly Glu Pro Lys Val Asn Gly Glu Leu Lys Val Val Ser
            500                 505                 510

<210> SEQ ID NO 23
<211> LENGTH: 28
<212> TYPE: DNA
<213> ORGANISM: Artificial sequence
<220> FEATURE:
<223> OTHER INFORMATION: Primer 11

<400> SEQUENCE: 23
ctcgaggtcg gtgaccatat ggggtcgg                                           28

<210> SEQ ID NO 24
<211> LENGTH: 25
<212> TYPE: DNA
<213> ORGANISM: Artificial sequence
<220> FEATURE:
<223> OTHER INFORMATION: Primer 12

<400> SEQUENCE: 24
ctcatcaagc tttcacgaca ccacc                                              25

<210> SEQ ID NO 25
<211> LENGTH: 31
<212> TYPE: DNA
<213> ORGANISM: Artificial sequence
<220> FEATURE:
<223> OTHER INFORMATION: Primer 13

<400> SEQUENCE: 25
tccaccaagc ttcgacacca cctttaactc c                                       31

<210> SEQ ID NO 26
<211> LENGTH: 1575
<212> TYPE: DNA
<213> ORGANISM: Eucalyptus grandis
<220> FEATURE:
<221> NAME/KEY: CDS
<222> LOCATION: (1)..(1575)

<400> SEQUENCE: 26
```

```
atg ggg tcg gag gca ctt gtc cac gtc ctc ttg gtc tca ttc cct ggc      48
Met Gly Ser Glu Ala Leu Val His Val Leu Leu Val Ser Phe Pro Gly
1               5                   10                  15 cag ggc cac gtc aac ccg ctc ctg agg ctt ggc aag cgc ctc gcc tcc      96
Gln Gly His Val Asn Pro Leu Leu Arg Leu Gly Lys Arg Leu Ala Ser
                20                  25                  30 aag ggc ctg ctc gtc acc ttc acg acc cca gag agc atc ggg aag gca     144
Lys Gly Leu Leu Val Thr Phe Thr Thr Pro Glu Ser Ile Gly Lys Ala
            35                  40                  45 atg cgc aag gcg agc aac atc ggc gag gag ctc tcc ccg gtc ggt gat     192
Met Arg Lys Ala Ser Asn Ile Gly Glu Glu Leu Ser Pro Val Gly Asp
    50                  55                  60 ggc ttc atc cgg ttt gag ttc ttc gag gac ggg tgg gac gag gac gag     240
Gly Phe Ile Arg Phe Glu Phe Phe Glu Asp Gly Trp Asp Glu Asp Glu
65                  70                  75                  80 ata cgc cgc cag gac ctc gac cag tac ctc ccc cag ctc gag aag gtc     288
Ile Arg Arg Gln Asp Leu Asp Gln Tyr Leu Pro Gln Leu Glu Lys Val
                85                  90                  95 ggg aag gtc ctc atc cct gag atg atc cgg cgc aac gcc gag caa ggc     336
Gly Lys Val Leu Ile Pro Glu Met Ile Arg Arg Asn Ala Glu Gln Gly
            100                 105                 110 cgc cct atc tct tgc ctc atc aac aat cct ttc atc ccc tgg gtc tcc     384
Arg Pro Ile Ser Cys Leu Ile Asn Asn Pro Phe Ile Pro Trp Val Ser
        115                 120                 125 gat gtt gcc gat agc ctc ggc ctc ccc tcg gcg atg ctc tgg gtg caa     432
Asp Val Ala Asp Ser Leu Gly Leu Pro Ser Ala Met Leu Trp Val Gln
    130                 135                 140 tcc tgt gca tgc ttc act tcg tac tac tac tac tac cat ggc ctg gtc     480
Ser Cys Ala Cys Phe Thr Ser Tyr Tyr Tyr Tyr Tyr His Gly Leu Val
145                 150                 155                 160 ccc ttc ccg tct gag aca gcg atg gag atc gat gtg caa ctc cct tgc     528
Pro Phe Pro Ser Glu Thr Ala Met Glu Ile Asp Val Gln Leu Pro Cys
                165                 170                 175 atg ccg ctc cta aag cac gac gag gtc ccg agc ttc ttg tac cca acg     576
Met Pro Leu Leu Lys His Asp Glu Val Pro Ser Phe Leu Tyr Pro Thr
            180                 185                 190 acc ccg tac cct ttc ctc cgg cgg gcg atc atg ggg cag tac aag aac     624
Thr Pro Tyr Pro Phe Leu Arg Arg Ala Ile Met Gly Gln Tyr Lys Asn
        195                 200                 205 ttg gac aag cca ttc tgc atc ctg atg gac acg ttc cag gag ctc gag     672
Leu Asp Lys Pro Phe Cys Ile Leu Met Asp Thr Phe Gln Glu Leu Glu
    210                 215                 220 cat gag atc att gag tac atg tcc aag atc agc ccc atc aag aca gtc     720
His Glu Ile Ile Glu Tyr Met Ser Lys Ile Ser Pro Ile Lys Thr Val
225                 230                 235                 240 ggg ccg ctc ttc aag aac cct aag gcc ccg aac gcc act gtc aag ggc     768
Gly Pro Leu Phe Lys Asn Pro Lys Ala Pro Asn Ala Thr Val Lys Gly
                245                 250                 255 gat ttc atg aag gct gac gac tgc gtc ggc tgg ctc gac tca aag cct     816
Asp Phe Met Lys Ala Asp Asp Cys Val Gly Trp Leu Asp Ser Lys Pro
            260                 265                 270 gct tcc tcg atc gtt tac gtg tcg ttt ggg agc gtc gtg tac ttg aag     864
Ala Ser Ser Ile Val Tyr Val Ser Phe Gly Ser Val Val Tyr Leu Lys
        275                 280                 285 caa gac cag tgg gat gag att gct tat ggg ctg ttg aac tcc ggg gtc     912
Gln Asp Gln Trp Asp Glu Ile Ala Tyr Gly Leu Leu Asn Ser Gly Val
    290                 295                 300 aac ttc ttg tgg gtc atg aag cct cca cac aag gac tct ggc tat gag     960
Asn Phe Leu Trp Val Met Lys Pro Pro His Lys Asp Ser Gly Tyr Glu
```

```
                305                 310                 315                 320
gtt ctc aaa atg cct gaa ggg ttc ttg gag aag gct ggt gat agg ggc        1008
Val Leu Lys Met Pro Glu Gly Phe Leu Glu Lys Ala Gly Asp Arg Gly
                325                 330                 335 aag gtg gtg cag tgg agc ccg caa gag caa gtc ctg gct cac ccc tcg        1056
Lys Val Val Gln Trp Ser Pro Gln Glu Gln Val Leu Ala His Pro Ser
            340                 345                 350 gtg gcc tgc ttc gtc acg cac tgc ggt tgg aac tcg acc atg gag gcc        1104
Val Ala Cys Phe Val Thr His Cys Gly Trp Asn Ser Thr Met Glu Ala
            355                 360                 365 ttg acc tct ggc atg cct gtg gtg gcg ttc ccg cag tgg ggt gac cag        1152
Leu Thr Ser Gly Met Pro Val Val Ala Phe Pro Gln Trp Gly Asp Gln
            370                 375                 380 gtc acc gac gcc aag tac cta gtc gac gtg ttc aag gtc ggg gtg agg        1200
Val Thr Asp Ala Lys Tyr Leu Val Asp Val Phe Lys Val Gly Val Arg
385                 390                 395                 400 atg tgc cgg ggc gag gca gag aac aag ctg atc acg cgg gac gtg gtc        1248
Met Cys Arg Gly Glu Ala Glu Asn Lys Leu Ile Thr Arg Asp Val Val
                405                 410                 415 gag cag tgc ctc cgc gag gca acc tcg ggg ccc aag gcc gag gag atg        1296
Glu Gln Cys Leu Arg Glu Ala Thr Ser Gly Pro Lys Ala Glu Glu Met
                420                 425                 430 aag cag aac gcg atg aag tgg agc gcg gca gcg gag gcg gct gtg gca        1344
Lys Gln Asn Ala Met Lys Trp Ser Ala Ala Ala Glu Ala Ala Val Ala
                435                 440                 445 gag ggt ggc tcc tca gac cgg aac atc cag gcc ttc gtg gac gag gtg        1392
Glu Gly Gly Ser Ser Asp Arg Asn Ile Gln Ala Phe Val Asp Glu Val
        450                 455                 460 aag agg agg agc ctg gag gtg ctg gct gcg agt ggc aag tca acg gcc        1440
Lys Arg Arg Ser Leu Glu Val Leu Ala Ala Ser Gly Lys Ser Thr Ala
465                 470                 475                 480 aac gga ggg gcg gac ttg gcc aac aaa gtg gcg gcc aat ggg gtt gcg        1488
Asn Gly Gly Ala Asp Leu Ala Asn Lys Val Ala Ala Asn Gly Val Ala
                485                 490                 495 gag ctg ggc gag cca aag gtc aac ggg gag tta aag gtg gtg tcg aag        1536
Glu Leu Gly Glu Pro Lys Val Asn Gly Glu Leu Lys Val Val Ser Lys
            500                 505                 510 ctt gcg gcc gca ctc gag cac cac cac cac cac cac tga                    1575
Leu Ala Ala Ala Leu Glu His His His His His His
            515                 520

<210> SEQ ID NO 27
<211> LENGTH: 524
<212> TYPE: PRT
<213> ORGANISM: Eucalyptus grandis

<400> SEQUENCE: 27

Met Gly Ser Glu Ala Leu Val His Val Leu Leu Val Ser Phe Pro Gly
1               5                   10                  15

Gln Gly His Val Asn Pro Leu Leu Arg Leu Gly Lys Arg Leu Ala Ser
                20                  25                  30

Lys Gly Leu Leu Val Thr Phe Thr Thr Pro Glu Ser Ile Gly Lys Ala
            35                  40                  45

Met Arg Lys Ala Ser Asn Ile Gly Glu Glu Leu Ser Pro Val Gly Asp
        50                  55                  60

Gly Phe Ile Arg Phe Glu Phe Phe Glu Asp Gly Trp Asp Glu Asp Glu
65                  70                  75                  80

Ile Arg Arg Gln Asp Leu Asp Gln Tyr Leu Pro Gln Leu Glu Lys Val
                85                  90                  95
```

```
Gly Lys Val Leu Ile Pro Glu Met Ile Arg Arg Asn Ala Glu Gln Gly
            100                 105                 110

Arg Pro Ile Ser Cys Leu Ile Asn Asn Pro Phe Ile Pro Trp Val Ser
            115                 120                 125

Asp Val Ala Asp Ser Leu Gly Leu Pro Ser Ala Met Leu Trp Val Gln
            130                 135                 140

Ser Cys Ala Cys Phe Thr Ser Tyr Tyr Tyr Tyr His Gly Leu Val
145                 150                 155                 160

Pro Phe Pro Ser Glu Thr Ala Met Glu Ile Asp Val Gln Leu Pro Cys
            165                 170                 175

Met Pro Leu Leu Lys His Asp Glu Val Pro Ser Phe Leu Tyr Pro Thr
            180                 185                 190

Thr Pro Tyr Pro Phe Leu Arg Arg Ala Ile Met Gly Gln Tyr Lys Asn
            195                 200                 205

Leu Asp Lys Pro Phe Cys Ile Leu Met Asp Thr Phe Gln Glu Leu Glu
210                 215                 220

His Glu Ile Ile Glu Tyr Met Ser Lys Ile Ser Pro Ile Lys Thr Val
225                 230                 235                 240

Gly Pro Leu Phe Lys Asn Pro Lys Ala Pro Asn Ala Thr Val Lys Gly
            245                 250                 255

Asp Phe Met Lys Ala Asp Asp Cys Val Gly Trp Leu Asp Ser Lys Pro
            260                 265                 270

Ala Ser Ser Ile Val Tyr Val Ser Phe Gly Ser Val Val Tyr Leu Lys
            275                 280                 285

Gln Asp Gln Trp Asp Glu Ile Ala Tyr Gly Leu Leu Asn Ser Gly Val
            290                 295                 300

Asn Phe Leu Trp Val Met Lys Pro Pro His Lys Asp Ser Gly Tyr Glu
305                 310                 315                 320

Val Leu Lys Met Pro Glu Gly Phe Leu Glu Lys Ala Gly Asp Arg Gly
            325                 330                 335

Lys Val Val Gln Trp Ser Pro Gln Glu Gln Val Leu Ala His Pro Ser
            340                 345                 350

Val Ala Cys Phe Val Thr His Cys Gly Trp Asn Ser Thr Met Glu Ala
            355                 360                 365

Leu Thr Ser Gly Met Pro Val Val Ala Phe Pro Gln Trp Gly Asp Gln
            370                 375                 380

Val Thr Asp Ala Lys Tyr Leu Val Asp Val Phe Lys Val Gly Val Arg
385                 390                 395                 400

Met Cys Arg Gly Glu Ala Glu Asn Lys Leu Ile Thr Arg Asp Val Val
            405                 410                 415

Glu Gln Cys Leu Arg Glu Ala Thr Ser Gly Pro Lys Ala Glu Glu Met
            420                 425                 430

Lys Gln Asn Ala Met Lys Trp Ser Ala Ala Glu Ala Ala Val Ala
            435                 440                 445

Glu Gly Gly Ser Ser Asp Arg Asn Ile Gln Ala Phe Val Asp Glu Val
            450                 455                 460

Lys Arg Arg Ser Leu Glu Val Leu Ala Ala Ser Gly Lys Ser Thr Ala
465                 470                 475                 480

Asn Gly Gly Ala Asp Leu Ala Asn Lys Val Ala Ala Asn Gly Val Ala
            485                 490                 495

Glu Leu Gly Glu Pro Lys Val Asn Gly Glu Leu Lys Val Val Ser Lys
            500                 505                 510
```

```
Leu Ala Ala Ala Leu Glu His His His His His His
        515                 520
```

<210> SEQ ID NO 28
<211> LENGTH: 28
<212> TYPE: DNA
<213> ORGANISM: Artificial sequence
<220> FEATURE:
<223> OTHER INFORMATION: Primer 14

<400> SEQUENCE: 28
cattcgagac atatgggaac tgaatctc                                          28

<210> SEQ ID NO 29
<211> LENGTH: 26
<212> TYPE: DNA
<213> ORGANISM: Artificial sequence
<220> FEATURE:
<223> OTHER INFORMATION: Primer 15

<400> SEQUENCE: 29
gtcagaactt cgtcgacata ctgtac                                            26

<210> SEQ ID NO 30
<211> LENGTH: 1515
<212> TYPE: DNA
<213> ORGANISM: Citrus mitis
<220> FEATURE:
<221> NAME/KEY: CDS
<222> LOCATION: (1)..(1515)

<400> SEQUENCE: 30

```
atg gga act gaa tct ctt gtt cac gtc tta cta gtt tca ttc ccc ggc        48
Met Gly Thr Glu Ser Leu Val His Val Leu Leu Val Ser Phe Pro Gly
1               5                   10                  15 cat ggc cac gta aac ccg ctt ctg agg ctc ggc aga ctc ctt gct tca        96
His Gly His Val Asn Pro Leu Leu Arg Leu Gly Arg Leu Leu Ala Ser
                20                  25                  30 aag ggt ttc ttt ctc acc ttg acc aca cct gaa agc ttt ggc aaa caa       144
Lys Gly Phe Phe Leu Thr Leu Thr Thr Pro Glu Ser Phe Gly Lys Gln
            35                  40                  45 atg aga aaa gcg ggt aac ttc acc tac gag cct act cca gtt ggc gac       192
Met Arg Lys Ala Gly Asn Phe Thr Tyr Glu Pro Thr Pro Val Gly Asp
        50                  55                  60 ggc ttc att cgc ttc gaa ttc ttc gag gat gga tgg gac gaa gac gat       240
Gly Phe Ile Arg Phe Glu Phe Phe Glu Asp Gly Trp Asp Glu Asp Asp
65                  70                  75                  80 cca gga cgc cga gat ctt gac caa tac atg gct caa ctt gag ctt att       288
Pro Gly Arg Arg Asp Leu Asp Gln Tyr Met Ala Gln Leu Glu Leu Ile
                85                  90                  95 ggc aaa caa gtg att cca aaa ata atc aag aaa agc gct gaa gaa tat       336
Gly Lys Gln Val Ile Pro Lys Ile Ile Lys Lys Ser Ala Glu Glu Tyr
                100                 105                 110 cgc ccc gtt tct tgc ctg atc aat aac cca ttt atc cct tgg gtt tcc       384
Arg Pro Val Ser Cys Leu Ile Asn Asn Pro Phe Ile Pro Trp Val Ser
            115                 120                 125 gat gtt gct gaa tcc cta ggg ctt ccg tct gct atg ctt tgg gtt caa       432
Asp Val Ala Glu Ser Leu Gly Leu Pro Ser Ala Met Leu Trp Val Gln
        130                 135                 140 tct tgt gct tgt ttt gct gct tat tac cat tac ttt cac ggt ttg gtt       480
Ser Cys Ala Cys Phe Ala Ala Tyr Tyr His Tyr Phe His Gly Leu Val
145                 150                 155                 160 cca ttt cct agt gaa aaa gaa ccc gaa att gat gtt cag ttg ccg tgc       528
```

-continued

```
                Pro Phe Pro Ser Glu Lys Glu Pro Glu Ile Asp Val Gln Leu Pro Cys
                                165                 170                 175 atg cca cta ctg aag cat gat gaa gtg cct agc ttc ttg cat ccg tca        576
Met Pro Leu Leu Lys His Asp Glu Val Pro Ser Phe Leu His Pro Ser
        180                 185                 190 act cct tat cct ttc ttg aga aga gct att ttg ggg cag tac gaa aat        624
Thr Pro Tyr Pro Phe Leu Arg Arg Ala Ile Leu Gly Gln Tyr Glu Asn
            195                 200                 205 ctt ggc aag ccg ttt tgc ata ttg ttg gac act ttc tat gag ctt gag        672
Leu Gly Lys Pro Phe Cys Ile Leu Leu Asp Thr Phe Tyr Glu Leu Glu
        210                 215                 220 aaa gag att atc gat tac atg gca aaa att tgc cct att aaa ccc gtc        720
Lys Glu Ile Ile Asp Tyr Met Ala Lys Ile Cys Pro Ile Lys Pro Val
225                 230                 235                 240 ggc cct ctg ttc aaa aac cct aaa gct cca acc tta acc gtc cgc gat        768
Gly Pro Leu Phe Lys Asn Pro Lys Ala Pro Thr Leu Thr Val Arg Asp
            245                 250                 255 gac tgc atg aaa ccc gat gaa tgc ata gac tgg ctc gac aaa aag cca        816
Asp Cys Met Lys Pro Asp Glu Cys Ile Asp Trp Leu Asp Lys Lys Pro
        260                 265                 270 cca tca tcc gtt gta tac atc tct ttc ggc acg gtt gtc tac ttg aag        864
Pro Ser Ser Val Val Tyr Ile Ser Phe Gly Thr Val Val Tyr Leu Lys
            275                 280                 285 caa gaa caa gtt gaa gaa att ggc tat gca ttg ttg aac tcg ggg att        912
Gln Glu Gln Val Glu Glu Ile Gly Tyr Ala Leu Leu Asn Ser Gly Ile
        290                 295                 300 tcg ttc ttg tgg gtg atg aag ccg ccg cct gaa gac tct ggc gtt aaa        960
Ser Phe Leu Trp Val Met Lys Pro Pro Pro Glu Asp Ser Gly Val Lys
305                 310                 315                 320 att gtt gac ctg cca gat ggg ttc ttg gag aaa gtt gga gat aag ggc       1008
Ile Val Asp Leu Pro Asp Gly Phe Leu Glu Lys Val Gly Asp Lys Gly
            325                 330                 335 aaa gtt gtg caa tgg agt cca caa gaa aaa gtg ttg gct cac cct agt       1056
Lys Val Val Gln Trp Ser Pro Gln Glu Lys Val Leu Ala His Pro Ser
        340                 345                 350 gtt gct tgc ttt gtg act cac tgc ggc tgg aac tca acc atg gag tcg       1104
Val Ala Cys Phe Val Thr His Cys Gly Trp Asn Ser Thr Met Glu Ser
            355                 360                 365 ttg gca tcg ggg gtg ccg gtg atc acc ttc ccg caa tgg ggt gat caa       1152
Leu Ala Ser Gly Val Pro Val Ile Thr Phe Pro Gln Trp Gly Asp Gln
        370                 375                 380 gta act gat gcc atg tat ttg tgt gat gtg ttc aag acc ggt tta aga       1200
Val Thr Asp Ala Met Tyr Leu Cys Asp Val Phe Lys Thr Gly Leu Arg
385                 390                 395                 400 ttg tgc cgt gga gag gca gag aac agg ata att tca agg gat gaa gtg       1248
Leu Cys Arg Gly Glu Ala Glu Asn Arg Ile Ile Ser Arg Asp Glu Val
            405                 410                 415 gag aag tgc ttg ctc gag gcc acg gcc gga cct aag gcg gcg gag ctg       1296
Glu Lys Cys Leu Leu Glu Ala Thr Ala Gly Pro Lys Ala Ala Glu Leu
        420                 425                 430 aag gag agc gcg ctg aag tgg aag cag gag gcg gag gaa gct gtg gcc       1344
Lys Glu Ser Ala Leu Lys Trp Lys Gln Glu Ala Glu Glu Ala Val Ala
            435                 440                 445 gat ggt ggc tcg tcg gat agg aac att cag gct ttc gtt gat gaa gta       1392
Asp Gly Gly Ser Ser Asp Arg Asn Ile Gln Ala Phe Val Asp Glu Val
        450                 455                 460 aga agg aga agt gtg ggg att ata acc agc agc aag tcg aag tca atc       1440
Arg Arg Arg Ser Val Gly Ile Ile Thr Ser Ser Lys Ser Lys Ser Ile
465                 470                 475                 480
```

```
cac aga gtt aag gaa tta gtg gag aag acg gca acg gca act gca aat    1488
His Arg Val Lys Glu Leu Val Glu Lys Thr Ala Thr Ala Thr Ala Asn
            485                 490                 495 gac aag gta gaa ttg gtg gag tca tga                                1515
Asp Lys Val Glu Leu Val Glu Ser
            500
```

<210> SEQ ID NO 31
<211> LENGTH: 504
<212> TYPE: PRT
<213> ORGANISM: Citrus mitis

<400> SEQUENCE: 31

```
Met Gly Thr Glu Ser Leu Val His Val Leu Val Ser Phe Pro Gly
1               5                  10                  15

His Gly His Val Asn Pro Leu Leu Arg Leu Gly Arg Leu Leu Ala Ser
                20                  25                  30

Lys Gly Phe Phe Leu Thr Leu Thr Thr Pro Glu Ser Phe Gly Lys Gln
            35                  40                  45

Met Arg Lys Ala Gly Asn Phe Thr Tyr Glu Pro Thr Pro Val Gly Asp
    50                  55                  60

Gly Phe Ile Arg Phe Glu Phe Phe Glu Asp Gly Trp Asp Glu Asp
65                  70                  75                  80

Pro Gly Arg Arg Asp Leu Asp Gln Tyr Met Ala Gln Leu Glu Leu Ile
                85                  90                  95

Gly Lys Gln Val Ile Pro Lys Ile Ile Lys Ser Ala Glu Glu Tyr
            100                 105                 110

Arg Pro Val Ser Cys Leu Ile Asn Asn Pro Phe Ile Pro Trp Val Ser
        115                 120                 125

Asp Val Ala Glu Ser Leu Gly Leu Pro Ser Ala Met Leu Trp Val Gln
    130                 135                 140

Ser Cys Ala Cys Phe Ala Ala Tyr Tyr His Tyr Phe His Gly Leu Val
145                 150                 155                 160

Pro Phe Pro Ser Glu Lys Glu Pro Glu Ile Asp Val Gln Leu Pro Cys
                165                 170                 175

Met Pro Leu Leu Lys His Asp Glu Val Pro Ser Phe Leu His Pro Ser
            180                 185                 190

Thr Pro Tyr Pro Phe Leu Arg Arg Ala Ile Leu Gly Gln Tyr Glu Asn
        195                 200                 205

Leu Gly Lys Pro Phe Cys Ile Leu Leu Asp Thr Phe Tyr Glu Leu Glu
    210                 215                 220

Lys Glu Ile Ile Asp Tyr Met Ala Lys Ile Cys Pro Ile Lys Pro Val
225                 230                 235                 240

Gly Pro Leu Phe Lys Asn Pro Lys Ala Pro Thr Leu Thr Val Arg Asp
                245                 250                 255

Asp Cys Met Lys Pro Asp Glu Cys Ile Asp Trp Leu Asp Lys Pro
            260                 265                 270

Pro Ser Ser Val Val Tyr Ile Ser Phe Gly Thr Val Val Tyr Leu Lys
        275                 280                 285

Gln Glu Gln Val Glu Glu Ile Gly Tyr Ala Leu Leu Asn Ser Gly Ile
    290                 295                 300

Ser Phe Leu Trp Val Met Lys Pro Pro Glu Asp Ser Gly Val Lys
305                 310                 315                 320

Ile Val Asp Leu Pro Asp Gly Phe Leu Glu Lys Val Gly Asp Lys Gly
                325                 330                 335
```

```
Lys Val Val Gln Trp Ser Pro Gln Glu Lys Val Leu Ala His Pro Ser
            340                 345                 350

Val Ala Cys Phe Val Thr His Cys Gly Trp Asn Ser Thr Met Glu Ser
            355                 360                 365

Leu Ala Ser Gly Val Pro Val Ile Thr Phe Pro Gln Trp Gly Asp Gln
            370                 375                 380

Val Thr Asp Ala Met Tyr Leu Cys Asp Val Phe Lys Thr Gly Leu Arg
385                 390                 395                 400

Leu Cys Arg Gly Glu Ala Glu Asn Arg Ile Ile Ser Arg Asp Glu Val
            405                 410                 415

Glu Lys Cys Leu Leu Glu Ala Thr Gly Pro Lys Ala Ala Glu Leu
            420                 425                 430

Lys Glu Ser Ala Leu Lys Trp Lys Gln Glu Ala Glu Glu Ala Val Ala
            435                 440                 445

Asp Gly Gly Ser Ser Asp Arg Asn Ile Gln Ala Phe Val Asp Glu Val
            450                 455                 460

Arg Arg Arg Ser Val Gly Ile Ile Thr Ser Ser Lys Ser Lys Ser Ile
465                 470                 475                 480

His Arg Val Lys Glu Leu Val Glu Lys Thr Ala Thr Ala Thr Ala Asn
            485                 490                 495

Asp Lys Val Glu Leu Val Glu Ser
            500
```

<210> SEQ ID NO 32
<211> LENGTH: 29
<212> TYPE: DNA
<213> ORGANISM: Artificial sequence
<220> FEATURE:
<223> OTHER INFORMATION: Primer 16

<400> SEQUENCE: 32
ctggtccggt cgactgactc caccaattc                                 29

<210> SEQ ID NO 33
<211> LENGTH: 1560
<212> TYPE: DNA
<213> ORGANISM: Citrus mitis
<220> FEATURE:
<221> NAME/KEY: CDS
<222> LOCATION: (1)..(1560)

<400> SEQUENCE: 33

```
atg gga act gaa tct ctt gtt cac gtc tta cta gtt tca ttc ccc ggc      48
Met Gly Thr Glu Ser Leu Val His Val Leu Leu Val Ser Phe Pro Gly
1               5                   10                  15 cat ggc cac gta aac ccg ctt ctg agg ctc ggc aga ctc ctt gct tca      96
His Gly His Val Asn Pro Leu Leu Arg Leu Gly Arg Leu Leu Ala Ser
                20                  25                  30 aag ggt ttc ttt ctc acc ttg acc aca cct gaa agc ttt ggc aaa caa     144
Lys Gly Phe Phe Leu Thr Leu Thr Thr Pro Glu Ser Phe Gly Lys Gln
            35                  40                  45 atg aga aaa gcg ggt aac ttc acc tac gag cct act cca gtt ggc gac     192
Met Arg Lys Ala Gly Asn Phe Thr Tyr Glu Pro Thr Pro Val Gly Asp
        50                  55                  60 ggc ttc att cgc ttc gaa ttc ttc gag gat gga tgg gac gaa gac gat     240
Gly Phe Ile Arg Phe Glu Phe Phe Glu Asp Gly Trp Asp Glu Asp Asp
65                  70                  75                  80 cca gga cgc cga gat ctt gac caa tac atg gct caa ctt gag ctt att     288
Pro Gly Arg Arg Asp Leu Asp Gln Tyr Met Ala Gln Leu Glu Leu Ile
                85                  90                  95
```

-continued

| | |
|---|---|
| ggc aaa caa gtg att cca aaa ata atc aag aaa agc gct gaa gaa tat<br>Gly Lys Gln Val Ile Pro Lys Ile Ile Lys Lys Ser Ala Glu Glu Tyr<br>100              105              110 | 336 |
| cgc ccc gtt tct tgc ctg atc aat aac cca ttt atc cct tgg gtt tcc<br>Arg Pro Val Ser Cys Leu Ile Asn Asn Pro Phe Ile Pro Trp Val Ser<br>115              120              125 | 384 |
| gat gtt gct gaa tcc cta ggg ctt ccg tct gct atg ctt tgg gtt caa<br>Asp Val Ala Glu Ser Leu Gly Leu Pro Ser Ala Met Leu Trp Val Gln<br>130              135              140 | 432 |
| tct tgt gct tgt ttt gct gct tat tac cat tac ttt cac ggt ttg gtt<br>Ser Cys Ala Cys Phe Ala Ala Tyr Tyr His Tyr Phe His Gly Leu Val<br>145              150              155              160 | 480 |
| cca ttt cct agt gaa aaa gaa ccc gaa att gat gtt cag ttg ccg tgc<br>Pro Phe Pro Ser Glu Lys Glu Pro Glu Ile Asp Val Gln Leu Pro Cys<br>165              170              175 | 528 |
| atg cca cta ctg aag cat gat gaa gtg cct agc ttc ttg cat ccg tca<br>Met Pro Leu Leu Lys His Asp Glu Val Pro Ser Phe Leu His Pro Ser<br>180              185              190 | 576 |
| act cct tat cct ttc ttg aga aga gct att ttg ggg cag tac gaa aat<br>Thr Pro Tyr Pro Phe Leu Arg Arg Ala Ile Leu Gly Gln Tyr Glu Asn<br>195              200              205 | 624 |
| ctt ggc aag ccg ttt tgc ata ttg ttg gac act ttc tat gag ctt gag<br>Leu Gly Lys Pro Phe Cys Ile Leu Leu Asp Thr Phe Tyr Glu Leu Glu<br>210              215              220 | 672 |
| aaa gag att atc gat tac atg gca caa att tgc cct att aaa ccc gtc<br>Lys Glu Ile Ile Asp Tyr Met Ala Gln Ile Cys Pro Ile Lys Pro Val<br>225              230              235              240 | 720 |
| ggc cct ctg ttc aaa aac cct aaa gct cca acc tta acc gtc cgc gat<br>Gly Pro Leu Phe Lys Asn Pro Lys Ala Pro Thr Leu Thr Val Arg Asp<br>245              250              255 | 768 |
| gac tgc atg aaa ccc gat gaa tgc ata gac tgg ctc gac aaa aag cca<br>Asp Cys Met Lys Pro Asp Glu Cys Ile Asp Trp Leu Asp Lys Lys Pro<br>260              265              270 | 816 |
| cca tca tcc gtt gta tac atc tct ttc ggc acg gtt gtc tac ttg aag<br>Pro Ser Ser Val Val Tyr Ile Ser Phe Gly Thr Val Val Tyr Leu Lys<br>275              280              285 | 864 |
| caa gaa caa gtt gaa gaa att ggc tat gca ttg ttg aac tcg ggg att<br>Gln Glu Gln Val Glu Glu Ile Gly Tyr Ala Leu Leu Asn Ser Gly Ile<br>290              295              300 | 912 |
| tcg ttc ttg tgg gtg atg aag ccg ccg cct gaa gac tct ggc gtt aaa<br>Ser Phe Leu Trp Val Met Lys Pro Pro Pro Glu Asp Ser Gly Val Lys<br>305              310              315              320 | 960 |
| att gtt gac ccg cca gat ggg ttc ttg gag aaa gtt gga gat aag ggc<br>Ile Val Asp Pro Pro Asp Gly Phe Leu Glu Lys Val Gly Asp Lys Gly<br>325              330              335 | 1008 |
| aaa gtt gtg caa tgg agt cca caa gaa aaa gtg ttg gct cac cct agt<br>Lys Val Val Gln Trp Ser Pro Gln Glu Lys Val Leu Ala His Pro Ser<br>340              345              350 | 1056 |
| gtt gct tgc ttt gtg act cac tgc ggc tgg aac tca acc atg gag tcg<br>Val Ala Cys Phe Val Thr His Cys Gly Trp Asn Ser Thr Met Glu Ser<br>355              360              365 | 1104 |
| ttg gca tcg ggg gtg ccg gtg atc acc ttc ccg caa tgg ggt gat caa<br>Leu Ala Ser Gly Val Pro Val Ile Thr Phe Pro Gln Trp Gly Asp Gln<br>370              375              380 | 1152 |
| gta act gat gcc atg tat ttg tgt gat gtg ttc aag acc ggt tta aga<br>Val Thr Asp Ala Met Tyr Leu Cys Asp Val Phe Lys Thr Gly Leu Arg<br>385              390              395              400 | 1200 |
| ttg tgc cgt gga gag gca gag aac agg ata att tca agg gat gaa gtg<br>Leu Cys Arg Gly Glu Ala Glu Asn Arg Ile Ile Ser Arg Asp Glu Val | 1248 |

```
                             405                 410                 415
gag aag tgc ttg ctc gag gcc acg gcc gga cct aag gcg gcg gag ctg           1296
Glu Lys Cys Leu Leu Glu Ala Thr Ala Gly Pro Lys Ala Ala Glu Leu
            420                 425                 430 aag gag agc gcg ctg aag tgg aag cag gag gcg gag gaa gct gtg gcc           1344
Lys Glu Ser Ala Leu Lys Trp Lys Gln Glu Ala Glu Glu Ala Val Ala
        435                 440                 445 gat ggt ggc tcg tcg gat agg aac att cag gct ttc gtt gat gaa gta           1392
Asp Gly Gly Ser Ser Asp Arg Asn Ile Gln Ala Phe Val Asp Glu Val
    450                 455                 460 aga agg aga agt gtg ggg att ata acc agc agc aag tcg aag tca atc           1440
Arg Arg Arg Ser Val Gly Ile Ile Thr Ser Ser Lys Ser Lys Ser Ile
465                 470                 475                 480 cac aga gtt aag gaa tta gtg gag aag acg gca acg gca act gca aat           1488
His Arg Val Lys Glu Leu Val Glu Lys Thr Ala Thr Ala Thr Ala Asn
                485                 490                 495 gac aag gta gaa ttg gtg gag tca gtc gac aag ctt gcg gcc gca ctc           1536
Asp Lys Val Glu Leu Val Glu Ser Val Asp Lys Leu Ala Ala Ala Leu
            500                 505                 510 gag cac cac cac cac cac cac tga                                           1560
Glu His His His His His His
        515

<210> SEQ ID NO 34
<211> LENGTH: 519
<212> TYPE: PRT
<213> ORGANISM: Citrus mitis

<400> SEQUENCE: 34

Met Gly Thr Glu Ser Leu Val His Val Leu Val Ser Phe Pro Gly
1               5                   10                  15

His Gly His Val Asn Pro Leu Leu Arg Leu Gly Arg Leu Leu Ala Ser
                20                  25                  30

Lys Gly Phe Phe Leu Thr Leu Thr Thr Pro Glu Ser Phe Gly Lys Gln
            35                  40                  45

Met Arg Lys Ala Gly Asn Phe Thr Tyr Glu Pro Thr Pro Val Gly Asp
        50                  55                  60

Gly Phe Ile Arg Phe Glu Phe Glu Asp Gly Trp Asp Glu Asp
65                  70                  75                  80

Pro Gly Arg Arg Asp Leu Asp Gln Tyr Met Ala Gln Leu Glu Leu Ile
                85                  90                  95

Gly Lys Gln Val Ile Pro Lys Ile Ile Lys Lys Ser Ala Glu Glu Tyr
            100                 105                 110

Arg Pro Val Ser Cys Leu Ile Asn Asn Pro Phe Ile Pro Trp Val Ser
        115                 120                 125

Asp Val Ala Glu Ser Leu Gly Leu Pro Ser Ala Met Leu Trp Val Gln
    130                 135                 140

Ser Cys Ala Cys Phe Ala Ala Tyr Tyr His Tyr Phe His Gly Leu Val
145                 150                 155                 160

Pro Phe Pro Ser Glu Lys Glu Pro Glu Ile Asp Val Gln Leu Pro Cys
                165                 170                 175

Met Pro Leu Leu Lys His Asp Glu Val Pro Ser Phe Leu His Pro Ser
            180                 185                 190

Thr Pro Tyr Pro Phe Leu Arg Arg Ala Ile Leu Gly Gln Tyr Glu Asn
        195                 200                 205

Leu Gly Lys Pro Phe Cys Ile Leu Leu Asp Thr Phe Tyr Glu Leu Glu
    210                 215                 220
```

```
Lys Glu Ile Ile Asp Tyr Met Ala Gln Ile Cys Pro Ile Lys Pro Val
225                 230                 235                 240

Gly Pro Leu Phe Lys Asn Pro Lys Ala Pro Thr Leu Thr Val Arg Asp
            245                 250                 255

Asp Cys Met Lys Pro Asp Glu Cys Ile Asp Trp Leu Asp Lys Lys Pro
        260                 265                 270

Pro Ser Ser Val Val Tyr Ile Ser Phe Gly Thr Val Val Tyr Leu Lys
    275                 280                 285

Gln Glu Gln Val Glu Glu Ile Gly Tyr Ala Leu Leu Asn Ser Gly Ile
290                 295                 300

Ser Phe Leu Trp Val Met Lys Pro Pro Glu Asp Ser Gly Val Lys
305             310                 315                 320

Ile Val Asp Pro Pro Asp Gly Phe Leu Glu Lys Val Gly Asp Lys Gly
                325                 330                 335

Lys Val Val Gln Trp Ser Pro Gln Glu Lys Val Leu Ala His Pro Ser
            340                 345                 350

Val Ala Cys Phe Val Thr His Cys Gly Trp Asn Ser Thr Met Glu Ser
        355                 360                 365

Leu Ala Ser Gly Val Pro Val Ile Thr Phe Pro Gln Trp Gly Asp Gln
    370                 375                 380

Val Thr Asp Ala Met Tyr Leu Cys Asp Val Phe Lys Thr Gly Leu Arg
385                 390                 395                 400

Leu Cys Arg Gly Glu Ala Glu Asn Arg Ile Ile Ser Arg Asp Glu Val
                405                 410                 415

Glu Lys Cys Leu Leu Glu Ala Thr Ala Gly Pro Lys Ala Ala Glu Leu
            420                 425                 430

Lys Glu Ser Ala Leu Lys Trp Lys Gln Glu Ala Glu Ala Val Ala
        435                 440                 445

Asp Gly Gly Ser Ser Asp Arg Asn Ile Gln Ala Phe Val Asp Glu Val
    450                 455                 460

Arg Arg Arg Ser Val Gly Ile Ile Thr Ser Ser Lys Ser Lys Ser Ile
465                 470                 475                 480

His Arg Val Lys Glu Leu Val Glu Lys Thr Ala Thr Ala Thr Ala Asn
                485                 490                 495

Asp Lys Val Glu Leu Val Glu Ser Val Asp Lys Leu Ala Ala Ala Leu
            500                 505                 510

Glu His His His His His His
        515

<210> SEQ ID NO 35
<211> LENGTH: 32
<212> TYPE: DNA
<213> ORGANISM: Artificial sequence
<220> FEATURE:
<223> OTHER INFORMATION: Primer 17

<400> SEQUENCE: 35
ctactcattt catatgtcac accccgcgtt aa                              32

<210> SEQ ID NO 36
<211> LENGTH: 34
<212> TYPE: DNA
<213> ORGANISM: Artificial sequence
<220> FEATURE:
<223> OTHER INFORMATION: Primer 18

<400> SEQUENCE: 36
```

-continued catcttacta gatctttagt acaacggtga cgcc    34

<210> SEQ ID NO 37
<211> LENGTH: 495
<212> TYPE: DNA
<213> ORGANISM: Escherichia coli
<220> FEATURE:
<221> NAME/KEY: CDS
<222> LOCATION: (1)..(495)

<400> SEQUENCE: 37

| atg | tca | cac | ccc | gcg | tta | acg | caa | ctg | cgt | gcg | ctg | cgc | tat | tgt | aaa | 48 |
| Met | Ser | His | Pro | Ala | Leu | Thr | Gln | Leu | Arg | Ala | Leu | Arg | Tyr | Cys | Lys | |
| 1 | | | | 5 | | | | | 10 | | | | | 15 | | |

| gag | atc | cct | gcc | ctg | gat | ccg | caa | ctg | ctc | gac | tgg | ctg | ttg | ctg | gag | 96 |
| Glu | Ile | Pro | Ala | Leu | Asp | Pro | Gln | Leu | Leu | Asp | Trp | Leu | Leu | Leu | Glu | |
| | | | 20 | | | | | 25 | | | | | 30 | | | |

| gat | tcc | atg | aca | aaa | cgt | ttt | gaa | cag | cag | gga | aaa | acg | gta | agc | gtg | 144 |
| Asp | Ser | Met | Thr | Lys | Arg | Phe | Glu | Gln | Gln | Gly | Lys | Thr | Val | Ser | Val | |
| | | 35 | | | | | 40 | | | | | 45 | | | | |

| acg | atg | atc | cgc | gaa | ggg | ttt | gtc | gag | cag | aat | gaa | atc | ccc | gaa | gaa | 192 |
| Thr | Met | Ile | Arg | Glu | Gly | Phe | Val | Glu | Gln | Asn | Glu | Ile | Pro | Glu | Glu | |
| 50 | | | | | 55 | | | | | 60 | | | | | | |

| ctg | ccg | ctg | ctg | ccg | aaa | gag | tct | cgt | tac | tgg | tta | cgt | gaa | att | ttg | 240 |
| Leu | Pro | Leu | Leu | Pro | Lys | Glu | Ser | Arg | Tyr | Trp | Leu | Arg | Glu | Ile | Leu | |
| 65 | | | | | 70 | | | | | 75 | | | | | 80 | |

| tta | tgt | gcc | gat | ggt | gaa | ccg | tgg | ctt | gcc | ggt | cgt | acc | gtc | gtt | cct | 288 |
| Leu | Cys | Ala | Asp | Gly | Glu | Pro | Trp | Leu | Ala | Gly | Arg | Thr | Val | Val | Pro | |
| | | | | 85 | | | | | 90 | | | | | 95 | | |

| gtg | tca | acg | tta | agc | ggg | ccg | gag | ctg | gcg | tta | caa | aaa | ttg | ggt | aaa | 336 |
| Val | Ser | Thr | Leu | Ser | Gly | Pro | Glu | Leu | Ala | Leu | Gln | Lys | Leu | Gly | Lys | |
| | | | 100 | | | | | 105 | | | | | 110 | | | |

| acg | ccg | tta | gga | cgc | tat | ctg | ttc | aca | tca | tcg | aca | tta | acc | cgg | gac | 384 |
| Thr | Pro | Leu | Gly | Arg | Tyr | Leu | Phe | Thr | Ser | Ser | Thr | Leu | Thr | Arg | Asp | |
| | | 115 | | | | | 120 | | | | | 125 | | | | |

| ttt | att | gag | ata | ggc | cgt | gat | gcc | ggg | ctg | tgg | ggg | cga | cgt | tcc | cgc | 432 |
| Phe | Ile | Glu | Ile | Gly | Arg | Asp | Ala | Gly | Leu | Trp | Gly | Arg | Arg | Ser | Arg | |
| | | 130 | | | | | 135 | | | | | 140 | | | | |

| ctg | cga | tta | agc | ggt | aaa | ccg | ctg | tta | cta | aca | gaa | ctg | ttt | tta | ccg | 480 |
| Leu | Arg | Leu | Ser | Gly | Lys | Pro | Leu | Leu | Leu | Thr | Glu | Leu | Phe | Leu | Pro | |
| 145 | | | | | 150 | | | | | 155 | | | | | 160 | |

| gcg | tca | ccg | ttg | tac | | | | | | | | | | | | 495 |
| Ala | Ser | Pro | Leu | Tyr | | | | | | | | | | | | |
| | | | | 165 | | | | | | | | | | | | |

<210> SEQ ID NO 38
<211> LENGTH: 165
<212> TYPE: PRT
<213> ORGANISM: Escherichia coli

<400> SEQUENCE: 38

Met Ser His Pro Ala Leu Thr Gln Leu Arg Ala Leu Arg Tyr Cys Lys
1               5                   10                  15

Glu Ile Pro Ala Leu Asp Pro Gln Leu Leu Asp Trp Leu Leu Leu Glu
            20                  25                  30

Asp Ser Met Thr Lys Arg Phe Glu Gln Gln Gly Lys Thr Val Ser Val
        35                  40                  45

Thr Met Ile Arg Glu Gly Phe Val Glu Gln Asn Glu Ile Pro Glu Glu
    50                  55                  60

Leu Pro Leu Leu Pro Lys Glu Ser Arg Tyr Trp Leu Arg Glu Ile Leu

-continued

```
                65                  70                  75                  80
            Leu Cys Ala Asp Gly Glu Pro Trp Leu Ala Gly Arg Thr Val Val Pro
                            85                  90                  95

Val Ser Thr Leu Ser Gly Pro Glu Leu Ala Leu Gln Lys Leu Gly Lys
                        100                 105                 110

Thr Pro Leu Gly Arg Tyr Leu Phe Thr Ser Thr Leu Thr Arg Asp
                    115                 120                 125

Phe Ile Glu Ile Gly Arg Asp Ala Gly Leu Trp Gly Arg Ser Arg
                130                 135                 140

Leu Arg Leu Ser Gly Lys Pro Leu Leu Thr Glu Leu Phe Leu Pro
            145                 150                 155                 160

Ala Ser Pro Leu Tyr
                        165

<210> SEQ ID NO 39
<211> LENGTH: 39
<212> TYPE: DNA
<213> ORGANISM: Artificial sequence
<220> FEATURE:
<223> OTHER INFORMATION: Primer 19

<400> SEQUENCE: 39
ctactcactt agatctccat ggcttcctct gtcatttct                              39

<210> SEQ ID NO 40
<211> LENGTH: 32
<212> TYPE: DNA
<213> ORGANISM: Artificial sequence
<220> FEATURE:
<223> OTHER INFORMATION: Primer 20

<400> SEQUENCE: 40
catcttactc atatgccaca cctgcatgca gc                                    32

<210> SEQ ID NO 41
<211> LENGTH: 684
<212> TYPE: DNA
<213> ORGANISM: Escherichia coli
<220> FEATURE:
<221> NAME/KEY: CDS
<222> LOCATION: (1)..(684)

<400> SEQUENCE: 41 atg gct tcc tct gtc att tct tca gca gct gtt gcc aca cgc agc aat        48
Met Ala Ser Ser Val Ile Ser Ser Ala Ala Val Ala Thr Arg Ser Asn
1               5                   10                  15 gtt aca caa gct agc atg gtt gca cct ttc act ggt ctc aaa tct tca        96
Val Thr Gln Ala Ser Met Val Ala Pro Phe Thr Gly Leu Lys Ser Ser
            20                  25                  30 gcc act ttc cct gtt aca aag aag caa aac ctt gac atc act tcc att       144
Ala Thr Phe Pro Val Thr Lys Lys Gln Asn Leu Asp Ile Thr Ser Ile
        35                  40                  45 gct agc aat ggt gga aga gtt agc tgc atg cag gtg tgg cat atg tca       192
Ala Ser Asn Gly Gly Arg Val Ser Cys Met Gln Val Trp His Met Ser
    50                  55                  60 cac ccc gcg tta acg caa ctg cgt gcg ctg cgc tat tgt aaa gag atc       240
His Pro Ala Leu Thr Gln Leu Arg Ala Leu Arg Tyr Cys Lys Glu Ile
65                  70                  75                  80 cct gcc ctg gat ccg caa ctg ctc gac tgg ctg ttg ctg gag gat tcc       288
Pro Ala Leu Asp Pro Gln Leu Leu Asp Trp Leu Leu Leu Glu Asp Ser
            85                  90                  95
```

```
atg aca aaa cgt ttt gaa cag cag gga aaa acg gta agc gtg acg atg          336
Met Thr Lys Arg Phe Glu Gln Gln Gly Lys Thr Val Ser Val Thr Met
        100                 105                 110 atc cgc gaa ggg ttt gtc gag cag aat gaa atc ccc gaa gaa ctg ccg          384
Ile Arg Glu Gly Phe Val Glu Gln Asn Glu Ile Pro Glu Glu Leu Pro
            115                 120                 125 ctg ctg ccg aaa gag tct cgt tac tgg tta cgt gaa att ttg tta tgt          432
Leu Leu Pro Lys Glu Ser Arg Tyr Trp Leu Arg Glu Ile Leu Leu Cys
    130                 135                 140 gcc gat ggt gaa ccg tgg ctt gcc ggt cgt acc gtc gtt cct gtg tca          480
Ala Asp Gly Glu Pro Trp Leu Ala Gly Arg Thr Val Val Pro Val Ser
145                 150                 155                 160 acg tta agc ggg ccg gag ctg gcg tta caa aaa ttg ggt aaa acg ccg          528
Thr Leu Ser Gly Pro Glu Leu Ala Leu Gln Lys Leu Gly Lys Thr Pro
                165                 170                 175 tta gga cgc tat ctg ttc aca tca tcg aca tta acc cgg gac ttt att          576
Leu Gly Arg Tyr Leu Phe Thr Ser Ser Thr Leu Thr Arg Asp Phe Ile
            180                 185                 190 gag ata ggc cgt gat gcc ggg ctg tgg ggg cga cgt tcc cgc ctg cga          624
Glu Ile Gly Arg Asp Ala Gly Leu Trp Gly Arg Arg Ser Arg Leu Arg
        195                 200                 205 tta agc ggt aaa ccg ctg ttg cta aca gaa ctg ttt tta ccg gcg tca          672
Leu Ser Gly Lys Pro Leu Leu Leu Thr Glu Leu Phe Leu Pro Ala Ser
    210                 215                 220 ccg ttg tac taa                                                          684
Pro Leu Tyr
225
```

<210> SEQ ID NO 42
<211> LENGTH: 227
<212> TYPE: PRT
<213> ORGANISM: Escherichia coli

<400> SEQUENCE: 42

```
Met Ala Ser Ser Val Ile Ser Ser Ala Ala Val Ala Thr Arg Ser Asn
1               5                   10                  15

Val Thr Gln Ala Ser Met Val Ala Pro Phe Thr Gly Leu Lys Ser Ser
            20                  25                  30

Ala Thr Phe Pro Val Thr Lys Lys Gln Asn Leu Asp Ile Thr Ser Ile
        35                  40                  45

Ala Ser Asn Gly Gly Arg Val Ser Cys Met Gln Val Trp His Met Ser
    50                  55                  60

His Pro Ala Leu Thr Gln Leu Arg Ala Leu Arg Tyr Cys Lys Glu Ile
65                  70                  75                  80

Pro Ala Leu Asp Pro Gln Leu Leu Asp Trp Leu Leu Leu Glu Asp Ser
                85                  90                  95

Met Thr Lys Arg Phe Glu Gln Gln Gly Lys Thr Val Ser Val Thr Met
            100                 105                 110

Ile Arg Glu Gly Phe Val Glu Gln Asn Glu Ile Pro Glu Glu Leu Pro
        115                 120                 125

Leu Leu Pro Lys Glu Ser Arg Tyr Trp Leu Arg Glu Ile Leu Leu Cys
    130                 135                 140

Ala Asp Gly Glu Pro Trp Leu Ala Gly Arg Thr Val Val Pro Val Ser
145                 150                 155                 160

Thr Leu Ser Gly Pro Glu Leu Ala Leu Gln Lys Leu Gly Lys Thr Pro
                165                 170                 175

Leu Gly Arg Tyr Leu Phe Thr Ser Ser Thr Leu Thr Arg Asp Phe Ile
            180                 185                 190
```

-continued

```
Glu Ile Gly Arg Asp Ala Gly Leu Trp Gly Arg Arg Ser Arg Leu Arg
            195                 200                 205

Leu Ser Gly Lys Pro Leu Leu Leu Thr Glu Leu Phe Leu Pro Ala Ser
        210                 215                 220

Pro Leu Tyr
225

<210> SEQ ID NO 43
<211> LENGTH: 33
<212> TYPE: DNA
<213> ORGANISM: Artificial sequence
<220> FEATURE:
<223> OTHER INFORMATION: Primer 21

<400> SEQUENCE: 43
cccgggggta cctaaagaag gagtgcgtcg aag                                  33

<210> SEQ ID NO 44
<211> LENGTH: 46
<212> TYPE: DNA
<213> ORGANISM: Artificial sequence
<220> FEATURE:
<223> OTHER INFORMATION: Primer 22

<400> SEQUENCE: 44
gatatcaagc tttctagagt cgacatcgat ctagtaacat agatga                    46

<210> SEQ ID NO 45
<211> LENGTH: 831
<212> TYPE: DNA
<213> ORGANISM: Pseudomonas putida
<220> FEATURE:
<221> NAME/KEY: CDS
<222> LOCATION: (1)..(831)

<400> SEQUENCE: 45 atg agc aca tac gaa ggt cgc tgg gct acc gtg aag gtc gaa ctg gag       48
Met Ser Thr Tyr Glu Gly Arg Trp Ala Thr Val Lys Val Glu Leu Glu
1               5                   10                  15 tcg ggc att gcc tgg gtc acc ctc aac cgg ccg gaa aag cgc aat gca       96
Ser Gly Ile Ala Trp Val Thr Leu Asn Arg Pro Glu Lys Arg Asn Ala
            20                  25                  30 atg agc ccc acg ctg aac cgg gaa atg gtc gac gtg ctg gaa acc ctg      144
Met Ser Pro Thr Leu Asn Arg Glu Met Val Asp Val Leu Glu Thr Leu
        35                  40                  45 gaa cag gac ggc gaa gcc ggg gtg ctc gtg ctg acc ggc gcg ggt gaa      192
Glu Gln Asp Gly Glu Ala Gly Val Leu Val Leu Thr Gly Ala Gly Glu
    50                  55                  60 tcg tgg acg gca ggc atg gac ctg aag gaa tac ttc cgt gag gtg gac      240
Ser Trp Thr Ala Gly Met Asp Leu Lys Glu Tyr Phe Arg Glu Val Asp
65                  70                  75                  80 gcc ggc ccg gaa atc ctc cag gaa aaa atc cgc cgc gat gcc tcg caa      288
Ala Gly Pro Glu Ile Leu Gln Glu Lys Ile Arg Arg Asp Ala Ser Gln
                85                  90                  95 tgg caa tgg agg ctg ctg cgc atg tac gcc aag ccg act atc gcc atg      336
Trp Gln Trp Arg Leu Leu Arg Met Tyr Ala Lys Pro Thr Ile Ala Met
            100                 105                 110 gtc aac ggc tgg tgc ttt ggc ggc ggc ttc agc ccg ctg gtg gcc tgc      384
Val Asn Gly Trp Cys Phe Gly Gly Gly Phe Ser Pro Leu Val Ala Cys
        115                 120                 125 gac ctg gcc atc tgt gcc gac gag gcc acc ttt ggc ctg tcg gaa atc      432
Asp Leu Ala Ile Cys Ala Asp Glu Ala Thr Phe Gly Leu Ser Glu Ile
```

```
                130                 135                 140
aac tgg ggc atc cca ccg ggc aac ctg gtc agc aaa gcc atg gcc gat      480
Asn Trp Gly Ile Pro Pro Gly Asn Leu Val Ser Lys Ala Met Ala Asp
145                 150                 155                 160 acc gtt ggc cac cgc cag tcg ctg tac tac atc atg acc ggc aag act      528
Thr Val Gly His Arg Gln Ser Leu Tyr Tyr Ile Met Thr Gly Lys Thr
                165                 170                 175 ttc ggc ggg cct aaa gct gcc gag atg ggg ctg gtt aac gag agc gtg      576
Phe Gly Gly Pro Lys Ala Ala Glu Met Gly Leu Val Asn Glu Ser Val
            180                 185                 190 ccg ctg gcg caa ttg cgc gac gtc acc cgc gaa ctg gcg ctc aac ctg      624
Pro Leu Ala Gln Leu Arg Asp Val Thr Arg Glu Leu Ala Leu Asn Leu
        195                 200                 205 ctg gaa aag aac ccg gtg gtg ctg cgt gcg gcc aag aac ggt ttc aag      672
Leu Glu Lys Asn Pro Val Val Leu Arg Ala Ala Lys Asn Gly Phe Lys
    210                 215                 220 cgc tgc cgc gaa ctg acc tgg gag cag aac gaa gac tac ctg tac gcc      720
Arg Cys Arg Glu Leu Thr Trp Glu Gln Asn Glu Asp Tyr Leu Tyr Ala
225                 230                 235                 240 aag ctc gac cag tcc cgt ctg ctg gac acc gaa ggt ggg cgc gag cag      768
Lys Leu Asp Gln Ser Arg Leu Leu Asp Thr Glu Gly Gly Arg Glu Gln
                245                 250                 255 ggc atg aag cag ttc ctc gac gac aag agc atc aag cca ggc ctg caa      816
Gly Met Lys Gln Phe Leu Asp Asp Lys Ser Ile Lys Pro Gly Leu Gln
            260                 265                 270 gcc atc aag cgc tga                                                  831
Ala Ile Lys Arg
        275

<210> SEQ ID NO 46
<211> LENGTH: 276
<212> TYPE: PRT
<213> ORGANISM: Pseudomonas putida

<400> SEQUENCE: 46

Met Ser Thr Tyr Glu Gly Arg Trp Ala Thr Val Lys Val Glu Leu Glu
1               5                   10                  15

Ser Gly Ile Ala Trp Val Thr Leu Asn Arg Pro Glu Lys Arg Asn Ala
                20                  25                  30

Met Ser Pro Thr Leu Asn Arg Glu Met Val Asp Val Leu Glu Thr Leu
            35                  40                  45

Glu Gln Asp Gly Glu Ala Gly Val Leu Val Leu Thr Gly Ala Gly Glu
        50                  55                  60

Ser Trp Thr Ala Gly Met Asp Leu Lys Glu Tyr Phe Arg Glu Val Asp
65                  70                  75                  80

Ala Gly Pro Glu Ile Leu Gln Glu Lys Ile Arg Arg Asp Ala Ser Gln
                85                  90                  95

Trp Gln Trp Arg Leu Leu Arg Met Tyr Ala Lys Pro Thr Ile Ala Met
            100                 105                 110

Val Asn Gly Trp Cys Phe Gly Gly Phe Ser Pro Leu Val Ala Cys
        115                 120                 125

Asp Leu Ala Ile Cys Ala Asp Glu Ala Thr Phe Gly Leu Ser Glu Ile
    130                 135                 140

Asn Trp Gly Ile Pro Pro Gly Asn Leu Val Ser Lys Ala Met Ala Asp
145                 150                 155                 160

Thr Val Gly His Arg Gln Ser Leu Tyr Tyr Ile Met Thr Gly Lys Thr
                165                 170                 175
```

```
Phe Gly Gly Pro Lys Ala Ala Glu Met Gly Leu Val Asn Glu Ser Val
            180             185                 190

Pro Leu Ala Gln Leu Arg Asp Val Thr Arg Glu Leu Ala Leu Asn Leu
        195             200             205

Leu Glu Lys Asn Pro Val Val Leu Arg Ala Ala Lys Asn Gly Phe Lys
    210             215             220

Arg Cys Arg Glu Leu Thr Trp Glu Gln Asn Glu Asp Tyr Leu Tyr Ala
225             230             235             240

Lys Leu Asp Gln Ser Arg Leu Leu Asp Thr Glu Gly Gly Arg Glu Gln
            245             250             255

Gly Met Lys Gln Phe Leu Asp Asp Lys Ser Ile Lys Pro Gly Leu Gln
            260             265             270

Ala Ile Lys Arg
        275
```

UDP-GLUCOSYLTRANSFERASES

This application claims benefit of U.S. Provisional Application No. 60/355,511, filed Feb. 7, 2002.

FIELD OF INVENTION

This invention relates to field of plant molecular biology. More specifically, this invention pertains to nucleic acid fragments encoding plant glucosyltransferases.

BACKGROUND

Recent advances in genetic engineering have enabled the development of new biological platforms to produce molecules heretofore only synthesized by chemical routes. Although microbial fermentation is routinely exploited for the production of small molecules and proteins of industrial and/or pharmaceutical importance (antibiotics, enzymes, vaccines, etc.), the possibility of using green plants for the manufacture of high-volume chemicals and materials has become an increasingly attractive alternative.

There are two obvious advantages of using green plants to produce large amounts of compounds that are traditionally manufactured through normal chemical synthesis. First, green plants constitute a renewable energy source, as opposed to petrochemical production. Because of their unique photosynthetic capability, the only raw materials that are required to produce carbon-based compounds in green plants are carbon dioxide, water, and soil, with sunlight providing the ultimate source of energy. Second, in comparison to existing fermentation facilities which are limited in size, green plants constitute a huge available biomass that could easily accommodate the large amounts of chemicals that are required for certain high-volume, low-cost applications. However, there are still a number of important obstacles that must be overcome before green plants can be exploited for this purpose. For example, living plants might not be able to tolerate high levels of certain compounds, even if they are naturally found in plants, albeit at much lower levels. Although toxicity also poses potential problems for the production of chemicals through fermentation, plants are vastly more complex than fungi, bacteria, or other microorganisms, especially with regard to genetics, metabolism and cellular differentiation.

Fortunately, however, plants and animals deploy remarkably similar mechanisms for detoxifying the broad range of toxic compounds to which they are exposed or produce themselves (Sandermann, *Pharmacogenetics* 4:225–241 (1994)). In both kingdoms, the detoxification of exogenous and endogenous toxins is a three-phase process (Coleman, *Trends Plant Sci.* 2:144–151 (1997); Wink, M. In *The Plant Vacuole: Advances in Botanical Research*; Leigh, R. A., Sanders, D. and Callow, J. A., Eds.; Academic Press: London, N.Y., 1997; Vol. 25, pp 141–169). Phase I (activation) is the introduction or exposure of functional groups of the appropriate reactivity for phase II enzymes. Cytochrome P450-dependent monooxygenases and mixed function oxidases are examples of phase I enzymes. Phase II (conjugation) is covalent attachment of the activated compound to a bulky hydrophilic molecule that increases its water solubility and is thought to promote its recognition by phase III transporters. Phase III (elimination) is transport of the conjugates out of the cytosol into intracellular compartments and/or the extracellular space. In mammals, the conjugates are typically excreted into the urine or bile. In plants, that otherwise lack bona fide excretory organs, the conjugates are often sequestered in the vacuole, a large acidic organelle that constitutes 40–90% of the total cell volume.

Due to their pharmacological importance, the best characterized phase II reactions are probably those catalyzed by mammalian UDP-glucuronyltransferases which attach glucuronic acid to a wide range of acceptor molecules (Meech and Mackenzie, *Clinical and Experimental Pharmacology and Physiology* 24:907–915 (1997)). Closely related homologs exist in plants, as judged by the presence of more than one hundred ORFs in arabidopsis encoding polypeptides bearing a C-terminal consensus sequence common to all members of the UDP-glycosyltransferase superfamily (Mackenzie et al., *Pharmacogenetics* 7:255–269 (1997); Lim et al., *J. Biol. Chem.* 276:4344–4349 (2001)), but less is known about these enzymes than their mammalian counterparts. The majority of the plant enzymes are thought to use UDP-glucose as the sugar donor, but their natural substrates and physiological functions largely remain elusive, despite the increasing number of purified proteins that have been rigorously characterized over the last several years (Lim et al., supra; Jackson et al., *J. Biol. Chem.* 276:4350–4356 (2001); Ford et al., *J. Biol. Chem.* 273: 9224–9233 (1998); Vogt et al., *Plant J.* 19:509–519 (1999); Lee and Raskin, *J. Biol Chem.* 274:36637–36642 (1999); Fraissinet-Tachet et al., *FEBS Lett.* 437:319–323 (1998)). However, it is tacitly assumed that one of the key roles of plant UDP-glucosyltransferases is to target endogenous and exogenous toxins to the vacuole.

Most of the products of secondary metabolism in plants are glycosylated (Harborne, *J. Introduction to Ecological Biochemistry*, 4$^{th}$ ed.; Academic Press: London, 1993), as are many herbicides after modification by phase I enzymes. An impressive array of conjugated species, including coumaryl glucosides, flavonoids, anthocyanins, cardenolides, soponins, cyanogenic glucosides, glucosinolates, and betalains, are known to be stored in the vacuole (Wink, M., supra). Based on these observations and the fact that most UDP-glucosyltransferases are located in the cytosol, glucosylation has been invoked as a prerequisite for uptake and accumulation in the vacuole. In addition, in vitro experiments clearly demonstrate that isolated vacuoles and/or vacuolar membrane vesicles are able to take up certain glucose conjugates, while the parent molecules are not transported (Wink, M., supra).

p-Hydroxybenzoic acid (pHBA) is a naturally occurring plant secondary metabolite that has been shown to have a number of useful applications. It is the major monomer of Liquid Crystal Polymers (LCPs), ~55% of the total weight, and chemical precursor for the synthesis of methylparaben, which is a preservative that is commonly used in the food and cosmetic industries. Since it is anticipated that the global demand for pHBA will exceed one hundred million pounds per year by the end of the decade, green plants represent an attractive platform for the production of this compound.

Indeed, it has recently been shown (Siebert et al., *Plant Physiol.* 112:811–819 (1996)) that it is possible to increase pHBA levels in tobacco two to three orders of magnitude using a chloroplast-targeted version of *E. coli* chorismate pyruvate lyase (CPL). Interestingly, virtually all of the overproduced pHBA (>95%) was converted to two glucose conjugates, a phenolic glucoside with the glucose moiety attached to the aromatic hydroxyl group, and a glucose ester where the sugar is attached to the aromatic carboxyl group. Although both glucose conjugates accumulate in the vacuole, they have very different chemical properties and physiological roles.

For example, the pHBA glucose ester (like other acetal esters) is characterized by high free energy of hydrolysis, which makes it very simple to recover the parent compound with low concentrations of either acid or base. This could greatly reduce the cost of producing pHBA in plants. Furthermore, it is well established that certain glucose esters are able to serve as activated acyl donors in enzyme-mediated transesterification reactions (Li et al., *Proc. Natl. Acad. U.S.A.* 97, 12:6902–6907 (2000); Lehfeldt et al., *Plant Cell* 12, 8:1295–1306 (2000)), In light of these observations, it would be extremely desirable to control the partitioning of pHBA glucose conjugates in vivo. For example, by overexpressing an appropriate glucosyltransferase in transgenic plants that generate large amounts of pHBA, it might be possible to accumulate all of the desired compound as the glucose ester, which is easily hydrolyzed to free pHBA. While the above scenario is extremely attractive; it requires an enzyme with the appropriate properties and molecular information that would allow access to the gene (e.g., its nucleotide or primary amino acid sequence).

Several publications describe plant enzymes that catalyze the formation of glucosides and/or glucose esters of hydroxybenzoic acids. For example, Klick et al. (*Phytochemistry* 27(7):2177–2180 (1988)) reported that glucose conjugates of hydroxybenzoic acids are present as low abundance secondary metabolites in a wide range of plant species, and occur in nature as both glucosides and glucose esters. Gross et al. (*Phytochemistry* 10:2179–2183 (1983)) described an enzyme activity from oak trees that catalyzes the formation of glucose esters of hydroxybenzoic acids, including pHBA. Bechthold et al. (*Archives of Biochemistry and Biophysics* 288(1):39–47 (1991)) described an enzyme activity in cell cultures of *Lithospermum erythrorhizon* that was very specific for pHBA and only formed the pHBA phenolic glucoside. In a subsequent study (Li et al., *Phytochemistry* 46(1):27–32 (1997)), the same protein was purified to homogeneity and subjected to digestion with endoprotease Lys-C. Although several peptide fragments were successfully sequenced, the authors did not publish this information. Chorismate pyruvate-lyase (CPL)-mediated production of pHBA in transgenic tobacco plants resulted in accumulation of the pHBA phenolic glucoside and pHBA glucose ester (Siebert et al., *Plant Physiol.* 112:811–819 (1996)). Moreover, similar results were obtained when pHBA was generated in the cytosol using a different bacterial gene, namely, the HCHL (4-hydroxycinnamoyl-CoA hydratase/lyase) gene from *Pseudomonas fluorescens* (Mayer et al., *Plant Cell* 13(7):1669–1682 (2001). Li et al. (*Plant Cell Physiol.* 38(7):844–850 (1997)) described glucosyltransferase activities in tobacco cell cultures that catalyze the formation of both pHBA conjugates, but the experiments were performed with crude extracts, not purified proteins. None of the reports cited above describe at the molecular level any genes or proteins that are responsible for the pHBA phenolic or ester glucosides.

On the other hand, Fraissinet-Tachet et al. (*FEBS Lett.* 437(3):319–323(1998)) has presented the complete nucleotide sequences of two closely related UDP-glucosyltransferases from tobacco that are active with pHBA, and characterized the purified recombinant proteins. However, both enzymes interact with a wide variety of substrates that bear little resemblance to each other. Moreover, both enzymes attach glucose to the hydroxyl and carboxyl group of pHBA. Lee and Raskin (*J. Biol. Chem.* 274:36637–36642 (1999)) published the complete DNA sequence of a different tobacco UDP-glucosyltransferase that is also able to glucosylate pHBA. However, this protein also exhibits very broad substrate specificity and yields both glucosides and glucose esters of various hydroxybenzoic acids and hydroxycinnamic acids. Additionally, Milkowski and colleagues (Milkowski et al., *Planta* 211(6):883–886 (2000); Milkowski et al., *FEBS Lett.* 486(2):183–184 (2000)) and Lim et al., (supra) describe a family of genes from cruciferous plants, *Brassica napus* and *Arabidopsis thaliana*, that encode for UDP-glucosyltransferases that exclusively catalyze the formation of glucose esters. However, in the case of the arabidopsis homologs (Lim et al., supra), the only substrates examined were cinnamic acid derivatives, and there was tremendous variation in the substrate specificity of the different enzymes even within this class of compounds. Moreover, although pHBA was one of the test substrates for the *Brassica* protein (Milkowski et al., *Planta* 211(6):883–886 (2000)) and the arabidopsis proteins (Milkowski et al., *FEBS Lett.* 486(2): 183–184 (2000)), the authors reported that this compound was not glucosylated under the conditions of their in vitro assay.

Three UDP-glucosyltransferase proteins from *Arabidopsis thaliana* that are capable of glucosylating pHBA have been reported to attach glucose exclusively to the aromatic carboxyl group to form the pHBA glucose ester (Lim et al., *J. Biol. Chem.* 277: 586–592 (2002)). One of these proteins, referred to as 84A1, is identical to GT 3 described in the present application, based on structural similarity and kinetic properties, but is not a member of the new subfamily of UDP-glucosyltransferases that are identified herein. Although GT3/84A1 is able to form the pHBA glucose ester, this enzyme exhibits a marked preference for hydroxycinnamic acid derivatives, like sinapic acid, and has a relatively low turnover number for pHBA. The other two arabidopsis proteins described in the above disclosure (e.g., 75B1 and 75B2) are even more distantly related to the UDP-glucosyltransferases that we have discovered. For example, both proteins are less than 45% identical to the instant Grape GT at the amino acid sequence level when compared by gap alignment. Consequently, none of these proteins (GT3/84A1, 75B1, or 75B2) are a suitable catalyst for purposes of the present invention.

The problem to be solved, therefore, is the lack of enzymes that preferentially catalyze the formation of glucose esters of pHBA and other hydroxybenzoic acid derivatives with sufficiently high turnover for use in various applications, both in vitro and in vivo.

SUMMARY OF THE INVENTION

The present invention provides unique UDP-glucosyltransferase enzymes isolated from grape and eucalyptus. The grape and eucalyptus proteins are 82% identical to each other at the amino acid sequence level. These enzymes are characterized by a strong preference for pHBA as substrate as compared to other hydroxybenzoic acid derivatives and hydroxycinnamic acid derivatives, an ability to direct glucose exclusively to the carboxyl group of pHBA, and a high turnover number with pHBA as substrate. These enzymes are useful for preferentially catalyzing the formation of glucose esters of pHBA and other hydroxybenzoic acid derivatives that are industrially valuable.

Accordingly, the invention provides an isolated nucleic acid molecule encoding a UDP-glucosyltransferase enzyme selected from the group consisting of: (a) an isolated nucleic acid molecule encoding the amino acid sequence set forth in SEQ ID NO:18 or SEQ ID NO:22; an isolated nucleic acid molecule that hybridizes with (a) under the following stringent hybridization conditions: 0.1×SSC, 0.1% SDS at 65°

C., and washed with 2×SSC, 0.1% SDS followed by 0.1× SSC, 0.1% SDS; and an isolated nucleic acid molecule that is complementary to (a) or (b).

In a similar fashion this invention provides an isolated nucleic acid molecule encoding a UDP-glucosyltransferase enzyme selected from the group consisting of: an isolated nucleic acid molecule encoding the amino acid sequence set forth in SEQ ID NO:31; an isolated nucleic acid molecule that hybridizes with (a) under the following stringent hybridization conditions: 0.1×SSC, 0.1% SDS at 65° C., and washed with 2×SSC, 0.1% SDS followed by 0.1×SSC, 0.1% SDS; and an isolated nucleic acid molecule that is complementary to (a) or (b).

Also provided in this invention is an isolated nucleic acid molecule encoding a UDP-glucosyltransferase enzyme having: a) at least 75% identity to the amino acid sequence set forth in SEQ ID NO:18 or at least 72% identity to the amino acid sequence set forth in SEQ ID NO:22; b) activity to catalyze the production of pHBA ester glucoside from pHBA; c) at least a 4.88-fold substrate preference for pHBA over sinapic acid at a 10 mM substrate concentration; and d) a turnover number of at least 1.77 $sec^{-1}$ for the conversion of pHBA to pHBA ester glucoside.

Even more specifically, the invention encompasses an isolated nucleic acid molecule selected from the group consisting of SEQ ID NO:17 and SEQ ID NO:21, as well as an isolated nucleic acid molecule having the sequence set forth in SEQ ID NO:30.

Additionally, the invention encompasses polypeptides encoded by the isolated nucleic acid molecules set forth herein, preferentially those having an amino acid sequence selected from the group consisting of SEQ ID NO:18, SEQ ID NO:22, or the amino acid sequence set forth in SEQ ID NO:31.

The invention provides an isolated nucleic acid molecule comprising a) a nucleotide sequence encoding an UDP-glucosyltransferase enzyme having at least 82% identity over the length of 478 amino acids based on the Smith-Waterman method of alignment when compared to a polypeptide having the sequence set forth in SEQ ID NO:18, or a nucleotide sequence comprising the complement of the nucleotide sequence of (a); or b) an isolated nucleic acid molecule comprising a nucleotide sequence encoding an UDP-glucosyltransferase enzyme having at least 82% identity over the length of 511 amino acids based on the Smith-Waterman method of alignment when compared to a polypeptide having the sequence set forth in SEQ ID NO:22, or a nucleotide sequence comprising the complement of the nucleotide sequence of (b).

The invention also encompasses genetic chimera and transformed host cells comprising the any of the nucleic acid molecules disclosed herein and operably linked to suitable regulatory sequences, as well as transformed host cells comprising the these genetic materials. These genetic chimera and transformed host cells further include one or both nucleic acid fragments selected from the group consisting of: i) a nucleic acid fragment for chorismate pyruvate lyase enzyme activity, the nucleic acid fragment encoding a polypeptide having the amino acid sequence set forth in SEQ ID NO:38; and ii) a nucleic acid fragment for 4-hydroxycinnamoyl-CoA hydratase/lyase enzyme activity, the nucleic acid fragment encoding a polypeptide having the amino acid sequence set forth in SEQ ID NO:46, each nucleic acid fragment operably linked to suitable regulatory sequences for protein production.

Additionally, the invention encompasses a method for regulating (including increasing or decreasing) UDP-glucosyltransferase enzyme activity in a microorganism or green plant cell comprising (a) expressing (which may include the step of transforming) a host microorganism or green plant cell with an UDP-glucosyltransferase gene comprising the nucleotide sequence set forth in SEQ ID NO:17, SEQ ID NO:21, or SEQ ID NO:30, the nucleic acid sequence operably linked to suitable regulatory sequences; and (b) growing the transformed host microorganism or green plant cell of step a) under appropriate conditions for expression of the UDP-glucosyltransferase gene.

Furthermore, the invention encompasses a preferred method for increasing the ratio of the pHBA ester glucoside to total pHBA glucose conjugates in pHBA-producing microorganisms and green plant cells, the method comprising: a) providing a host microorganism or green plant cell with a nucleic acid fragment encoding a polypeptide for UDP-glucosyltransferase enzyme activity operably linked to suitable regulatory sequences ("providing" includes transforming a host cell originally without suitable pHBA producing capability), the polypeptide having 1) at least 75% identity to an amino acid sequence as set forth in SEQ ID NO:18 or at least 72% identity to an amino acid sequence as set forth in SEQ ID NO:22; 2) at least a 4.88-fold substrate preference for pHBA over sinapic acid at a 10 mM substrate concentration; and 3) a turnover number of at least 1.77 $sec^{-1}$ for conversion of pHBA to pHBA ester glucoside, b) growing the pHBA-producing microorganism or green plant cell of step a) under suitable conditions for expressing UDP-glucosyltransferase activity and for producing pHBA ester glucoside; and c) recovering pHBA ester glucoside, the ratio of pHBA ester glucose to total pHBA glucose conjugates at least 10% greater than the ratio of pHBA ester glucose to total pHBA glucose conjugates of an untransformed host cell. More specifically, the nucleic acid fragment encoding a UDP-glucosyltransferase enzyme encodes a polypeptide having the amino acid sequence selected from the group consisting of SEQ ID NO:18, SEQ ID NO:22, and SEQ ID NO:31. Alternatively, the nucleic acid fragment encoding a UDP-glucosyltransferase enzyme comprises a nucleic acid sequence selected from the group consisting of SEQ ID NO:17, SEQ ID NO:21, and SEQ ID NO:30.

The preferred method may encompass providing a host cell further comprising one or both exogenous nucleic acid fragments selected from the group consisting of: i) a nucleic acid fragment for a chorismate pyruvate lyase enzyme, the nucleic acid fragment encoding a polypeptide having the amino acid sequence set forth in SEQ ID NO:38; and ii) a nucleic acid fragment for a 4-hydroxycinnamoyl-CoA hydratase/lyase enzyme, the nucleic acid fragment encoding a polypeptide having the amino acid sequence set forth in SEQ ID NO:46, each nucleic acid fragment operably linked to suitable regulatory sequences for protein production.

In a further embodiment the invention encompasses a method for the in vitro production of pHBA ester glucoside comprising i) contacting in vitro pHBA with UDP-glucose in the presence of an effective amount of a UDP-glucosyltransferase enzyme having a) at least 75% identity to the amino acid sequence set forth in SEQ ID NO:18, or at least 72% identity to the amino acid sequence set forth in SEQ ID NO:22; b) at least a 4.88-fold substrate preference for pHBA over sinapic acid at a 10 mM substrate concentration; and a turnover number of at least 1.77 $sec^{-1}$ for conversion of pHBA to the pHBA ester glucoside; and ii) isolating the pHBA ester glucoside.

BRIEF DESCRIPTION OF THE DRAWINGS, SEQUENCE DESCRIPTIONS, AND BIOLOGICAL DEPOSIT

The invention can be more fully understood from the sequence listing, the Figures, a biological deposit, and the detailed description, which together form this application.

Figure 1:
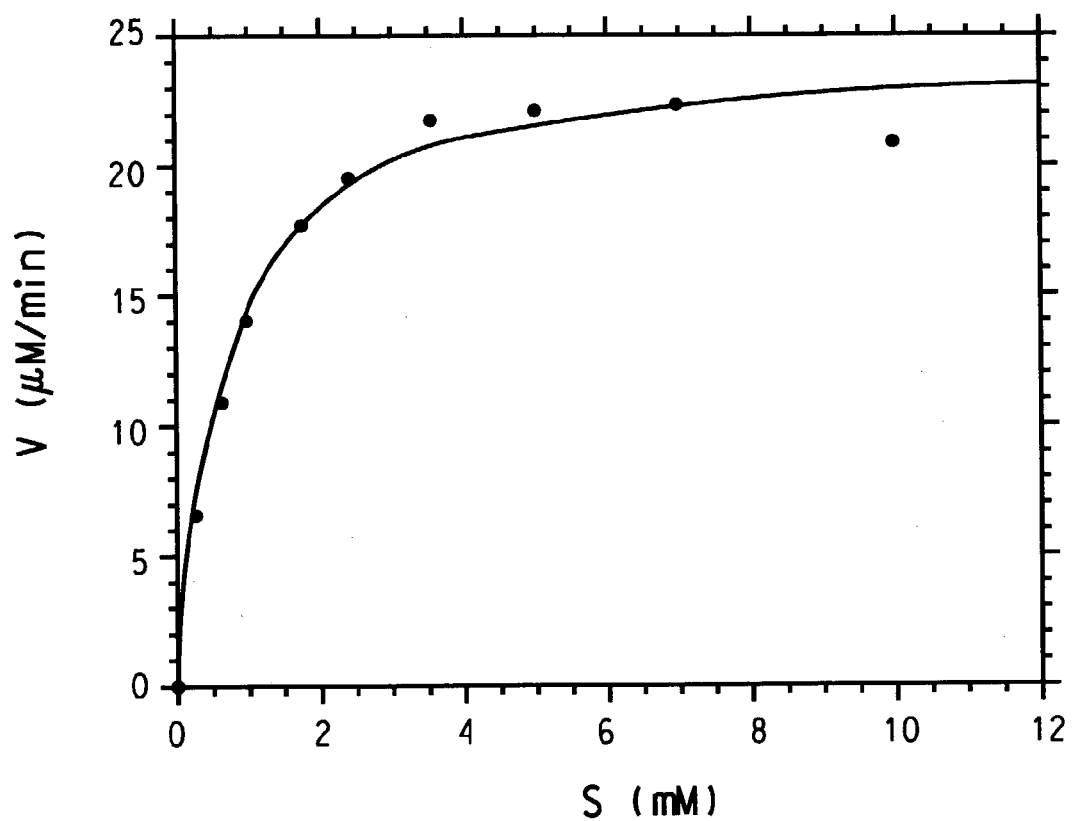
FIG. 1 shows a kinetic analysis of the purified recombinant Grape GT with pHBA as a substrate. Initial rates of product formation are plotted against substrate concentration.

The following brief sequence descriptions and corresponding sequence listing attached hereto comply with the rules governing nucleotide and/or amino acid sequence disclosures in patent applications as set forth in 37 C.F.R. §1.821–1.825. The sequences contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the 5' primer useful for introducing *Brassica napus* SA-GT, having GenBank® accession No. AF287143, in the *Escherichia coli* expression vector, pET-24a(+).

SEQ ID NO:2 is the 3' primer useful for introducing *Brassica napus* SA-GT, having GenBank® accession No. AF287143, in the *Escherichia coli* expression vector, pET-24a(+).

SEQ ID NO:3 is the nucleotide sequence of the ORF of the PCR-amplified *Brassica napus* SA-GT in the *Escherichia coli* expression vector, pET-24a(+).

SEQ ID NO:4 is the deduced primary amino acid sequence of the ORF of the PCR-amplified *Brassica napus* SA-GT in the *Escherichia coli* expression vector, pET-24a(+).

SEQ ID NO:5 is the 5' primer useful for introducing the ORF that corresponds to GenBank® Accession No. AL161541.2 (referred to in the instant invention as Arabidopsis GT 3) in the *Escherichia coli* expression vector, pET-28a(+).

SEQ ID NO:6 is the 3' primer useful for introducing the ORF that corresponds to GenBank® Accession No. AL161541.2 (referred to in the instant invention as Arabidopsis GT 3) in the *Escherichia coli* expression vector, pET-28a(+).

SEQ ID NO:7 is the nucleotide sequence of the ORF of the PCR-amplified Arabidopsis GT 3 in the *Escherichia coli* expression vector, pET-28a(+).

SEQ ID NO:8 is the deduced primary amino acid sequence of the ORF of the PCR-amplified Arabidopsis GT 3 in the *Escherichia coli* expression vector, pET-28a(+).

SEQ ID NO:9 is the 5' primer useful for introducing the ORF that corresponds to GenBank® Accession No. AL161541 (referred to in the instant invention as Arabidopsis GT 4) in the *Escherichia coli* expression vector, pET-28a(+).

SEQ ID NO:10 is the 3' primer useful for introducing the ORF that corresponds to GenBank® accession No. AL161541 (referred to in the instant invention as Arabidopsis GT 4) in the *Escherichia coli* expression vector, pET-28a(+).

SEQ ID NO:11 is the nucleotide sequence of the ORF of the PCR-amplified Arabidopsis GT 4 in the *Escherichia coli* expression vector, pET-28a(+).

SEQ ID NO:12 is the deduced primary amino acid sequence of the ORF of the PCR-amplified Arabidopsis GT 4 in the *Escherichia coli* expression vector, pET-28a(+).

SEQ ID NO:13 is the 5' primer useful for introducing the ORF that corresponds to GenBank® accession No. AL161541.2 (referred to in the instant invention as Arabidopsis GT 5) in the *Escherichia coli* expression vector, pET-28a(+).

SEQ ID NO:14 is the 3' primer useful for introducing the ORF that corresponds to GenBank® accession No. AL161541.2 (referred to in the instant invention as Arabidopsis GT 5) in the *Escherichia coli* expression vector, pET-28a(+).

SEQ ID NO:15 is the nucleotide sequence of the ORF of the PCR-amplified Arabidopsis GT 5 in the *Escherichia coli* expression vector, pET-28a(+).

SEQ ID NO:16 is the deduced primary amino acid sequence of the ORF of the PCR-amplified Arabidopsis GT 5 in the *Escherichia coli* expression vector, pET-28(+).

SEQ ID NO:17 is the nucleotide sequence of the ORF of the Grape GT cDNA insert, that is present in Applicants' cDNA clone known as vmb1na.pk009.c8.

SEQ ID NO:18 is the deduced primary amino acid sequence of the ORF of the Grape GT cDNA insert, that is present in Applicants' cDNA clone known as vmb1na.pk009.c8.

SEQ ID NO:19 is the 5' primer useful for amplification of the nucleotide sequence of the Grape GT ORF and its insertion into the *Escherichia coli* expression vector, pET-24a(+).

SEQ ID NO:20 is the 3' primer useful for amplification of the nucleotide sequence of the Grape GT ORF and its insertion into the *Escherichia coli* expression vector, pET-24a(+).

SEQ ID NO:21 is the nucleotide sequence of the ORF of the Eucalyptus GT cDNA insert, that is present in Applicants' cDNA clone known as eea1c.pk002.016.

SEQ ID NO:22 is the deduced primary amino acid sequence of the ORF of the Eucalyptus GT cDNA insert, that is present in Applicants' cDNA clone known as eea1c.pk002.016.

SEQ ID NO:23 is the 5' primer useful for amplification of the nucleotide sequence of the Eucalyptus GT ORF and its insertion into the *Escherichia coli* expression vector, pET-29a(+) (Novagen).

SEQ ID NO:24 is the 3' primer useful for amplification of the nucleotide sequence of the Eucalyptus GT ORF and its insertion into the *Escherichia coli* expression vector, pET-29a(+).

SEQ ID NO:25 is the 3' primer useful for amplification of the nucleotide sequence of the Eucalyptus GT ORF and its insertion into the *Escherichia coli* expression vector, pET-29a(+) to produce an in frame fusion with sequences of the vector coding encoding a c-terminal extension of 13 amino acids including a hexa histidine tag.

SEQ ID NO:26 is the nucleotide sequence of the ORF created by in frame fusion of the PCR-amplified Eucalyptus cDNA with pET-29a sequences in the *Escherichia coli* expression vector, pET-29a(+).

SEQ ID NO:27 is the deduced primary amino acid sequence of the ORF created by in frame fusion of the PCR-amplified Eucalyptus cDNA with pET-29a sequences in the *Escherichia coli* expression vector, pET-29a(+).

SEQ ID NO:28 is the 5' primer useful for introducing the *Citrus mitis* GT gene in the *Escherichia coli* expression vector, pET-29a(+).

SEQ ID NO:29 is the 3' primer useful for introducing the *Citrus mitis* GT gene in the *Escherichia coli* expression vector, pET-29a(+).

SEQ ID NO:30 is the nucleotide sequence of the ORF of the PCR-amplified *Citrus mitis* GT gene in the pCR-2.1 vector.

SEQ ID NO:31 is the deduced primary amino acid sequence of the ORF of the *Citrus mitis* GT gene in the pCR-2.1 vector.

SEQ ID NO:32 is the 3' primer useful for amplification of the nucleotide sequence of the *Citrus mitis* GT ORF and its insertion into the *Escherichia coli* expression vector, pET-29a(+) (Novagen) to produce an in frame fusion with sequences of the vector coding encoding a c-terminal extension of 15 amino acids including a hexa histidine tag.

SEQ ID NO:33 is the nucleotide sequence of the ORF created by in frame fusion of the PCR-amplified *Citrus mitis* gene with pET-29a sequences in the *Escherichia coli* expression vector, pET-29a(+) (Novagen).

SEQ ID NO:34 is the deduced primary amino acid sequence of the ORF created by in frame fusion of the PCR-amplified *Citrus mitis* gene with pET-29a sequences in the *Escherichia coli* expression vector, pET-29a(+) (Novagen).

SEQ ID NO:35 is the 5' primer useful for amplification of the nucleotide sequence of the *E. coli* ubiC gene using genomic DNA from *E. coli* strain W3110 and its insertion into the *Escherichia coli* expression vector pET-24a(+). (GenBank® Accession No. M96268).

SEQ ID NO:36 is the 3' primer useful for amplification of the nucleotide sequence of the *E. coli* ubiC gene using genomic DNA from *E. coli* strain W3110 and its insertion into the *Escherichia coli* expression vector pET24a(+). (GenBank® Accession No. M96268).

SEQ ID NO:37 is the nucleotide sequence of the ORF of the PCR-amplified CPL in *Escherichia coli* expression vector, pET-24a(+).

SEQ ID NO:38 is the deduced primary amino acid sequence of the ORF of the PCR-amplified CPL in *Escherichia coli* expression vector, pET-24a(+).

SEQ ID NO:39 is the 5' primer useful for amplification of the nucleotide sequence encoding the transit peptide from the Rubisco small subunit precursor from plasmid pTSS1-91(#2)-IBI and its insertion into expression vector pET-24a-CPL.

SEQ ID NO:40 is the 3' primer useful for amplification of the nucleotide sequence encoding the transit peptide from the Rubisco small subunit precursor from plasmid pTSS1-91(#2)-IBI and its insertion into expression vector pET-24a-CPL.

SEQ ID NO:41 is the nucleotide sequence of the ORF of the PCR-amplified TP-CPL in *Escherichia coli* expression vector, pET24a-TP-CPL.

SEQ ID NO:42 is the deduced primary amino acid sequence of the ORF of the PCR-amplified TP-CPL in *Escherichia coli* expression vector, pET24a-TP-CPL.

SEQ ID NO:43 is the 5' primer useful in the amplification of a shortened 3'NOS terminator sequence from plasmid pMH40 and its insertion into plasmid pML3 yielding plasmid pML63.

SEQ ID NO:44 is the 3' primer useful in the amplification of a shortened 3'NOS terminator sequence from plasmid pMH40 and its insertion into plasmid pML3 yielding plasmid pML63.

SEQ ID NO:45 is the nucleotide sequence of the *Pseudomonas putida* HCHL gene (Mukeim and Learch. Appl. Microbiol. Biotechnol. 51:456–461 (1999)).

SEQ ID NO:46 is the predicted amino acid sequence of the *Pseudomonas putida* HCHL gene (Mukeim and Learch, Appl. Microbiol. Biotechnol. 51:456–461 (1999)).

Applicants have made the following biological deposit under the terms of the Budapest Treaty on the International Recognition of the Deposit of Microorganisms for the purposes of Patent Procedure:

| Depositor Identification Reference | Int'l. Depository Designation | Date of Deposit |
| --- | --- | --- |
| Plasmid pZBL1 | ATCC 209128 | Jun. 24, 1997 |

As used herein, "ATCC" refers to the American Type Culture Collection International Depository located at 10801 University Boulevard, Manassas, Va. 20110-2209, U.S.A. The "ATCC No." is the accession number to cultures on deposit with the ATCC.

The listed deposit(s) will be maintained in the indicated international depository-for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The present invention has solved the stated problem by providing nucleotide and deduced amino acid sequences for novel UDP-glucosyltransferase genes and corresponding proteins from grape (Vitis sp.), eucalyptus (*Eucalyptus grandis*), and citrus (*Citrus mitis*) that have a high turnover number with pHBA, exhibit a marked preference for this compound as a substrate, and only attach glucose to the aromatic carboxyl group to form the pHBA ester glucoside.

These enzymes constitute a new sub-family of plant UDP-glucosyltransferases. Additionally, Applicants have identified a UDP-glucosyltransferase in the public database from *Citrus unshiu* (GenBank® Accession No. AB033758.1) that appears to belong to the same new sub-family of proteins that form pHBA glucose ester disclosed herein.

One of the principal utilities for the present UDP-glucosyltransferase enzymes is the conjugation of benzoic acid monomers to glucose for the accumulation of the glucoside in plant vacuoles. Of particular interest in the present invention are the glucosides of pHBA and other structurally related monomers.

The nucleic acid fragments of the present invention may also be used to create transgenic plants in which the present UDP-glucosyltransferase enzymes are present at levels higher or lower than in untransformed host cells. Alternatively, the disclosed UDP-glucosyltransferase enzymes may be expressed in specific plant tissues and/or cell types, or during developmental stages in which they would normally not be encountered. The expression of full-length plant UDP-glucosyltransferase cDNAs (i.e., any of the present sequences or related sequences incorporating an appropriate in-frame ATG start codon) in a bacteria (e.g., *Escherichia coli*), yeast (e.g., *Saccharomyces cerevisiae, Pichia pastoralis*) or plant (e.g., tobacco, *arabidopsis*) yields a mature protein capable of participating in glycosylation.

The present invention also includes a process for forming pHBA glucose ester via the UDP-glucosyltransferases disclosed herein. One of the major advantages of having plants that only form the pHBA ester glucoside is that it is very easy to recover free pHBA from this compound. The pHBA glucose ester is far more susceptible to acid and base hydrolysis than is the pHBA phenolic glucoside. Using milder conditions to cleave off the associated glucose molecule from the pHBA ester glucoside could substantially reduce the cost of recovery and purification of free pHBA using a plant-based platform. Thus, partitioning pHBA to the glucose ester by co-expressing an appropriate UDP-glucosyltransferase, like the Grape GT, with CPL, HCHL, or both enzymes, could significantly lower the manufacturing cost of polymer-grade pHBA for LCPs and other applications.

Furthermore, the nucleotide and protein sequence information described herein provide very useful tools for identifying and isolating similar UDP-glucosyltransferases that preferentially catalyze the formation of the glucose ester of pHBA and other hydroxybenzoic acid derivatives and can be used for various in vitro and in vivo applications.

In this disclosure, a number of terms and abbreviations are used. The following definitions are provided.

"p-Hydroxybenzoic acid" is abbreviated pHBA.

"m-Hydroxybenzoic acid" is abbreviated mHBA.

"o-Hydroxybenzoic acid" is abbreviated oHBA.

"Sinapic acid" is abbreviated SA.

"UDP-glucosyltransferase" or "glucosyltransferase" is abbreviated GT.

The term, "UDP-glucosyltransferase" refers to enzymes involved in the formation of glucose-conjugated molecules. Such proteins catalyze a reaction between UDP-glucose and an acceptor molecule to form UDP and the glucosylated acceptor molecule. In most cases the hydroxyl group on C1 of β-D-glucose is attached to the acceptor molecule via a 1-O-β-D-linkage.

The terms "Grape UDP-glucosyltransferase", "Grape glucosyltransferase", and "Grape GT" are used interchangeably to refer to the Vitis sp. UDP-glucosyltransferase described in the present invention.

The terms "Eucalyptus UDP-glucosyltransferase", "Eucalyptus glucosyltransferase", and "Eucalyptus GT" are used interchangeably to refer to the *Eucalyptus grandis* UDP-glucosyltransferase described in the present invention.

The terms "Citrus UDP-glucosyltransferase", "Citrus glucosyltransferase", and "Citrus GT" are used interchangeably to refer to the Citrus mitis UDP-glucosyltransferase described in the present invention, which is very similar to the *Citrus unshiu* UDP-glucosyltransferase (GenBank® Accession No. AB033758.1) in the public domain "*Brassica napus* SA-GT" and "*Brassica* SA-GT" are used interchangeably to refer to the *Brassica napus* UDP-glucosyltransferase (GenBank® Accession No. AF287143). This enzyme catalyzes the transfer of glucose from UDP-glucose to the carboxyl group of sinapic acid and several other hydroxycinnamic acid derivatives.

"Chorismate Pyruvate Lyase" is abbreviated CPL and refers to an enzyme that catalyzes the conversion of chorismate to pHBA and pyruvate. "4-hydroxycinnamoyl-CoA hydratase/lyase" is abbreviated HCHL and refers to an enzyme that catalyzes the hydration of the double bond of a hydroxycinnamoyl CoA thioester followed by a retro aldol cleavage reaction that produces a benzoyl aldehyde and acetyl CoA.

The terms "p-hydroxybenzoic acid glucoside" and "pHBA glucoside" refer to glucose conjugated pHBA, either the phenolic glucoside or glucose ester. The latter is also referred to as the pHBA ester glucoside. Both conjugates are monoglucosides that contain a 1-O-β-D linkage.

The term "pHBA derivative" refers to any conjugate that is formed from pHBA, including pHBA glucosides.

The terms "turnover number" or "maximum turnover number" are used interchangeably with $k_{cat}$ The term "aglycone" refers to substrates that lack a glucose moiety and that are useful in the present invention.

The terms "transit peptide" or "chloroplast transit peptide" are abbreviated "TP" and refer to the N-terminal portion of a chloroplast precursor protein that directs the latter into chloroplasts and is subsequently cleaved off by the chloroplast processing protease.

The term "chloroplast-targeting sequence" refers to any polypeptide extension that is attached to the N-terminus of a foreign protein for the purpose of translocation into the chloroplast. In the case of a naturally occurring chloroplast precursor protein, the transit peptide is considered to be the chloroplast-targeting sequence, although optimal uptake and proteolytic processing may depend in part on portions of the "mature" chloroplast protein.

The term "transit peptide donor sequence" refers to that portion of the chloroplast-targeting sequence that is derived from the "mature" portion of the chloroplast precursor protein. The transit peptide donor sequence is always downstream and immediately adjacent to the transit peptide cleavage site that separates the transit peptide from the mature chloroplast protein.

The term "chloroplast processing protease" refers to a protease enzyme capable of cleaving the scissile bond between the transit peptide and the mature chloroplast protein.

The term "transit peptide cleavage site" refers to a site between two amino acids in a chloroplast-targeting sequence at which the chloroplast processing protease acts.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Mature" protein refers to a post-translationally processed polypeptide (i.e., one from which any pre- or pro-peptides in the primary translation product have been removed). "Precursor" protein refers to the primary product of translation of mRNA (i.e., with pre- and pro-peptides still present). Pre- and pro-peptides may be, but are not limited to, intracellular localization signals.

"Open reading frame" is abbreviated ORF.

"Polymerase chain reaction" is abbreviated PCR.

The terms "isolated nucleic acid fragment" or "isolated nucleic acid molecule" refer to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA, or synthetic DNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known (See Sambrook, J., Fritsch, E. F. and Maniatis, T. *Molecular Cloning: A Laboratory Manual*, Second Edition, Cold Spring Harbor Laboratory Press, Cold Spring Harbor (1989) (hereinafter "Maniatis"), particularly Chapter 11 and Table 11.1 therein). The conditions of temperature and ionic strength determine the "stringency" of the hybridization. Stringency conditions can be adjusted to screen for moderately similar fragments (such as homologous sequences from distantly related organisms) or to highly similar fragments (such as genes that duplicate functional enzymes from closely related organisms). Post-hybridization washes determine stringency conditions. For example a common set of stringent conditions consists of hybridization at 0.1×SSC, 0.1% SDS, 65° C. and washed with 2×SSC, 0.1% SDS followed by 0.1×SSC, 0.1% SDS.

One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Maniatis, supra, 9.50–9.51). For hybridizations with shorter nucleic acids (i.e., oligonucleotides), the position of mismatches becomes more important, and the length of the oligonucleotide determines its specificity (see Maniatis, supra, 11.7–11.8). In one embodiment the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the UDP-glucosyltransferase enzymes as set forth in SEQ ID NOs:18, 22, and 31. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence; "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The terms "bio-transformation" and "bio-conversion" are used interchangeably and will refer to the process of enzymatic conversion of a compound to another form or compound. The process of bio-conversion or bio-transformation is typically carried out by a biocatalyst.

The term "biocatalyst" refers to an enzyme or enzymes (either purified or present in a whole cell) capable of bioconverting a specific compound or compounds.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, Comput. *Methods Genome Res., [Proc. Int. Symp.]* (1994), Meeting Date 1992, 111–20. Editor(s): Suhai, Sandor. Publisher: Plenum, New York, N.Y.). Where sequence analysis software is used for analysis herein, the results of the analysis are based on the "default values" of the program referenced, unless otherwise specified. "Default values" mean any set of values or parameters that originally load with the software when first initialized.

The grape protein is 82% identical to the eucalyptus protein, and 75.5% and 75.1% identical to the *Citrus mitis* and *Citrus unshiu* proteins, respectively, at the amino acid sequence level, as detailed below.

GAP alignment (Wisconsin Package Version 9.0, Genetics Computer-Group (GCG), Madison, Wis.), of the grape and eucalyptus polypeptides over a length of 478 amino acids indicates that these two enzymes are 82% identical to each other. Accordingly, preferred are polypeptide fragments that are at least 82% identical to either of the above proteins at the amino acid sequence level. More preferred amino acid fragments are at least about 90% identical to the sequences herein. Most preferred amino acid fragments are those that are at least 95% identical to the sequences herein.

Similarly, preferred nucleic acid sequences encoding UDP-glucosyltransferase are those nucleic acid sequences encoding active proteins that are at least 82% identical to the nucleic acid sequences reported herein. More preferred UDP-glucosyltransferase nucleic acid fragments are those that encode proteins that are at least 90% identical to the sequences herein. Most preferred are UDP-glucosyltransferase nucleic acid fragments that encode proteins that are at least 95% identical to the nucleic acid fragments reported herein.

Specifically, it is within the scope of the invention to provide an isolated nucleic acid molecule comprising a nucleotide sequence encoding an UPD-glucosyltransferase enzyme that has at least 82% identity over a length of 478 amino acids based on the Gap method of alignment when compared to a polypeptide having the sequence as set forth in SEQ ID NO:18 or a nucleotide sequence comprising the complement of the first nucleotide sequence.

Similarly, it is within the scope of the invention to provide an isolated nucleic acid molecule comprising a nucleotide sequence encoding an UPD-glucosyltransferase enzyme that has at least 82% identity over length of 511 amino acids based on the Gap method of alignment when compared to a polypeptide having the sequence as set forth in SEQ ID NO:22 or a nucleotide sequence comprising the complement of the first nucleotide sequence.

Comparison of the grape and eucalyptus UDP-glucosyltransferase primary amino acid sequences to sequences that are available in the public domain reveals that the most similar protein is only 75% and 71% identical, respectively, to the above query sequences. However, it was not known at the time if this protein (a UDP-glucosyltransferase from *Citrus unshiu* (GenBank® Accession No. AB033758.1)), could glucosylate pHBA or even form ester glucosides. Indeed, the only substrate that was tested with this enzyme was a non-aromatic compound and glucose attachment was to a hydroxyl group, not a carboxyl group (Kita et al., *FEBS Lett* 469(2–3):173–178 (2000)). However, Applicants describe a closely related protein from *Citrus mitis* that is 98% identical to the previously described citrus GT and have shown that this enzyme catalyzes the formation of the pHBA glucose ester with similar properties to the Grape and Eucalyptus GTs. Furthermore, the primary amino acid sequence of the *Citrus mitis* GT is 75.5% and 72.1% identical to the Grape and Eucalyptus GTs, respectively. Therefore, also preferred are amino acid fragments that are at least 75.5% or 72.1% identical to the amino acid sequences set forth in SEQ ID NO:18 and SEQ ID NO:22, respectively.

Identification of UDP-Glucosyltransferase Homologs:

UDP-glucosyltransferase genes and gene products having the ability to convert pHBA to the pHBA ester glucoside include, but are not limited to, the grape UDP-glucosyltransferase (as defined by SEQ ID NOs:17–18), eucalyptus UDP-glucosyltransferase (as defined by SEQ ID NOs: 21–22), and citrus UDP-glucosyltransferase (as defined by SEQ ID NOs:30–31). Other UDP-glucosyltransferase genes having similar substrate specificity may be identified and isolated on the basis of sequence dependent protocols.

Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies such as polymerase chain reaction (PCR) (Mullis et al., U.S. Pat. No. 4,683,202), ligase chain reaction (LCR), (Tabor. et al., *Proc. Acad. Sci. USA* 82, 1074, (1985)), or strand displacement amplification (SDA, Walker et al., *Proc. Natl. Acad. Sci. U.S.A.*, 89, 392, (1992)).

For example, genes encoding similar proteins or polypeptides to the present UDP-glucosyltransferases could be isolated directly by using all or a portion of the nucleic acid fragments set forth in SEQ ID NOs:17, 21, and 30 or as DNA hybridization probes to screen libraries from any desired bacteria using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Typically, in PCR-type primer directed amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The Use of Oligonucleotide as Specific Hybridization Probes in the Diagnosis of Genetic Disorders", In *Human Genetic Diseases: A Practical Approach*, K. E. Davis, Ed.; IRL Press: Herndon, Va., 1986; pp. 33–50); Rychlik, W. "Methods in Molecular Biology", In *PCR Protocols: Current Methods and Applications*, White, B. A., Ed.; Humania Press: Totowa, N.J., 1993; Vol. 15, pages 31–39).

Generally, PCR primers may be used to amplify longer nucleic acid fragments encoding homologous genes from DNA or RNA. However, the polymerase chain reaction may also be performed on a library of cloned nucleic acid fragments wherein the sequence of one primer is derived from the instant nucleic acid fragments. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (GibcoBRL), specific 3' or 5' cDNA fragments can be isolated (Ohara et al., *PNAS USA* 86:5673 (1989); Loh et al., *Science* 243:217 (1989)).

Alternatively, the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically, a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically, the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur.

The higher the probe or target concentration the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Amersham Biosciences, Piscataway, N.J.) (about 300–500 kilodaltons), polyvinylpyrrolidone (about 250–500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA) or yeast RNA, and optionally from about 0.5 to 2% wt./vol. glycine. Other additives may also be included, such as volume exclusion agents that include a variety of polar water-soluble or swellable agents, such as polyethylene glycol, anionic polymers such as polyacrylate or polymethylacrylate and anionic saccharidic polymers, such as dextran sulfate.

Plant Expression;

The plant species suitable for expression of the disclosed sequences include, but are not limited to, grape (*Vitis* sp.), eucalyptus (*Eucalyptus grandis*), tobacco (*Nicotiana* spp.), tomato (*Lycopersicon* spp.), potato (*Solanum* spp.), hemp (*Cannabis* spp.), sunflower (*Helianthus* spp.), sorghum (*Sorghum vulgare*), wheat (*Triticum* spp.), maize (*Zea mays*), rice (*Oryza sativa*), rye (*Secale cereale*), oats (*Avena* spp.), barley (*Hordeum vulgare*), rapeseed (*Brassica* spp.), broad bean (*Vicia faba*), french bean (*Phaseolus vulgaris*), other bean species (*Vigna* spp.), lentil (*Lens culinaris*), soybean (*Glycine max*), arabidopsis (*Arabidopsis thaliana*), guayule (*Parthenium argentatum*), cotton (*Gossypium hirsutum*), petunia (*Petunia hybrida*), flax (*Linum usitatissimum*), and carrot (*Daucus carota sativa*), sugarbeet (*Beta* spp.), sugarcane (*Saccharum* spp.), kenaf (*Hibiscus cannabinus L*), castor (*Ricinus* spp.), miscanthus (*Miscanthus* spp.), and Elephant grass (*Pennisetum* spp.). Preferred hosts are eucalyptus (*Eucalyptus grandis*), tobacco (*Nicotiana* spp.), arabidopsis (*Arabidopsis thaliana*), sugarbeet (*Beta* spp.), sugarcane (*Saccharum* spp.), kenaf (*Hibiscus cannabinus L*), castor (*Ricinus* spp.), miscanthus (*Miscanthus* spp.), and Elephant grass (*Pennisetum* spp.).

Overexpression of the present UDP-glucosyltransferase homologs may be accomplished by first constructing a chimeric gene in which their coding region is operably-linked to a promoter that directs the expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The present chimeric genes may also comprise one or more introns in order to facilitate gene expression.

Plasmid vectors comprising the present chimeric genes can then be constructed. The choice of a plasmid vector depends upon the method that will be used to transform host plants. The skilled artisan is well aware of the genetic elements that must be present on the plasmid vector in order to successfully transform, select, and propagate host cells containing the chimeric gene. For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a UDP-glucosyltransferase gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin-1 promoter, the Smas promoter, the cinnamyl alcohol dehydrogenase promoter (U.S. Pat. No. 5,683,439), the Nos promoter, the pEmu promoter, the rubisco promoter, and the GRP1-8 promoter.

Alternatively, the plant promoter can direct expression of the UDP-glucosyltransferase gene in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther-specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the instant UDP-glucosyltransferase gene. These promoters can also be used, for example, in recombinant expression cassettes to drive expression of antisense nucleic acids to reduce, increase, or alter concentration and/or composition of the UDP-glucosyltransferase protein in a desired tissue. Thus, in some embodiments, the nucleic acid construct will comprise a promoter functional in a plant cell, such as in *Zea mays* or tobacco, operably linked to an UDP-glucosyltransferase biosynthetic gene. Gene promoters useful in these embodiments include the endogenous promoters driving expression of the UDP-glucosyltransferase proteins.

In some embodiments, isolated nucleic acids which serve as promoter or enhancer elements can be introduced in the appropriate position (generally upstream) of a non-heterologous form of the UDP-glucosyltransferase polynucleotides so as to up or down regulate its expression. For example, endogenous promoters can be altered in vivo by mutation, deletion, and/or substitution (see Kmiec, U.S. Pat. No. 5,565,350; Zarling et al., PCT/US93/03868), or isolated promoters can be introduced into a plant cell in the proper orientation and distance from the UDP-glucosyltransferase genes so as to control the expression of the gene. Expression of the UDP-glucosyltransferase genes can be modulated under conditions suitable for plant growth so as to alter the total concentration and/or alter the composition of UDP-glucosyltransferase proteins in a plant cell. Thus, the present invention provides compositions and methods for making heterologous promoters and/or enhancers operably linked to a native, endogenous (i.e., non-heterologous) form of UDP-glucosyltransferase proteins.

Where UDP-glucosyltransferase polypeptide expression is desired, a polyadenylation region at the 3'-end of a polynucleotide coding region of the UDP-glucosyltransferase genes is generally included. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395–4405(1988); Callis et al., *Genes Dev.* 1:1183–1200 (1987)). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994). The vector comprising the UDP-glucosyltransferase sequence will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., *Meth. Enzymol.* 153:253–277 (1987).

Transfection or Transformation Methods:

Optionally, the UDP-glucosyltransferase gene may be introduced into a plant. Generally, the gene will first be incorporated into a recombinant expression cassette or vector, by a variety of methods known in the art (See, for example, Weising et al., *Ann. Rev. Genet.* 22:421–477 (1988). For example, the DNA construct may be introduced directly into the genomic DNA of the plant cell using techniques such as electroporation, polyethylene glycol (PEG) precipitation, poration, particle bombardment, silicon fiber delivery, or microinjection of plant cell protoplasts or embryogenic callus (See, for example, Tomes et al., "Direct DNA Transfer into Intact Plant Cells via Microprojectile Bombardment", In *Plant Cell, Tissue and Organ Culture, Fundamental Methods*, O. L. Gamborg and G. C. Phillips, Eds.; Springer-Verlag Berlin Heidelberg: New York, 1995; pp 197–213. The introduction of DNA constructs using PEG precipitation is described in Paszkowski et al., *Embo J.* 3:2717–2722 (1984). Electroporation techniques are described in Fromm et al., *Proc. Natl. Acad. Sci. (USA)* 82:5824 (1985). Biolistic transformation techniques are described in Klein et al., *Nature* 327:70–73 (1987). For example, biolistic transformation of *Hevea brasiliensis* is described in U.S. Pat. No. 5,580,768.).

Alternatively, *Agrobacterium tumefaciens*-mediated transformation techniques may be used. See, for example Horsch et al., *Science* 233:496–498 (1984); Fraley et al., *Proc. Natl. Acad. Sci. (USA)* 80:4803 (1983); and *Plant Molecular Biology: A Laboratory Manual*, Chapter 8, Clark, Ed.; Springer-Verlag: Berlin, 1997. The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria (U.S. Pat. No. 5,591,616). Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (e.g., Lichtenstein and Fuller, In *Genetic Engineering*, P W J Rigby, Ed.; Academic Press: London, 1987, vol. 6; and Lichtenstein, C. P., and Draper, J. In *DNA Cloning*, Vol. 11, D. M. Glover, Ed.; IRI Press: Oxford, 1985); Application PCT/US87/02512 (WO 88/02405 published Apr. 7, 1988) describes the use of *A. rhizogenes* strain A4 and its Ri plasmid along with *A. tumefaciens* vectors pARC8 or pARC16) (2) liposome-mediated DNA uptake (e.g., Freeman et al., *Plant Cell Physiol.* 25:1353 (1984)), (3) the vortexing method (e.g., Kindle, *Proc. Natl. Acad. Sci., (USA)* 87:1228 (1990)).

Regeneration and Propagation Techniques

Plant cells directly resulting or derived from the nucleic acid introduction techniques can be cultured to regenerate a whole plant which possesses the introduced genotype. Such regeneration techniques often rely on manipulation of certain phytohormones in a tissue culture growth medium. Plants cells can be regenerated (e.g., from single cells, callus tissue, leaf discs, or other organs) according to standard plant tissue culture techniques from almost any plant to obtain an entire plant. Plant regeneration from cultured protoplasts is described by Evans et al., In *Protoplasts Isolation and Culture: Handbook of Plant Cell Culture*, Macmillan Publishing Company: New York, 1983, pp 124–176: and *Binding, Regeneration of Plants, Plant Protoplasts*, CRC Press: Boca Raton, 1985, pp 21–73.

The regeneration of plants from either single plant protoplasts or various explants is well known in the art. (See, for example, *Methods for Plant Molecular Biology*, A. Weissbach and H. Weissbach, Eds., Academic Press, Inc.: San Diego, 1988.) This regeneration and growth process includes the steps of selection of transformant cells and shoots, rooting the transformant shoots, and growth of the plantlets in soil. For maize cell culture and regeneration see generally, *The Maize Handbook*, Freeling and Walbot, Eds., Springer: New York, 1994; *Corn and Corn Improvement*, $3^{rd}$ edition, Sprague and Dudley Eds., American Society of Agronomy: Madison, Wis., 1988. For transformation and regeneration of maize see, Gordon-Kamm et al., *The Plant Cell*, 2:603–618 (1990).

The regeneration of plants containing the UDP-glucosyltransferase gene and introduction by Agrobacterium from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., (*Proc. Natl. Acad. Sci.* (*U.S.A.*), 80:4803 (1983)). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

After the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Confirmation of Protein Expression

Transgenic plants expressing the UDP-glucosyltransferase gene can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Localization and Modification of Gene Expression

For some applications it may be useful to direct the UDP-glucosyltransferase enzyme to different cellular compartments or to facilitate their secretion from the cell. The chimeric genes described above may be further modified by the addition of appropriate intracellular or extracellular targeting sequence to their coding regions. These include chloroplast transit peptides (Keegstra et al., *Cell* 56:247–253 (1989)), signal sequences that direct proteins to the endoplasmic reticulum (Chrispeels et al., *Ann. Rev. Plant Phys. Plant Mol.* 42:21–53 (1991)), and nuclear localization signals (Raikhel et al., *Plant Phys.* 100:1627–1632 (1992)). While the references cited give examples of each of these, the list is not exhaustive and more targeting signals of utility may be discovered in the future.

It may also be desirable to reduce or eliminate expression of the UDP-glucosyltransferase genes in plants for some applications. In order to accomplish this, chimeric genes designed for antisense or co-suppression of UDP-glucosyltransferase homologs can be constructed by linking the genes or gene fragments encoding parts of these enzymes to plant promoter sequences. Thus, chimeric genes designed to express antisense RNA for all or part of a UDP-glucosyltransferase homolog can be constructed by linking the UDP-glucosyltransferase homolog genes or gene fragments in reverse orientation to plant promoter sequences. The co-suppression of antisense chimeric gene constructs could be introduced into plants via well known transformation protocols wherein expression of the corresponding endogenous genes are reduced or eliminated.

One of the principal utilities for the present UDP-glucosyltransferase enzymes is the conjugation of benzoic acid monomers to glucose for the accumulation of the glucoside in plant vacuoles. Of particular interest in the present invention are the glucosides of pHBA and similar monomers.

pHBA is a naturally-occurring compound in all plants that have been examined. For example, pHBA has been found in carrot tissue (Schnitzler et al., *Planta*, 188, 594, (1992)), in a variety of grasses and crop plants (Lydon et al., *J. Agric. Food. Chem.*, 36, 813, (1988)), in the lignin of poplar trees (Terashima et al., *Phytochemistry*, 14, 1991, (1972)), and in a number of other plant tissues (Billek et al., *Oesterr. Chem.*, 67, 401, (1966)).

Although naturally occurring in plants, levels of pHBA are far too small to be commercially useful. Higher levels of pHBA may only be obtained by over-expression of genes that comprise the native phenylpropenoid pathway, or by the introduction of foreign genes, the expression of which will enhance the levels of pHBA in plant tissue. Focusing on the latter approach, there are at least two bacterial enzymes that have been shown to be effective in the enhancement of pHBA levels in plants. One is the gene encoding bacterial chorismate pyruvate lyase (CPL), which catalyzes a direct conversion of chorismate to pyruvate and pHBA. The other is 4-hydroxycinnamoyl-CoA hydratase/lyase (HCHL), which converts the CoA ester of p-hydroxycinnamic acid (pHCA-CoA) to p-hydroxybenaldehyde, a substantial portion of which is subsequently further oxidized to pHBA through an unknown mechanism. The HCHL-mediated production of p-hydroxybenzaldehyde takes place in the plant cytosol, whereas CPL-mediated formation of pHBA occurs in chloroplasts and other plastids.

The introduction and over-expression of either or both of these genes into plants under the correct conditions will enhance the levels of pHBA in plant tissue (Siebert et al., *Plant Physiol.* 112:811–819 (1996); Mayer et al., *Plant Cell* 13(7):1669–1682 (2001)). Co-expression of CPL and/or HCHL with the UDP-glucosyltransferases of the present invention have been shown to increase the levels of recoverable pHBA ester glucoside. Additionally, converting pHBA exclusively to the ester glucoside leads to higher levels of total product accumulation, which has obvious commercial significance.

Genes encoding CPL have been described. The most notable is the *E. coli* ubiC gene, which was independently cloned by two different groups (Siebert et al., *FEBS Lett* 307:347–350 (1992); Nichols et al., *J. Bacteriol* 174:5309–5316 (1992)). An *E. coli* CPL gene fused at its 5' end to a nucleic acid sequence that codes for an N-terminal chloroplast targeting sequence is designated herein as having SEQ ID NO:41. This chimeric gene encodes a chloroplast-targeted *E. coli* CPL fusion protein with the amino acid sequence set forth in SEQ ID NO:42. Similarly, a gene encoding HCHL has been isolated from *Pseudomonas putida* HCHL gene (Mukeim and Learch, *Appl. Microbiol. Biotechnol.* 51:456–461 (1999)). This HCHL gene is designated herein as SEQ ID NO:45, encoding a polypeptide having the amino acid sequence as set forth in SEQ ID NO:46.

It is well within the grasp of the skilled person to clone these and other genes involved in the phenylpropenoid pathway into plants to enhance the levels of pHBA or other desirable hydroxybenzoic acid derivatives. It is equally within the purview of the skilled person to co-express these genes with the UDP-glucosyltransferases of the present invention, as taught above, to produce high levels of pHBA ester glucoside in plant tissue.

Microbial Expression:

The genes and gene products of the UDP-glucosyltransferase sequences may be introduced into microbial host cells. Preferred host cells for expression of the instant genes and nucleic acid molecules are microbial hosts that can be found broadly within the fungal or bacterial families and which grow over a wide range of temperature, pH values, and solvent tolerances. Because transcription, translation, and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and saturated hydrocarbons (such as methane or carbon dioxide in the case of photosynthetic or chemoautotrophic hosts). However, the functional genes may be regulated, repressed, or depressed by specific growth conditions (such as the form and amount of nitrogen, phosphorous, sulfur, oxygen, carbon, or any trace micronutrient including small inorganic ions). In addition, the regulation of functional genes may be achieved by the presence or absence of specific regulatory molecules that are added to the culture and are not typically considered nutrient or energy sources. Growth rate may also be an important regulatory factor in gene expression. Examples of suitable host strains include, but are not limited to, fungal or yeast species (such as *Aspergillus, Trichoderma, Saccharomyces, Pichia, Candida, Hansenula*), or bacterial species (such as *Salmonella, Bacillus, Acinetobacter, Rhodococcus, Streptomyces, Escherichia, Pseudomonas, Methylomonas, Methylobacter, Alcaligenes, Synechocystis, Anabaena, Agrobacterium, Thiobacillus, Methanobacterium, Klebsiella, Burkholderia, Sphingomonas, Paracoccus, Pandoraea, Deiftia*, and *Comamonas*). Preferred microbial hosts are *Escherichia, Klebsiella, Salmonella, Agrobacterium, Saccharomyces, Pichia, Pseudomonas*, and *Bacillus*.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high level expression of the enzymes.

Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene that harbors transcriptional initiation controls and a region 3' of the DNA fragment that controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters (useful for expression in *Bacillus*).

Termination control regions may also be derived from various genes native to the preferred hosts. Optionally, a termination site may be unnecessary, however, it is most preferred if included.

Once a suitable expression cassette is constructed comprising a UDP-glucosyltransferase it may be used to transform a suitable host for use in the present method. The host can then be used to preferentially catalyze the formation of the pHBA ester glucoside or other glucose esters of appropriate aromatic compounds.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as carbon dioxide. Batch and Fed-Batch culturing methods are common and well known in the art and examples may be found in Thomas D. Brock, In *Biotechnology: A Textbook of Industrial Microbiology*, Second Edition (1989) Sinauer Associates, Inc., Sunderland, Mass., or Deshpande, Mukund V., *Appl. Biochem. Biotechnol.* 36:227 (1992), herein incorporated by reference.

Commercial production may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Enzyme Properties

The starting point to identify an enzyme that efficiently uses pHBA as a substrate was the Brassica SA-GT. This enzyme efficiently uses sinapic acid as a substrate and only attaches glucose to the carboxyl group of this compound. Applicants sought to identify an enzyme that was an efficient catalyst for a substrate that the SA-GT handled very poorly (i.e., pHBA). Therefore, analysis of those two substrates (sinapic acid, pHBA) was the starting point for discovery of enzymes that were efficient catalysts for pHBA. The ratio of the activities for 10 mM pHBA and 10 mM sinapic acid was an important factor to measure how much better the newly identified enzymes worked with pHBA. In addition, a high catalytic turnover number ($k_{cat}$) with pHBA as a substrate was an extremely important factor for the in vivo plant applications that Applicants envision, since the foreign glucosyltransferase will have to effectively compete with and overwhelm the naturally occurring glucosyltransferase activities in the plant host.

Turnover number for the present enzyme is determined according to principles well known in the art. For example, at saturating [pHBA] as fit by the Michaelis-Menten equation one can determine $V_{max}$ of product formation in a format of µmol/sec/protein concentration. Using the protein concentration as determined in µmols in the assay, one can determine how many µmols product are formed using 1.0 µmols enzyme in a fixed time period such as a second (i.e., how many times catalytic turnover occurred). For example, 2 µmols of the grape GT would form 21.8 µmols pHBA ester glucoside under the conditions described, and thus the turnover number ($k_{cat}$)=10.9 per second.

The UDP-glucosyltransferase enzymes of the present invention possess unique properties. For example, the present polypeptides (identified as SEQ ID NOs:18, 22, and 31) have a substrate preference for pHBA over sinapic acid (a hydroxycinnamic acid derivative) that ranges from 4.88 fold for the *Citrus mitis* GT to 37.7 fold for the Grape GT.

Furthermore, the turnover numbers for these enzymes are particularly high for pHBA: (Grape ~10.9 sec$^{-1}$, Euc ~15.45 sec$^{-1}$, Citrus ~1.77 sec$^{-1}$ at saturating concentrations of pHBA.

Accordingly, UPD-glucosyltransferase enzymes and genes encoding the same are within the scope of the invention if the enzyme: a) encodes a polypeptide having at least 75% identity to the UDP-glucosyltransferase having the amino acid sequence as set forth in SEQ ID NO:18; or at least 72% identity to the UDP-glucosyltransferase having the amino acid sequence as set forth in SEQ ID NO:22; b) catalyzes the production of pHBA ester glucoside from pHBA; c) has at least a 4.88-fold substrate preference for pHBA over sinapic acid at a 10 mM substrate concentration; and d) has a maximum turnover number of at least 1.77 sec$^{-1}$ for the conversion of pHBA to pHBA ester glucoside.

Thus, preferred enzymes are those that have the above-listed properties b)–d) and are a least 75% identical to the Grape GT polypeptide (SEQ ID NO:18). More preferred enzymes are those that have the above-listed properties b)–d) and are at least 80% identical to the Grape GT polypeptide (SEQ ID NO:18). Most preferred enzymes are those that have the above-listed properties b)–d) and are at least 90% identical to the Grape GT polypeptide (SEQ ID NO:18).

Similarly, preferred enzymes are those that have the above-listed properties b)–d) and are at least 72% identical to the Eucalyptus GT polypeptide (SEQ ID NO:22). More preferred enzymes are those that have the above-listed properties b)–d) and are at least 80% identical to the Eucalyptus GT polypeptide (SEQ ID NO:22). Most preferred enzymes are those that have the above-listed properties b)–d) and are at least 90% identical to the Eucalyptus GT polypeptide (SEQ ID NO:22).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make changes and modifications of the invention to adapt it to various usages and conditions.

General Methods

Techniques suitable for use in the following examples including standard recombinant DNA and molecular cloning techniques are well known in the art (See Maniatis, supra, and Silhavy, T. J., Bennan, M. L. and Enquist, L. W., *Experiments with Gene Fusions*, Cold Spring Harbor Laboratory Cold Press Spring Harbor, N.Y. (1984); and Ausubel, F. M. et al., *Current Protocols in Molecular Biology*, published by Greene Publishing Assoc. and Wiley-Interscience (1987).

Materials and methods suitable for the maintenance and growth of bacterial cultures are well known in the art. Techniques suitable for use in the following examples may be found as set out In *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds.), American Society for Microbiology, Washington, D.C. (1994)); or by Thomas D. Brock In *Biotechnology: A Textbook of Industrial Microbiology*, Second Edition, Sinauer Associates, Inc., Sunderland, Mass. (1989). All reagents and materials used for the growth and maintenance of bacterial cells were obtained from Aldrich Chemicals (Milwaukee, Wis.), DIFCO Laboratories (Detroit, Mich.), GibcoBRL-Life Technologies (Rockville, Md.), or Sigma Aldrich Chemical Company (St. Louis, Mo.) unless otherwise specified.

The meaning of abbreviations is as follows: "h" means hour(s), "min" means minute(s), "sec" means second(s), "d" means day(s), "µl" means microliter, "mL" means milliliters, "L" means liters, "µm" means micrometer, "ppm" means parts per million (i.e., milligrams per liter).

Example 1

PCR-Amplification of the *Brassica napus* SA-GT gene and Preparation of the Plasmid Construct Used for Expression in *Escherichia coli*

Two PCR primers were used to amplify the *Brassica napus* SA-GT from genomic DNA, while adding unique restriction sites to its flanking regions for subsequent ligation into an *Escherichia coli* expression vector. The target gene codes for a UDP-glucosyltransferase (GenBank® Accession number AF287143) that catalyzes the transfer of glucose from UDP-glucose to the carboxyl group of sinapic acid and several other hydroxycinnamic acid derivatives; this information was included as part of the annotation of the original GenBank® submission. The primers used to PCR-amplify the *Brassica napus* SA-GT consisted of the following nucleotides:

```
Primer 1- 5'-CTA CTC ATT Tca tat gGA ACT ATC ATC TTC TCC TT-3'    (SEQ ID NO:1)

Primer 2- 5'-CAT CTT ACT gga tcc TTA TGA CTT TTG CAA TAA AAG TTT T-3' (SEQ ID NO:2)
```

The underlined bases hybridize to the target gene, while lower case letters indicate the restriction sites (NdeI or BamHI) that were added to the ends of the PCR primers. The target gene was amplified using Primers 1 and 2, and genomic DNA that was isolated from leaf tissue of 14-day-old *Brassica napus* (Westar) seedlings. Primer 1 hybridizes at the start of the gene and introduces a NdeI site at the protein's initiation codon, while Primer 2 hybridizes at the opposite end and provides a BamHI site just past the termination codon. The 100-µL PCR reaction contained 5 µL of the genomic DNA preparation, 5 units of Pfu Turbo® DNA Polymerase (Stratagene, La Jolla, Calif.), 100 µM each dNTP, and both PCR primers at a final concentration of 0.2 µM. The reaction also contained 10 mM KCl, 10 mM $(NH_4)_2SO_4$, 20 mM Tris-HCl (pH 8.75), 2 mM $MgSO_4$, 0.1% Triton X-100, and 0.1 mg/mL of bovine serum albumen. Amplification was carried out in a DNA Thermocycler 480 (Perkin Elmer, Boston, Mass.) for 30 cycles, each comprising 1 min at 94° C., 1 min at 55° C., and 3 min at 70° C. Following the last cycle, there was 7-min extension period at 72° C.

The PCR product was cut with NdeI and BamHI. The resulting fragment was ligated into the *Escherichia coli* expression vector, pET-24a(+) (Novagen, Madison, Wis.) that had been digested with the same restriction enzymes. The ligation reaction mixture was used to transform *Escherichia coli* DH10B electrocompetent cells (GibcoBRL-Life Technologies, Rockville, Md.) using a BTX Transfector 100 (Biotechnologies and Experimental Research Inc., San Diego, Calif.) according to the manufacturer's protocol; growth was selected on LB media that contained kanamycin (50 µg/mL). Transformants that contained plasmids with inserts were identified through restriction digestion analysis using NdeI and BamHI to release the fragment. Plasmid DNA from a representative colony was sequenced completely and subsequently introduced into *Escherichia coli* BL21 (DE3) for expression of the recombinant protein. The plasmid selected for further manipulation is referred to below as "pET24a/SA-GT". The nucleotide sequence of the ORF of the PCR-amplified *Brassica napus* SA-GT in the pET24a *Escherichia coli* expression construct and its predicted primary amino acid sequence are set forth in SEQ ID NO:3 and SEQ ID NO:4, respectively. Note that the coding region is not identical to the ORF that is given in GenBank® accession number AF287143. Although both proteins contain 497 residues, they are only 97.4% identical at the amino acid sequence level. The most likely explanation for this anomaly is that the two proteins are either closely related isozymes from the same cultivar, or that they represent different cultivars.

Example 2

Cloning of Three *Arabidopsis* UDP-Glucosvitransferases (GT 3, GT 4, and GT 5) Closely Related to *Brassica napus* SA-GT Two PCR primers were used to amplify an arabidopsis glucosyltransferase gene that corresponds to the nucleotide sequence given in GenBank® Accession number AL161541.2. The target for amplification was a cDNA clone (acs2c.pk012.b7) that was identified in Applicants' EST database. The primers used for this purpose consisted of the following nucleotides:

```
Primer 3-
                                        (SEQ ID NO:5)
5'-CCA TAT GAG tca tga TGT TCG AAA CTT G-3'

Primer 4-
                                        (SEQ ID NO:6)
5'-GTC AAA GAC gtc gac CTA GTA TCC-3'
```

The underlined bases hybridize to the target gene, while lower case letters indicate the restriction sites (PagI or SalI) that were added to the ends of the PCR primers. Primer 3 hybridizes at the start of the gene and introduces a PagI site at the protein's initiation codon, while Primer 4 hybridizes at the opposite end and provides a SalI site just past the termination codon. The PCR reaction contained 50 mM KCl, 10 mM Tris-HCl (pH 9), 0.1% Triton X-100, 2.5 mM $MgCl_2$, 0.2 mM each dNTP, 5 units of Taq polymerase (MBI Fermentas, Hanover, Md.), 10 ng of the cDNA plasmid template and both PCR primers at a final concentration of 0.2 µM. Amplification was carried out for 25 cycles, each comprising 1.5 min at 94° C., 1.5 min at 55° C., and 2.5 min at 72° C. The PCR product was digested with PagI and SalI, gel-purified, and the resulting fragment was ligated into the Escherichia coli expression vector, pET-28a(+) (Novagen) that was digested with the same restriction enzymes. The ligation reaction mixture was used to transform Escherichia coli DH10B, and plasmid DNA from a representative colony was sequenced completely to check for PCR errors; none were found. The plasmid selected for further manipulation is referred to below as "pET28a/GT 3". The nucleotide sequence of the ORF for the PCR-amplified Arabidopsis GT 3 in the pET28a expression construct and its predicted primary amino acid sequence are set forth in SEQ ID NO:7 and SEQ ID NO:8, respectively. The primary amino acid sequence of the ORF encoded for by the PCR-amplified GT 3 DNA fragment in pET28a (e.g., SEQ ID NO:8) is identical to the predicted ORF of the arabidopsis protein encoded by GenBank® accession number AL161541.2, with the exception of the second amino acid which was changed from a valine to a methionine residue as a consequence of the PCR strategy. For protein expression, the purified plasmid (pET28a/GT 3) was introduced into Escherichia coli BL21 (DE2) cells (Novagen).

Two PCR primers were used to amplify an arabidopsis glucosyltransferase gene that corresponds to the nucleotide sequence given in GenBank® accession number AL161541. The target for amplification was a cDNA clone (acs2c.pk006.m9) that was identified in Applicants' EST database. The primers used for this purpose consisted of the following nucleotides:

```
                                          (SEQ ID NO:9)
Primer 5- 5'-CTA GAA ATt cat gaA CCC GTC TCG TCA-3'

(SEQ ID NO:10)
Primer 6- 5'-GAC ATC Agt cga cCT AGT GTT CTC C-3'
```

The underlined bases hybridize to the target gene, while lower case letters indicate the restriction sites (PagI or SalI) that were added to the ends of the PCR primers. Primer 5 hybridizes at the start of the gene and introduces a PagI site at the protein's initiation codon, while Primer 6 hybridizes at the opposite end and provides a SalI site just past the termination codon. The PCR reaction contained 50 mM KCl, 10 mM Tris-HCl (pH 9), 0.1% Triton X-100, 2.5 mM $MgCl_2$, 0.2 mM each dNTP, 5 units of Taq polymerase (MBI Fermentas), 10 ng of the cDNA plasmid template and both PCR primers at a final concentration of 0.2 µM. Amplification was carried out for 25 cycles, each comprising 1.5 min at 94° C., 1.5 min at 55° C., and 2.5 min at 72° C. The PCR product was digested with PagI and SalI, gel-purified, and the resulting fragment was ligated into the Escherichia coli expression vector, pET-28a(+) (Novagen) that was digested with the same restriction enzymes. The ligation reaction mixture was used to transform Escherichia coli DH10B. Plasmid DNA from a representative colony was sequenced completely to check for PCR errors; none were found. The plasmid selected for further manipulation is referred to below as "pET28a/GT 4". The nucleotide sequence of the ORF for the PCR-amplified Arabidopsis GT 4 in the pET28a expression construct and its predicted primary amino acid sequence are set forth in SEQ ID NO:11 and SEQ ID NO:12, respectively. The primary amino acid sequence of the ORF encoded for by the PCR-amplified GT 4 DNA fragment in pET28a (e.g., SEQ ID NO:12) is identical to the predicted ORF of the arabidopsis protein encoded by GenBank® accession number AL161541, with the exception of the second amino acid which was changed from an aspartic acid to an asparagine residue as a consequence of the PCR strategy. For protein expression, the purified plasmid (pET28a/GT 4) was introduced into Escherichia coli BL21 (DE2) cells (Novagen).

Two PCR primers were used to amplify an arabidopsis glucosyltransferase gene that corresponds to the nucleotide sequence given in GenBank® accession number AL161541.2. Arabidopsis genomic DNA was used as a template for amplification. The primers used for this purpose consisted of the following nucleotides:

```
Primer 7-
                                          (SEQ ID NO:13)
    5'-CAA AAA AAA AAt cat gaA GAT GGA ATC GT-3'

Primer 8-
                                          (SEQ ID NO:14)
    5'-ATA TTg tcg acT TAC ACG ACA TTA TTA AT-3'
```

The underlined bases hybridize to the target gene, while lower case letters indicate the restriction sites (PagI or SalI) that were added to the ends of the PCR primers. Primer 7 hybridizes at the start of the gene and introduces a PagI site at the protein's initiation codon, while Primer 8 hybridizes at the opposite end and provides a SalI site just past the termination codon. The PCR reaction contained 50 mM KCl, 10 mM Tris-HCl (pH 9), 0.1% Triton X-100, 2.5 mM $MgCl_2$, 0.2 mM each dNTP, 5 units of Taq polymerase (MBI Fermentas), 10 ng of the cDNA plasmid template and both PCR primers at a final concentration of 0.2 µM. Amplification was carried out for 25 cycles, each comprising 1.5 min at 94° C., 1.5 min at 55° C., and 2.5 min at 72° C. The PCR product was digested with PagI and SalI, gel-purified, and the resulting fragment was ligated into the Escherichia coli expression vector, pET-28a(+) (Novagen) that was digested with the same restriction enzymes. The ligation reaction mixture was used to transform Escherichia coli DH10B. Plasmid DNA from a representative colony was sequenced completely to check for PCR errors; none were found. The plasmid selected for further manipulation is referred to below as "pET28a/GT 5". The nucleotide sequence of the ORF for the PCR-amplified Arabidopsis GT 5 in the pET28a expression construct and its predicted primary amino acid sequence are set forth in SEQ ID NO:15 and SEQ ID NO:16, respectively. The primary amino acid sequence of the ORF encoded for by the PCR-amplified GT 5 DNA fragment in pET28a (e.g., SEQ ID NO:16) is identical to the predicted ORF of the arabidopsis protein encoded by GenBank® accession number AL161541.2, with the exception of the second amino acid which was changed from an glutamic acid to a lysine residue as a consequence of the PCR strategy. For protein expression, the purified plasmid (pET28a/GT 5) was introduced into Escherichia coli BL21 (DE2) cells (Novagen).

Example 3

Identification of the Grape GT and Preparation of the Plasmid Construct Used for Expression in Escherichia coli To try to identify a plant glucosyltransferase that exclusively catalyzes the formation of glucose esters and has a high turnover number with pHBA as a substrate, the first 246 N-terminal amino acid residues of the Brassica napus SA- GT (SEQ ID NO:4) (GenBank® accession number AF287143) were used as a query sequence to probe Applicants' proprietary EST database. The tBlastn algorithm (Altschul et al., *Nucleic Acids Res.* 25:3389–3403 (1997)) with the standard default settings was employed for this search. Apart from two arabidopsis ESTs that correspond to sequences that are available in the public domain, the clone (vmb1na.pk009.c8) with the highest degree of homology (63/115 identical amino acid residues, $E=1e^{-43}$) was obtained from a normalized cDNA library that was prepared from midstage grape berries (*Vitis* sp.). Since the cDNA insert in the plasmid vector appeared to be a full-length clone, it was selected for further characterization and sequenced completely. The nucleotide sequence of the ORF in vmb1na.pk009.c8 and its predicted primary amino acid sequence are set forth in SEQ ID NO:17 and SEQ ID NO:18, respectively. As shown in Table 1, the full-length grape protein (henceforth referred to as the "Grape GT") is 56% identical to the *Brassica napus* SA-GT when the two proteins are aligned by the gap method using the standard default settings.

TABLE 1

| Glucosyltransferase | % Identity to Brassica SA-GT |
|---|---|
| Brassica SA-GT | 100 |
| Arabidopsis GT 3 | 66 |
| Arabidopsis GT 4 | 66 |
| Arabidopsis GT 5 | 67 |
| Grape GT | 56 |

The flanking regions of the ORF of the Grape GT were modified by PCR for insertion into the high-level *Escherichia coli* expression vector, pET24a(+) (Novagen). This insertion was accomplished using primers 9 and 10 and purified plasmid DNA from the original cDNA clone as the target for amplification.

10 and individual resuspended colonies as the source of template for amplification. Plasmid DNA was isolated from a representative colony and the insert was sequenced completely to confirm the absence of PCR errors. This plasmid was used for protein production in *Escherichia coli* and is referred to below as "pET24a/Grape GT".

Example 4

Characterization of Plant UDP-Glucosyltransferases with pHBA and Sinapic Acid as Substrates To identify a plant UDP-glucosyltransferase that exclusively catalyzes the formation of glucose esters and has high catalytic activity with pHBA as a substrate, Applicants used the primary amino acid sequence of the *Brassica napus* SA-GT (SEQ ID NO:4) (GenBank® accession number AF287143)) as a query sequence to narrow the hunt for candidates that might carry out the desired reaction. Although there was no other information available to Applicants at the time, the original GenBank® submission clearly stated that the *Brassica* SA-GT protein is able to transfer glucose from UDP-glucose to the carboxyl group of sinapic acid and several other hydroxycinnamic acid derivatives. Applicants therefore focused their attention on this protein and four closely related homologs, hoping that at least one of them would glucosylate the carboxyl group of pHBA. As already noted, the three arabidopsis proteins (GT 3, GT 4, and GT 5) were already available in the public domain, but at the time nothing was known about the reactions they catalyzed or their substrate specificities. The Grape GT was identified in a BLAST search of Applicants' EST database and its function was also unknown. As shown in Table 1, GT 3, GT 4, GT5, and the Grape GT are respectively 66%, 66%, 67%, and 56% identical to the Brassica SA-GT protein at the primary amino acid sequence level.

To test the activity of these proteins with pHBA and sinapic acid as substrates, the *Escherichia coli* expression

```
Primer 9-   5'-CTA CTC ATT Tca tat gGG ATC TGA ATC AAA GCT AG-3'    (SEQ ID NO:19)

Primer 10-  5'-CAT CTT ACT gga tcc ACT TCA CAC GTG TCC CTT CAA-3'   (SEQ ID NO:20)
```

The underlined bases hybridize to the target gene, while lower case letters indicate the restriction sites (NdeI or BamHI) that were added to the ends of the PCR primers. Primer 9 hybridizes at the start of the gene and introduces an NdeI site at the initiation codon, while Primer 10 hybridizes at the opposite end and provides a BamHI site just after the stop codon. The 100-μL PCR reaction contained ~100 ng of purified plasmid DNA, 5 units of Pfu Turbo® DNA Polymerase (Stratagene), 100 μM each dNTP, and both PCR primers at a final concentration of 0.2 μM. The reaction also contained 10 mM KCl, 10 mM $(NH_4)_2SO_4$, 20 mM Tris-HCl (pH 8.75), 2 mM $MgSO_4$, 0.1% Triton X-100, and 0.1 mg/mL of bovine serum albumen. Amplification was carried out in a DNA Thermocycler 480 (Perkin Elmer) for 25 cycles, each comprising 1 min at 94° C., 1 min at 55° C., and 2 min at 70° C. Following the last cycle, there was 10-min extension period at 72° C. The PCR fragment was cleaved with NdeI and BamHI, and ligated into similarly digested pET-24a(+) (Novagen). An aliquot of the ligation reaction mixture was introduced into *Escherichia coli* BL21 (DE3) (Novagen) and transformants were selected on LB media plus kanamycin (50 μg/mL). Colonies harboring the construct were identified by PCR reactions, using Primers 9 and constructs pET24a/SA-GT, pET28a/GT 3, pET28a/GT 4, pET28a/GT 5, and pET24a/Grape GT were introduced into *Escherichia coli* BL21 (DE3) (Novagen). For protein production, the resulting recombinant strains were grown at 22° C. in 50 mL of LB media that contained kanamycin (50 μg/mL). At an $A_{600\ nm}$ of ~0.6, isopropyl-1-thio-β-D-galactopyranoside was added to a final concentration of 0.2 mM. Following a 22-h induction period at the same temperature, the cells were harvested by centrifugation and stored at −80° C. for subsequent manipulation as described below.

The frozen cell pellets were resuspended in 1.0 mL of a solution containing 100 mM Tris-HCl (pH 7.7), 5 mM $MgSO_4$, 1 mM dithiothreitol, 0.03 mg/mL DNAse I, 0.5 mM phenylmethanesulfonyl fluoride, and passed once through a French pressure cell at 20,000 psi. Debris was removed by centrifugation (43,000×g, 60 min), and the resulting cell-free extracts, containing ~15 mg of protein per mL, were supplemented with 5% glycerol and stored at −80° C. for subsequent measurements of enzyme activities. Protein concentrations were determined by the Bradford Method using bovine serum albumin as a standard.

Two continuous spectrophotometric assays were developed to assess the catalytic activities of the recombinant proteins with pHBA and sinapic acid as substrates. The first assay is based on the increase in absorbance at 304 nm that accompanies the formation of the pHBA glucose ester. Initial rates of product formation were measured at 25° C. in a quartz cuvette (0.5 mL final reaction volume) that contained 50 mM Tris-HCl (pH 7.3), 300 mM NaCl, 5 mM $MgCl_2$, 10 mM UDP-glucose, indicated concentrations of pHBA (1, 5, and 10 mM), and various amounts of the above cell-free extracts; reactions were initiated with the latter. The amount of product formed during the enzyme reactions was calculated from the change in absorbance at 304 nm, using an extinction coefficient of 6,750 $M^{-1}$ for the pHBA glucose ester. The extinction coefficient was determined under the same conditions using a wide range of concentrations of the purified chemically synthesized compound; the absorbance of light followed Beer's Law and was directly proportional to the concentration of the pHBA glucose ester.

The second assay is based on the increase in absorbance at 368 nm that accompanies the formation of the glucose ester of sinapic acid. The experimental conditions were the same as those described above, but the test substrate was sinapic acid and product formation was calculated using an extinction coefficient of 5,570 $M^{-1}$ that was obtained with the authentic chemically synthesized compound under identical conditions. Alternatively, and yielding the same quantitative answer, absorbance was monitored at 350 nm, and the amount of product formed was calculated using an extinction coefficient of 12,000 $M^{-1}$; the latter value was also determined empirically using the same conditions.

Exploiting the two spectrophotometric assays, the five cell-free extracts described above were assayed for UDP-glucosyltransferase activity with pHBA and sinapic acid as substrates (Table 2). The values shown are initial rates of product formation (µM per min) at three different concentrations of pHBA and sinapic acid (1, 5, and 10 mM). Also shown in Table 2 are the ratios of enzyme activity with pHBA versus sinapic acid for all five proteins at the three different substrate concentrations.

The most meaningful information from this analysis is the ratio of activity with the two substrates, not the absolute rates, since the latter depends on the enzyme concentration in the cell-free extracts, which in turn depends on the level of protein expression. Nevertheless, even if the various cell-free extracts did contain different amounts of recombinant protein, it would not have altered the relative activity with the two substrates.

hydroxycinnamic acid derivative was at least 80 times faster than it was with pHBA, when both compounds were assayed at a 10 mM final concentration. At the other extreme, GT 3 was only about twice as active with sinapic acid compared to pHBA under the same conditions.

In summary, despite the fact that all three arabidopsis proteins are 66–67% identical to the *Brassica napus* SA-GT, they exhibit radically different patterns of activity with the two substrates. Moreover, none of these enzymes was more active with pHBA than sinapic acid at any of the substrate concentrations that were tested. In contrast, the Grape GT, which is more distantly related to the *Brassica* SA-GT protein (i.e., only 56% identical), glucosylated pHBA at a rate that was nearly 40 times faster than the analogous reaction with sinapic acid. Based on these observations and Applicants' goal to identify the best catalyst for pHBA, the Grape GT was selected for further characterization and purified to homogeneity as described below.

Example 5

Large-Scale Expression and Purification of the Grape GT

To generate sufficient amounts of the Grape GT for protein purification and enzyme characterization, a 250-mL "seed" culture of the recombinant strain described in Example 3 was grown at 37° C. in LB media that contained kanamycin (50 µg/mL). When the cells had reached an $A_{600\ nm}$ of ~3.0, the entire culture was used to inoculate a 10-liter fermenter. The latter contained the same growth medium described above, but the temperature was maintained at 21.5° C. to minimize the formation of inclusion bodies. At an $A_{600nm}$ of ~0.6, isopropyl-1-thio-β-D-galactopyranoside was added to a final concentration of 0.33 mM. Following an additional 24-h induction period, the cells were harvested by centrifugation and stored at −80° C. for subsequent use. The entire cell pellet (63 g wet weight) was resuspended in 95 mL ice-cold 100 mM Tris-HCl (pH 7.5), 5 mM $MgSO_4$, 1 mM dithiothreitol, 0.03 mg/mL DNAse I, 0.5 mM phenylmethanesulfonyl fluoride, and passed twice through a French pressure cell at 20,000 psi. Unless otherwise noted, subsequent steps were at 0–4° C. Cell debris was removed by centrifugation (43,000×g, 90 min), and the resulting cell-free extract, containing ~50 mg of protein per

TABLE 2

| Crude Extract | 1 mM SA | 1 mM pHBA | pHBA/SA | 5 mM SA | 5 mM pHBA | pHBA/SA | 10 mM SA | 10 mM pHBA | pHBA/SA |
|---|---|---|---|---|---|---|---|---|---|
| SA-GT | 118 | 0.20 | 0.002 | 82 | 0.59 | 0.007 | 55.6 | 1.03 | 0.018 |
| GT 3 | 146 | 9.4 | 0.064 | 158 | 42.3 | 0.268 | 143 | 64.9 | 0.454 |
| GT 5 | 5.18 | 0.23 | 0.044 | 9.2 | 0.45 | 0.049 | 5.9 | 0.83 | 0.141 |
| GT 4 | 37.6 | 0.20 | 0.005 | 63 | 0.45 | 0.007 | 59.1 | 0.70 | 0.012 |
| Grape GT | 22.8 | 96.4 | 4.23 | 16.6 | 177 | 10.7 | 4.8 | 181 | 37.7 |

Focusing on the results with 10 mM substrate, it is apparent that the *Brassica napus* SA-GT is at least 50 times more active with sinapic acid than pHBA, and the preference for this compound is even more pronounced at the lower substrate concentrations. A similar trend was observed with the three arabidopsis homologs, but there was tremendous variation amongst the different proteins. Like the *Brassica* SA-GT protein, GT 4 strongly preferred sinapic acid as a substrate, and the initial rate of product formation with this mL, was supplemented with glycerol (5%) and stored at −80° C. for subsequent purification.

The first step in purifying the Grape GT was employing anion exchange chromatography. A 10-mL aliquot of the cell-free extract was rapidly thawed and filtered through a 0.2 µm Acrodisc filter (Gelman-Pall Life Sciences, Ann Arbor, Mich. Cat. No. 4192). The entire sample was then applied to a Mono Q HR 16/10 column (Amersham Biosciences, Piscataway, N.J.) that was pre-equilibrated at 25°

C. with Buffer Q (50 mM Tris-HCl, pH 7.7, 10 mM sodium sulfite, 1 mM EDTA). The column was developed at 4 mL/min with Buffer Q for the first 17.5 min, and this was followed by a linear gradient (80 mL) of 0–133 mM NaCl (in Buffer Q); 10-mL fractions were collected from the start of the gradient. Aliquots (10 µL) of each column fraction were tested for UDP-glucosyltranferase activity using sinapic acid as a substrate. The basis of this assay is the appearance of yellow color when glucose is attached to the carboxyl group of sinapic acid. This lowers the pKa of the aromatic hydroxyl group, which results in the formation of the phenolate ion which is bright yellow and easy to monitor visually. The 50-µL reactions, which were performed at room temperature, contained 24 mM Tris-HCl (pH 7.5), 140 mM NaCl, 4.2 mM $MgCl_2$, 8 mM dithiothreitol, 16 mM UDP-glucose, and 8 mM sinapic acid. Based on the visual assay, virtually all of the recombinant protein was detected in Fraction 7. At the end of the gradient, the column was extensively washed with 1 M NaCl (in Buffer Q) and the initial conditions were reestablished. The active fraction was supplemented with 8.6 mM dithiothreitol and 6.5% glycerol, and kept on ice while five more 10-mL aliquots of the cell-free extract were processed in an identical manner. The active fractions from all six runs were combined and stored at −80° C. for subsequent processing.

In the next step, the pooled fractions (70 mL total volume) were subjected to ammonium sulfate precipitation, after adding 8 mL of 1 M potassium phosphate (pH 6.34). While the solution was gently stirred at 4° C., solid $(NH_4)_2SO_4$ was slowly added to 20% saturation, and after a 30-min incubation period the sample was centrifuged at 10,000×g for 30 min. The supernatant was retained and solid $(NH_4)_2SO_4$ was supplemented to 40% saturation under the conditions described above. Following centrifugation, the supernatant was again retained and solid $(NH_4)_2SO_4$ was added to 60% saturation. After a 20-min incubation period at 4° C., the mixture was centrifuged as described above, and the supernatant was discarded. The pellet, which contained most of the recombinant protein, as determined by SDS-PAGE and Coomassie blue-staining, was dissolved in 6 mL of a solution containing 50 mM Tris-HCl (pH 7.2), 2 mM EDTA, 5 mM dithiothreitol, and 7.5% glycerol. The entire sample was then filtered through a 0.2 µm Acrodisc filter (Gelman-Pall Life Sciences: Cat. No. 4192), and fractionated on a TSK-Gel® G3000SW gel filtration column (21×600 mM) (Tosoh Biosep LLC., Montgomeryville, Pa.) in 2-mL aliquots. The column was developed at 4 mL/min with 50 mM Tris-HCl (pH 7.2), 300 mM NaCl, 1 mM dithiothreitol, 0.5 mM EDTA (25° C.). The material eluting between 34.66 and 36.33 min (corresponding to the peak of UDP-glucosyltransferase activity with sinapic acid as substrate) was collected and supplemented with 6.5% glycerol and additional dithiothreitol (4.3. mM). This procedure was repeated two more times, consuming the entire sample, and the active fractions from all three gel filtration columns were combined for further processing.

Figure 2:
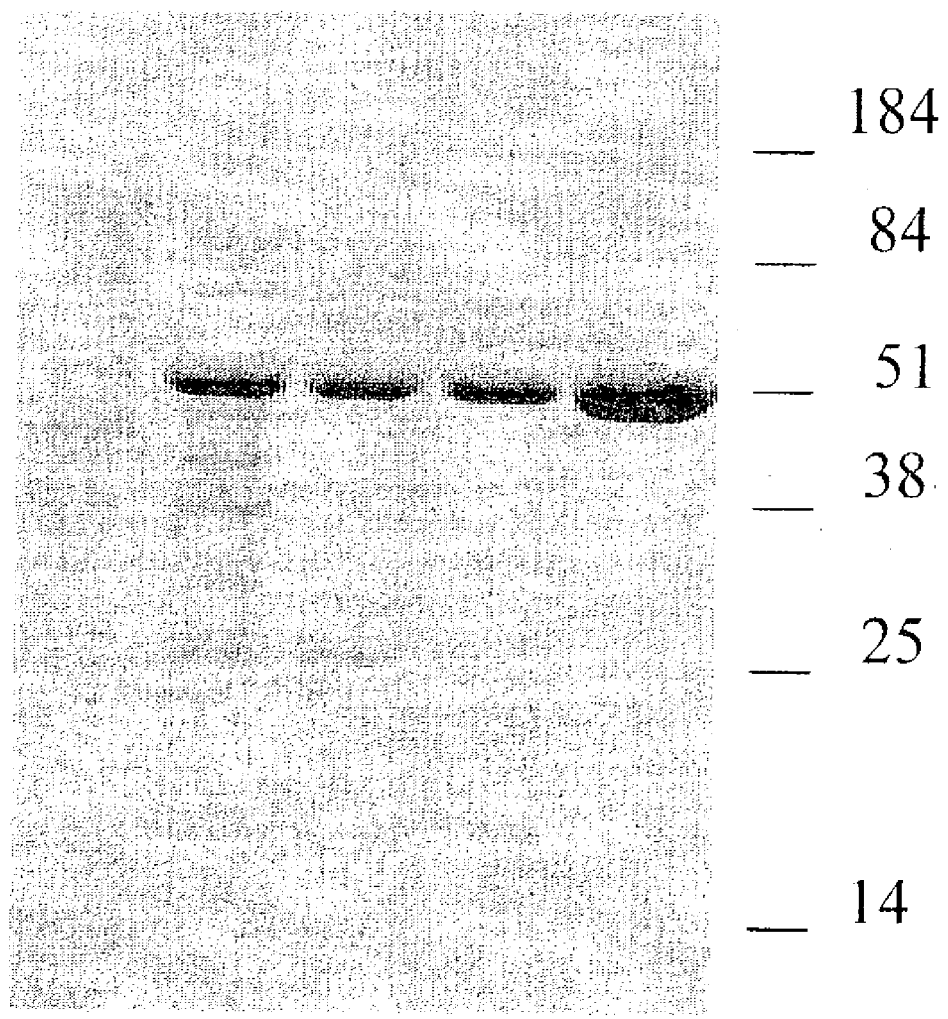
FIG. 2 is a Coomassie blue-stained 14% SDS-PAGE gel of the purified recombinant Grape GT protein that was used for enzyme characterization (lane 5). The other lanes show the recombinant Grape GT at various stages of the large-scale purification procedure that is described in Example 5.

The material described above was concentrated to 2 mL in a Centripep-30 (Millipore Corp., Bedford, Mass.) and diluted with 18 mL of 10 mM sodium phosphate (pH 6.8), 0.01 mM $CaCl_2$. Half the sample (10 mL) was then injected onto a 100×7.8 mM Bio-Gel HPHT hydroxylapatite column (Bio-Rad, Hercules, Calif.), pre-equilibrated with 10 mM sodium phosphate (pH 6.8), 0.01 mM $CaCl_2$. The column was developed at 1 mL/min (25° C.) with a linear gradient (25 mL) of 10–350 mM sodium phosphate, pH 6.8 (containing 0.01 mM $CaCl_2$). Fractions eluting between ~127 and 158 mM sodium phosphate were pooled, supplemented with 5.8% glycerol and 7.7 mM dithiothreitol, and kept on ice while the remaining half of the sample was processed in an identical manner. The pooled fractions from both runs were combined, concentrated to a final volume of 0.75 mL in a Centricon-10 (Millipore Corp.) and stored at −80° C. The concentration of the purified recombinant protein described above was 6.7 mg/mL. An extinction coefficient at 280 nm of 66, 360 $M^{-1}$ (as calculated by the Peptidesort program of GCG) was used to determine protein concentration. Visual inspection of overloaded Coomassie-stained gels indicated that the purified recombinant grape glucosyltransferase was at least 95% pure (FIG. 2, lane 5).

For all the enzyme assays described below, frozen aliquots of the purified Grape GT were rapidly thawed and diluted to the desired concentration with ice-cold buffer containing 50 mM Tris-HCl (pH 7.6), 1 mM EDTA, 10 mM $Na_2SO_3$, 300 mM NaCl, 6% glycerol and 5 mM dithiothreitol. When diluted in this manner, kept on ice, and rapidly frozen to −80° C. after use, the purified recombinant protein was stable to multiple cycles of freeze/thaw without significant loss of enzyme activity.

Example 6

HPLC Verification that Grape GT Only Attaches Glucose to the Carboxyl Group of pHBA Of the five proteins tested for glucosyltransferase activity in Example 4, only the Grape GT was able to glucosylate pHBA at a faster rate than sinapic acid. To confirm, this important observation and characterize the enzyme in more rigorous detail, the recombinant protein was purified to homogeneity as described in Example 5.

Although the spectrophotometric assay described above for pHBA faithfully monitors formation of the glucose ester, it would not reveal the presence of other glucosylated species. For example, if the Grape GT were also able to attach glucose to the hydroxyl group of pHBA, this reaction would go undetected using the spectrophotometric assay. Indeed, there are several examples in the literature of plant UDP-glucosyltransferases that are capable of attaching glucose to either the carboxyl or hydroxyl groups of aromatic compounds that possess both functionalities (Fraissinet-Tache et al., *FEBS Letts* 437, 319–323 (1998); Lee, H. and Raskin, I., *J. Biol. Chem.* 247, 36637–36642 (1999)). These include pHBA, the compound of interest to Applicants.

To rule out the possibility that the Grape GT can also attach glucose to the hydroxyl group of pHBA, the products of the in vitro enzyme reaction were directly analyzed by reverse phase HPLC. The experimental conditions were similar to those used for the spectrophotometric assay, but the reaction mixture contained 50 mM Tris-HCl (pH 7 3), 300 mM NaCl, 5 mM $MgCl_2$, 5 mM UDP-glucose, 0.3 mM pHBA and 0.934 µM of the purified recombinant Grape GT; the reaction was initiated with the latter. Following a 1-min incubation period at 25° C., the reactions were terminated by the addition of an equal volume of 0.2 N HCl. The samples were briefly centrifuged, and 20-µL aliquots of the resulting supernatants were injected onto a Vydac 218TP54 Protein and Peptide C18 column, (Grace Vydac, Hesperia, Calif.) pre-equilibrated with 90% Buffer A (0.1% formic acid in water) and 10% Buffer B (methanol). The column was developed at 1 mL/min with a linear gradient of 10–50% Buffer B that was generated over a 20-min period, and absorbance was monitored at 254 nm. Based on the retention times of authentic chemical standards, the only glucosylated product that was detected in the fractionated enzyme reaction mixture was the pHBA glucose ester, which eluted at 6.13 min. Under these conditions, the pHBA phenolic glucoside (e.g., pHBA with glucose attached to the aromatic hydroxyl group) should have eluted at 4.75 min. However, a peak with this retention time was not observed in the HPLC chromatograms, indicating that the Grape GT is not able to form the pHBA phenolic glucoside under these conditions.

As noted above, there are examples in the literature of purified plant UDP-glucosyltransferases that are able to attach glucose to both the carboxyl and hydroxyl group of pHBA. Indeed, Applicants have confirmed these results for the two salicylate-inducible UDP-glucosyltransferases from tobacco that were initially characterized by Fraissinet-Tachet et al., supra.

Moreover, in unpublished experiments with the same proteins, Applicants have discovered that it is possible to alter the partitioning of the two pHBA glucose conjugates simply by varying the pH of the enzyme reaction; the phenolic glucoside is the predominant product at pH values greater than 6.5. In light of these observations, it was extremely important to analyze the reaction products of the Grape GT over a broader range of pH that encompasses physiological conditions. These experiments were carried out at 25° C. using two different concentrations of pHBA, either 0.15 mM or 5 mM. In addition, the reaction mixtures also contained 100 mM potassium phosphate buffer (pH 6.0, 7.0 or 8.0), 5 mM MgCl$_2$, 5 mM UDP-glucose, 2 mM dithiothreitol, and 0.47 µM of the purified recombinant Grape GT. After a 15-min incubation period, the reactions were terminated by the addition of an equal volume of 0.3 M HCl and analyzed by reverse phase HPLC as described above. Regardless of the initial substrate concentration or pH of the enzyme reaction, the only glucose conjugate that was detected in the in vitro assay was the pHBA glucose ester.

Example 7

Kinetic Characterization and Substrate Specificity of the Purified Recombinant Grape GT The fact that the Grape GT was uniquely able to glucosylate pHBA at a faster rate than sinapic acid (see Example 5) suggested that the preferred substrates for this enzyme might be hydroxybenzoic acid derivatives, like pHBA, not hydroxycinnamic acid derivatives, like sinapic acid. To test this hypothesis, Applicants' decided to examine the substrate specificity of the Grape GT in greater detail. The basic reaction mixture for these experiments contained 50 mM Tris-HCl (pH 7.3), 300 mM NaCl, 5 mM MgCl$_2$, 10 mM UDP-glucose, 0.0467 µM of the purified Grape GT and a 10 mM final concentration of the test substrate. Following a 15-min incubation period at 25° C., the reactions were quenched with an equal volume of 0.3 M HCl and the entire reaction mixture was analyzed by HPLC as described above in Example 6. The products of the various reactions were identified using authentic chemical standards. The retention times and extinction coefficients of these compounds were determined using the same column conditions. The ester glucoside standards for pHBA, pHCA, caffeic acid, ferrulic acid, and sinapic acid were synthesized and characterized by Applicants. The ester glucoside standards for oHBA, mHBA, and gallic acid were synthesized enzymatically, purified by reverse phase HPLC, and quantitated by calculating the amount of substrate that was converted to product. Regardless of substrate, the purified recombinant Grape GT only catalyzed the formation of glucose esters, which in all cases co-migrated precisely with the authentic compounds.

Table 3 summarizes the results obtained with eight different test substrates: four hydroxybenzoic acid derivatives and four hydroxycinnamic acid derivatives. The rate of product formation for each substrate is expressed relative to pHBA, which was arbitrarily given a value of 100. Based on the results of this survey, it is clear that pHBA (4-hydroxybenzoic acid) is the best substrate for the Grape GT, followed by gallic acid (3, 4, 5-trihydoxybenzoic acid). Since the glucose ester of the latter compound is the precursor for the synthesis of simple and complex tannins that are extremely abundant in grapes, it is possible that gallic acid is a physiological substrate of the Grape GT. The data shown in Table 3 make it clear that although the Grape GT glucosylated mHBA (3-hydroxybenzoic activity) at a reasonable rate, product formation with oHBA (2-hydroxybenzoic acid) was not observed. Furthermore, pHCA (4-hydroxycinnamic acid) was nearly as good a substrate as gallic acid and better than mHBA. The other three hydroxycinnamic acid derivatives that were tested (caffeic acid, ferrulic acid, and sinapic acid) were all glucosylated at a much slower rate than pHBA.

TABLE 3

| Test Substrate | Relative Rate |
| --- | --- |
| Hydroxybenzoic acids | |
| PHBA | 100 |
| MHBA | 47 |
| OHBA | 0 |
| Gallic acid | 64 |
| Hydroxycinnamic acids | |
| PHCA | 56 |
| Caffeic acid | 25 |
| Ferrulic acid | 16 |
| Sinapic acid | 10 |

A kinetic analysis of the Grape GT with pHBA as a substrate is shown in FIG. 1. Initial rates of product formation were measured at 25° C. over a wide range of substrate concentrations using the spectrophotometric assay (see Example 4). The reactions mixture contained 50 mM Tris-HCl (pH 7.3), 300 mM NaCl, 5 mM MgCl$_2$, 10 mM UDP-glucose, indicated concentrations of pHBA and 0.0374 µM purified recombinant Grape GT, which was used to initiate the reaction. The formation of the pHBA ester glucoside was monitored at 304 nm, and the data was fitted to the Michaelis-Menten equation. Under these conditions, the apparent $K_m$ and $V_{max}$ values were 0.70 mM and 24.4 µM/min, respectively. Taking into account the amount of enzyme that was present in the assay, the latter value translates to a turnover number ($k_{cat}$) of ~10.9 sec$^{-1}$ when the enzyme is saturated with pHBA. However, this value is not entirely accurate. Visual inspection of the V versus S curve shown in FIG. 1 suggests that the enzyme is subject to mild substrate inhibition at high concentrations of pHBA. A kinetic fit of the data shows that the calculated $K_i$ for substrate inhibition is ~32.5 mM. The substrate inhibition of the Grape GT is a much bigger problem with sinapic acid than with pHBA (i.e., compare initial velocities of the Grape GT at 1, 5, and 10 mM sinapic acid (Table 2)).

Lim et al. (J. Biol. Chem. 276, 9:4344–4349 (2001)) describes a detailed kinetic analysis of three closely related arabidopsis glucosyltransferases (UGT84A1, UGT84A2, and UGT84A3) that only form ester glucosides. Five different cinnamic acid derivatives were evaluated as substrates (i.e., cinnamic acid, p-hydroxycinnamic acid, caffeic acid, ferrulic acid, and sinapic acid), and the $V_{max}$ values for the best substrate for each of the proteins was determined. Since the molecular masses of these proteins are known, it is easy to calculate turnover numbers for comparative purposes. The preferred substrate for UGT84A1 (referred to as GT 3 in the instant invention) was p-hydroxycinnamic acid and the turnover number for this compound was ~0.70 sec$^{-1}$. The best substrate for UGT84A2, which was not evaluated in the instant invention, was sinapic acid and the turnover number for this substrate was ~0.72 sec$^{-1}$. Finally, the preferred substrate for UGT84A3 (referred to as GT 4 in the instant invention) was cinnamic acid and the turnover number for this substrate was ~0.9 sec$^{-1}$. Although these values were determined at a slightly lower temperature (20° C. versus 25° C.), under slightly different conditions (i.e., pH 6, which the authors indicated was optimal for ester glucoside formation for the three arabidopsis proteins), they are clearly much lower than the turnover number for the Grape GT with pHBA as a substrate.

In a subsequent study Lim and colleagues (*J. Biol. Chem.* 277: 586–592 (2002)) reported the results of a massive screening effort to identify arabidopsis UDP-glucosyltransferases that are active with benzoic acid derivatives. Remarkably, of the ninety different proteins tested, only three were able to attach glucose to the carboxyl group of pHBA with significant catalytic activity. One of these proteins, referred to as 84A1, is identical to GT 3. The turnover number of this enzyme with pHBA as a substrate was ~0.21 sec$^{-1}$ at 20° C. (Lim et al., *J. Biol. Chem.* 277: 586–592 (2002)), which is considerably lower than its turnover number with p-hydroxycinnamic acid under similar conditions (Lim et al., *J. Biol. Chem.* 276, 9:4344–4349 (2001)). Interestingly, the best arabidopsis UDP-glucosyltransferase for formation of the pHBA ester glucoside, a protein referred to as 75B1, only had a turnover number of 0.73 sec$^{-1}$ at 20° C. (Lim et al., *J. Biol. Chem.* 277: 586–592 (2002)).

Taken together, the above observations provide compelling evidence that the Grape GT is an excellent catalyst for synthesis of the pHBA ester glucoside.

Example 8

The Grape GT can be used to Identify Other Plant Glucosvitransferases from Diverse Plant Species that Catalyze the Formation of the pHBA Glucose Ester with High Efficacy It is true that the primary amino acid sequence of the *Brassica napus* SA-GT is a useful query sequence for identifying other plant UDP-glucosyltransferases that attach glucose to the carboxyl group of aromatic compounds. However, the primary amino acid sequence is not a reliable predictor of kinetic properties or substrate specificity, especially with regard to hydroxybenzoic acids. Indeed, of the five proteins tested in Table 2, only the Grape GT catalyzed the formation of the pHBA glucose ester with a high turnover number. Importantly, this conclusion could not have been arrived at from the amino acid sequence information alone, since the Grape GT was the most distantly related homolog to the original query sequence, the *Brassica napus* SA-GT (Table 1). According to the phylogenetic nomenclature originally developed by Mackenzie et al. (*Pharmacogenetics* 7:255–269 (1997)) and subsequently expanded on by Lim and co-workers (*J. Biol. Chem.* 276: 4344–4349 (2001)), the *Brassica napus* SA-GT and the three arabidopsis proteins (GT 3, GT 4, and GT 5) belong to the same subfamily of UDP-glucosyltransferases. These proteins are all at least 60% identical at the amino acid sequence level. In contrast, the Grape GT is only 56–58% identical to any of these proteins (Table 4) and hence belongs to a different subfamily of UDP-glucosyltransferases, which was not described previously. Given these observations, it was of interest to see if the Grape GT could be used as a probe to identify other members of the same subfamily, ones that only form glucose esters and preferentially glucosylate pHBA with high catalytic activity.

Towards this goal, the primary amino acid sequence of the Grape GT (SEQ ID NO:18) was used as a query sequence to search Applicants' EST database for the most closely related homolog. The tBlastn algorithm (Altschul et al., *Nucleic Acids Res.* 25:3389–3403 (1997)) with the standard default settings was employed for this search. The results of the tBlastn search identified a putative full-length cDNA clone (eea1c.pk002.016) that was 66% identical to the first 66 N-terminal amino acid residues of the Grape GT; only partial sequence information for this clone was available at the time, corresponding to the 5' end of the messenger RNA. The cDNA library that gave rise to eea1c.pk002.016 was generated from apical leaves of a *Eucalyptus grandis* plant using standard techniques. The cDNA insert in eea1c.pk002.016 was sequenced completely. The nucleotide sequence of the ORF of this protein, henceforth referred to as the "Eucalyptus GT", and its predicted primary amino acid sequence are set forth in SEQ ID NO:21 and SEQ ID NO:22, respectively. The GAP algorithm with the standard default settings was used to align the full-length primary amino acid sequences of the grape and eucalyptus UDP-glucosyltransferases. Overall, the two proteins are 82.2% identical and are therefore, by definition, members of the same subfamily.

The primary amino acid sequence of the Grape GT (SEQ ID NO:18) was also used as a query sequence to search the GenBank® database for the protein with the highest degree of homology. The tBlastn algorithm (Altschul et al., *Nucleic Acids Res.* 25:3389–3403 (1997)) with the standard default settings was employed for this search. This resulted in the identification of a cDNA clone (GenBank® Accession number AB033758.1) from *Citrus unshiu* (Kita et al., *Febs Letters* 469:173–178 (2000)) that encodes a protein that is 75.1% identical to the Grape GT at the primary amino acid sequence level. Therefore, by definition, the *Citris unshiu* enzyme is also a member of the same subfamily of glucosyltransferase proteins that includes the Grape and Eucalyptus GTs.

Expression Cloning and Biochemical Characterization of the *Eucalyptus* GT

The flanking regions of the ORF of the Eucalyptus GT were modified by PCR for insertion into the high-level *Escherichia coli* expression vector, pET29a(+) (Novagen). This insertion was accomplished using Primers 11 and 12 and purified plasmid DNA from the original cDNA clone as the target for amplification.

```
Primer 11-
                                          (SEQ ID NO:23)
5'-CTC GAG GTC GGT GAC cat atg GGG TCG G-3'

Primer 12-
                                          (SEQ ID NO:24)
5'-CTC ATC aag ctt TCA CGA CAC CAC C-3'
```

The underlined bases hybridize to the target gene, while lower case letters indicate the restriction sites (NdeI or HindIII) that were added to the ends of the PCR primers. Primer 11 hybridizes at the start of the gene and introduces an NdeI site at the initiation codon, while Primer 12 hybridizes at the opposite end and provides a HindIII site just after the stop codon, neither primer alters the amino acid sequence of the ORF of the Eucalyptus GT. The PCR reaction contained 50 mM KCl, 10 mM Tris-HCl (pH 9), 0.1% Triton X-100, 2.5 mM $MgCl_2$, 0.2 mM each dNTP, 5 units of Taq polymerase (MBI Fermentas, USA), 10 ng of the cDNA plasmid template, and both PCR primers at a final concentration of 0.2 μM. Amplification was carried out for 25 cycles, each comprising 1.5 min at 94° C., 1.5 min at 55° C., and 2.5 min at 72° C. The PCR product was digested with NdeI and HindIII, gel-purified, and the resulting fragment was ligated into the *Escherichia coli* expression vector, pET-29a(+) (Novagen) that was digested with the same restriction enzymes. The ligation reaction mixture was used to transform *Escherichia coli* DH10B, and plasmid DNA from a representative colony was sequenced completely to check for PCR errors; none were found. The plasmid selected for further manipulation is referred to below as "pET29a/Eucalyptus GT".

For protein expression, pET29a/Eucalyptus GT was introduced into *Escherichia coli* BL21 (DE2) (Novagen), and the resulting recombinant strain was grown at 22° C. in 100 mL of LB media that contained kanamycin (50 μg/mL). At an $A_{600nm}$ of ~0.6, isopropyl-1-thio-β-D-galactopyranoside was added to a final concentration of 0.2 mM. Following an additional 24-h induction period at the same temperature, the cells were harvested by centrifugation. The pellet was resuspended in 2.5 mL of a solution containing 50 mM Tris-HCl (pH 7.5), 300 mM NaCl, 1 mM dithiothreitol, and passed twice through a French pressure cell at 20,000 psi. Debris was removed by centrifugation (14,000×g, 30 min), and the cell-free extract, containing ~7 mg of protein per mL, was supplemented with 5% glycerol and stored at −80° C. for subsequent measurements of enzyme activity with pHBA and sinapic acid as substrates.

Initial rates of product formation were measured spectrophotometrically at 25° C. in a quartz cuvette (final reaction volume 0.5 mL) that contained 50 mM Tris-HCl (pH 7.3), 300 mM NaCl, 5 mM $MgCl_2$, 10 mM UDP-glucose, and a 10 mM final concentration of pHBA or sinapic acid; 50 μL of the cell-free extract described above was used to initiate the reaction. These are the exact same conditions that were used to determine the substrate specificity (pHBA versus sinapic acid) of the other plant UDP-glucosyltransferases that were characterized in Example 4 (Table 2). As shown in Table 4, similar to the Grape GT, the Eucalyptus GT protein exhibited a strong preference for pHBA as a substrate. Indeed, the rate of product formation with this compound was over an order of magnitude greater than that obtained with sinapic acid.

TABLE 4

| Glucosyltransferase | % Identity to Grape GT (pairwise GAP alignment) | Ratio of Activity pHBA/SA |
|---|---|---|
| Grape GT | 100 | 37.7 |
| Eucalyptus GT | 82 | 13.2 |
| Citrus GT | 75.5% | 6.35 |
| Arabidopsis GT 3 | 58 | 0.454 |
| Arabidopsis GT 5 | 57 | 0.141 |
| Brassica SA-GT | 56 | 0.018 |
| Arabidopsis GT 4 | 56 | 0.012 |

Further investigation revealed that most of the recombinant Eucalyptus GT protein expressed in *E. coli* was insoluble material and present in the form of inclusion bodies. Consequently, it would have been very difficult to purify sufficient amounts of the soluble native protein for characterization of enzyme activity. Applicants therefore decided to generate a new Eucalyptus GT expression construct that encodes a fusion protein with a C-terminal hexa-histidine tag to facilitate protein purification. To this end the flanking regions of the ORF of the Eucalyptus GT were modified by PCR for insertion into the high-level *E. coli* expression vector, pET29a(+) (Novagen). This was accomplished using Primers 11 and 13 and purified plasmid DNA from the original cDNA clone as the target for amplification.

Primer 13-
(SEQ ID NO:25)
5'-<u>TCC ACC</u> aag ctt <u>CGA CAC CAC CTT TAA CTC C</u>-3'

The underlined bases hybridize to the target gene, while lower case letters indicate the restriction sites (NdeI or HindIII) that were added to the ends of the PCR primers. Primer 11 hybridizes at the start of the gene and introduces an NdeI site at the initiation codon, while Primer 13 introduces an HindIII site, lacks a stop codon and creates an in-frame fusion to sequences of the pET29A vector encoding a peptide of 13 amino acids comprising a C-terminal hexa-histidine tail. The resulting plasmid contains an open reading frame the forth as SEQ ID NO:26. It is created by the nucleotide sequence of the Eucalyptus GT gene and nucleotide sequence of the pet29A vector. The primary amino acid sequence of the Eucalyptus GT protein variant with the C-terminal hexa-histidine tail is set forth as SEQ ID NO:27. The PCR reaction contained 50 mM KCl, 10 mM Tris-HCl (pH 9), 0.1% Triton X-100, 2.5 mM $MgCl_2$, 0.2 mM each dNTP, 5 units of Taq polymerase (MBI Fermentas), 10 ng of the cDNA plasmid template, and both PCR primers at a final concentration of 0.2 μM. Amplification was carried out for 25 cycles, each comprising 1.5 min at 94° C., 1.5 min at 55° C., and 2.5 min at 72° C. The PCR product was digested with NdeI and HindIII, gel-purified and the resulting fragment was ligated into the *E. coli* expression vector, pET-29a(+) (Novagen) that was digested with the same restriction enzymes. The ligation reaction mixture was used to transform *E. coli* DH10B. Plasmid DNA from a representative colony was sequenced completely to check for PCR errors; none were found. The plasmid selected for further manipulation is referred to below as "pET29a/Eucalyptus GT His Tag".

To generate sufficient amounts of the Eucalyptus GT His Tag protein for enzyme purification and characterization, a 50-mL "seed" culture of recombinant BL21DE3 cells harboring the pET29a/Eucalyptus GT His Tag plasmid were grown at 37° C. in LB media that contained kanamycin (50 μg/mL). The culture was diluted 200 fold into two shaking flasks containing 2.5 L of LB medium supplemented with 50 μg/mL of kanamycin. The cultures were grown at 22° C. until the $OD_{600}$ had reached 0.6. At this point IPTG was added to a final concentration of 0.2 mM. The cells were cultured for 24h, harvested by centrifugation, resuspended in 60 mL of GT extraction buffer (50 mM Tris/HCl pH 7.5, 300 mM NaCl, 5 mM $MgCl_2$, 2 mM DTT) and passed twice through a French pressure cell at 20,000 psi. Unless otherwise noted, subsequent steps were at 0–4° C. Cell debris was removed by centrifugation (43,000×g, 90 min), and the resulting cell-free extract, containing ~60 mg of protein per mL, was supplemented with glycerol (5%) and stored at −80° C. for subsequent purification. The Eucalyptus GT His Tag protein was purified by nickel chelate affinity chromatography as follows. Six 2.5 mL aliquots of the cell-free *E. coli* extract corresponding to 900 mg of total *E. coli* protein were desalted on PD10 columns (Amersham Biosciences) into Buffer A (20 mM sodium phosphate, 500 mM NaCl, 10 mM imidazole, pH 7.5). Three and a half mL of the desalted sample was loaded onto a 5 mL HiTrap chelating HP cartridge (Amersham Biosciences) at a flow rate of 1 mL/min. The cartridge was washed with 20 mL of Buffer A at 1 mL/min followed by 20 mL of 60 mM imidazole in Buffer A at the same flow rate. The loading and washing steps were repeated five more times, and the Eucalyptus GT His Tag protein was then eluted from the column with a gradient in which the imidazole concentration was raised from 60 mM to 500 mM over a 20 min period at a flow rate of 1 mL/min; 1.5 mL fractions were collected. Fractions containing Eucalyptus GT His Tag enzyme activity were identified using the visual assay with sinapic acid and UDP-glucose that was previously described for the Grape GT (Example 5). Aliquots (~6 µl) of appropriate fractions were analyzed by SDS-PAGE, and visual inspection of Coomassie-stained gels identified a fraction in which the recombinant Eucalyptus GT His Tag protein was >90% pure. The column fraction was diluted to 2.5 mL with GT extraction buffer, and the entire sample was buffer exchanged on a PD-10 gel filtration column (Pharmacia, Piscataway, N.J.), pre-equilibrated with GT extraction buffer. The 3.5-mL desalted sample was supplemented with 5% glycerol and concentrated to a final volume of 250 µl using a Centricon-10 (Millipore Corp.). The final concentration of the purified recombinant Eucalyptus GT His Tag protein was 0.488 mg of protein per mL, which corresponds to a monomer concentration of 8.38 µM. Protein concentration was calculated using an extinction coefficient of 76, 400 $M^{-1}$ at 280 nm, as determined by the GCG Peptidesort program using the amino acid composition given in SEQ ID NO:27.

The kinetic properties of the purified Eucalyptus GT His Tag protein with pHBA as a substrate were determined spectrophotometrically essentially as described for the Grape GT (Example 7), but assays were initiated by the addition of 0.0336 µM of the purified enzyme. pHBA ester glucoside formation was monitored at 304 nm, and the data was fit to the Michaelis-Menten equation. Under these conditions, the apparent Km and Vmax values were 1.28 mM and 31.06 µM/min, respectively. The latter value corresponds to a turnover number ($k_{cat}$) for pHBA of ~15.45 $sec^{-1}$, which is even higher than the Grape GT.

Although the purified Eucalyptus GT His Tag protein was not tested with the entire array of hydroxybenzoic and hydroxycinnamic acids that were used in Table 3, initial rates of product formation with pHBA and sinapic acid were measured spectrophotometrically at 25° C., to determine the relative substrate specificity. The 0.5-mL reactions contained 50 mM Tris-HCl (pH 7.3), 300 mM NaCl, 5 mM $MgCl_2$, 10 mM UDP-glucose, and a 10 mM final concentration of pHBA or sinapic acid; the reactions were initiated with 10 µL of the purified enzyme. These are the exact same conditions that were used to determine the substrate specificity (pHBA versus sinapic acid) of the crude extracts that were characterized in Table 2. The results reveal that the purified Eucalyptus GT His Tag protein has essentially the same relative substrate specificity for pHBA versus sinapic acid (14.1) as the unmodified protein that was used in Table 4 (13.2), suggesting that C-terminal modification does not significantly alter enzyme activity.

Additionally, HPLC analysis (as described in Example 6) confirmed that the purified Eucalyptus GT His Tag protein only attaches glucose to the carboxyl group of pHBA; no pHBA phenolic glucoside was detected in the chromatograms. Taken together, the above observations provide compelling evidence that the Eucalyptus GT, with or without a His tag, is an excellent catalyst for synthesis of the pHBA ester glucoside, like the Grape GT.

Cloning, Expression and Biochemical Characterization of the *Citrus mitis* GT

As already indicated, of all the proteins that are available in the public domain, the one that shows the greatest homology to the Grape GT is a UDP-glucosyltransferase from *Citrus unshiu* (GenBank Accession No. AB033758.1). However, since Applicants were not able to gain access to this particular plant a closely related species was used. Thus, a calamondin plant (*Citrus mitis*) that is commonly used for ornamental purposes was purchased from a local nursery (Old Country Gardens, Wilmington, Del., USA), and genomic DNA was isolated from its leaf tissue using standard techniques. Two primers were designed according to the published sequence of *Citrus Unshiu* GT for PCR-amplification of the corresponding protein from *Citrus mitis*.

```
Primer 14-
CATTCGAGAcatatgGGAACTGAATCTC    (SEQ ID NO:28)

Primer 15-
GTCAGAACTTCgtcgacATACTGTAC      (SEQ ID NO:29)
```

The underlined bases hybridize to the target gene, while lower case letters indicate the restriction sites (NdeI or SalI) that were added to the PCR primers. Primer 14 hybridizes at the start of the gene and introduces an NdeI site at the initiation codon, while Primer 15 hybridizes at the opposite end and introduces a SalI site just downstream from the naturally occurring stop codon. However, primer 15 lacks the naturally occurring stop codon of the published *Citrus unshiu* sequence, and thereby facilitates an in-frame fusion to sequences of the pET29A vector that encode a peptide of 15 amino acid residues, which comprises a C-terminal hexa-histidine tail.

The PCR cloning strategy described above assumed that there were no significant differences in the nucleotide sequences of the genes that code for the *Citrus unshiu* and *Citrus mitis* UDP-glucosyltransferases, specifically at the 5' and 3' ends of the ORF. However, as described below, this turned out not to be the case. The PCR reaction contained 50 mM KCl, 10 mM Tris-HCl (pH 9), 0.1% Triton X-100, 2.5 mM $MgCl_2$, 0.2 mM each dNTP, 5 units of Taq polymerase (MBI Fermentas, USA), 500 ng of genomic *Citrus mitis* DNA template and both PCR primers at a final concentration of 0.2 µM. Amplification was carried out for 35 cycles, each comprising 45 sec at 94° C., 45 sec at 52° C., and 1.5 min at 72° C. PCR products of approximately 1.5 kb were gel-purified, cloned into the pCR2.1 vector (Invitrogen, USA) using the TOPO T/A cloning kit (Invitrogen, USA) according to manufacturer's instructions. The complete nucleotide sequence of the PCR product was determined using standard methods. The nucleotide sequence of the ORF of this protein (henceforth referred to as the "*Citrus mitis* GT") and its predicted primary amino acid sequence are set forth in SEQ ID NO:30 and SEQ ID NO:31, respectively. The GAP algorithm with the standard default settings was used to align the full-length primary amino acid sequences of the grape and *Citrus mitis* UDP-glucosyltransferases. Overall, the two proteins are 75.5% identical and are therefore, by definition, members of the same subfamily.

The *Citrus mitis* GT gene described in the present invention is 98.7% identical to the *Citrus unshiu* GT cDNA at the nucleotide level. However, the nucleotide sequences of the two citrus proteins differ in a way that profoundly effected the original cloning strategy to generate a His-tagged *Citrus mitis* GT fusion protein. Specifically, close to the 3' end of the *Citrus unshiu* ORF there is a CGA that codes for an arginine residue, and this sequence is replaced by a stop codon (TGA) in the *Citrus mitis* gene. Due to the presence of the unexpected premature stop codon, the *Citrus mitis* protein lacks seven C-terminal amino acid residues that are present in the published *Citrus unshiu* protein. The most important consequence of the premature stop codon is that the PCR-amplified *Citrus mitis* GT described above does not have a His tag at its C-terminus. Nevertheless, the primary amino acid sequences of the *Citrus unshiu* GT and PCR-amplified *Citrus mitis* protein are 98.0% identical. To express the latter protein in *E. coli*, the pCR2.1 vector carrying the *Citrus mitis* GT was digested with NdeI and SalI. The resulting 1.5 kb DNA fragment was ligated into pET29A cut with the same restriction enzymes. The resulting construct expresses the unmodified, native *Citrus mitis* GT protein as described above. The plasmid selected for further manipulation is referred to below as "pET29A/*Citrus mitis* GT". Cell-free extracts of BL21DE3 cells harboring the pET29A/*Citrus mitis* GT construct were generated essentially as described for heterologous expression of the Eucalyptus GT protein. Cell-free extract, containing 23 mg of protein per mL, was supplemented with 5% glycerol and stored at −80° C. for subsequent measurements of enzyme activity with pHBA and sinapic acid as substrates.

Initial rates of product formation were measured spectrophotometrically at 25° C. in a quartz cuvette (final reaction volume 0.5 mL) that contained 50 mM Tris-HCl (pH 7.3), 300 mM NaCl, 5 mM $MgCl_2$, 10 mM UDP-glucose, and a 10 mM final concentration of pHBA or sinapic acid; 50 μL of the cell-free extract described above was used to initiate the reaction. These are the exact same conditions that were used to determine the substrate specificity (pHBA versus sinapic acid) of the other plant UDP-glucosyltransferases that were previously characterized in Table 2 of Example 4. As shown in Table 4, like the Grape and Eucalyptus GTs, the unmodified *Citrus mitis* protein strongly preferred pHBA as a substrate, and the initial velocity of glucosylation of this compound was at least six times faster than the corresponding reaction with sinapic acid.

Since the unmodified *Citrus mitis* GT protein was poorly expressed in *E. coli* and would be difficult to purify, Applicants created a His-tagged fusion protein that would be easy to purify, taking advantage of the new sequence information (i.e., SEQ ID NO:30). To this end the flanking regions of the ORF of the *Citrus mitis* GT were modified by PCR for insertion into the high-level *E. coli* expression vector, pET29a(+) (Novagen). This was accomplished using Primers 14 and 16 and purified DNA of the pCR2.1 *Citrus mitis* GT plasmid described above as the target for amplification.

Primer 16-
5'-CTGGTCCGgtcgacTGACTCCACCAATTC-3' (SEQ ID NO:32)

The underlined bases hybridize to the target gene, while lower case letters indicate the restriction sites (NdeI or SalI) that were added to the ends of the PCR primers. Primer 14 hybridizes at the start of the gene and introduces an NdeI site at the initiation codon, while Primer 16 introduces a SalI site, lacks a stop codon and creates an in-frame fusion to sequences of the pET29A vector encoding a peptide of 15 amino acids comprising a C-terminal hexa-histidine tail. The resulting plasmid contains an open reading frame set forth as SEQ ID 33. It is created by the nucleotide sequence of the *Citrus mitis* GT gene and nucleotide sequence of the pET29A vector. The primary amino acid sequence of the *Citrus mitis* protein variant with the C-terminal hexa-histidine tail is set forth as SEQ ID 34. The PCR reaction contained 50 mM KCl, 10 mM Tris-HCl (pH 9), 0.1% Triton X-100, 2.5 mM $MgCl_2$, 0.2 mM each dNTP, 5 units of Taq polymerase (MBI Fermentas, USA), 10 ng of the pCR2.1 vector carrying the *Citrus mitis* GT plasmid template and both PCR primers at a final concentration of 0.2 μM. Amplification was carried out for 25 cycles, each comprising 1.5 min at 94° C., 1.5 min at 55° C., and 2.5 min at 72° C. The PCR product was digested with NdeI and HindIII, gel-purified, and the resulting fragment was ligated into the *E. coli* expression vector, pET-29a(+) (Novagen) that was digested with the same restriction enzymes. The ligation reaction mixture was used to transform *E. coli* DH10B, and plasmid DNA from a representative colony was sequenced completely to check for PCR errors; none were found. The plasmid selected for further manipulation is referred to below as "pET29a/*Citrus mitis* GT His Tag".

To generate sufficient amounts of the *Citrus mitis* GT His Tag protein for enzyme purification and characterization, a 50-mL "seed" culture of recombinant BL21 DE3 cells harboring the pET29a/*Citrus mitis* GT His Tag plasmid was grown at 37° C. in LB media that contained kanamycin (50 μg/mL). The culture was diluted 200-fold into a shaker flask containing 2 liters of LB medium supplemented with 50 μg/mL of kanamycin. The culture was grown at 22° C. until the $OD_{600}$ had reached 0.6. At this point IPTG was added to a final concentration of 0.2 mM. The cells were cultured for 24 h, harvested by centrifugation, resuspended in 24 mL of GT extraction buffer (50 mM Tris/HCl pH 7.5, 300 mM NaCl, 5 mM $MgCl_2$, 2 mM DTT and passed twice through a French pressure cell at 20,000 psi. Unless otherwise noted, subsequent steps were at 0–4° C. Cell debris was removed by centrifugation (43,000×g, 90 min), and the resulting cell-free extract, containing ~32 mg of protein per mL, was supplemented with glycerol (5%) and stored at −80° C. for subsequent purification.

The *Citrus mitis* GT His Tag protein was purified by nickel chelate affinity chromatography as follows. Six 2.5-mL aliquots of the cell-free *E. coli* extract, corresponding to 500 mg of total *E. coli* protein, were desalted on PD10 columns (Amersham Pharmacia Biotech, USA) into Buffer A (20 mM sodium phosphate, 500 mM NaCl, 10 mM imidazole, pH 7.5). Three and a half milliliters of the desalted sample was loaded onto a 5-mL HiTrap chelating HP cartridge (Amersham Pharmacia Biotech, USA) at a flow rate of 1 mL/min. The cartridge was washed with 20 mL of Buffer A at 1 mL/min followed by 20 mL of 60 mM imidazole in Buffer A at the same flow rate. The loading and washing steps were repeated five more times, and the *Citrus mitis* GT His Tag protein was then eluted from the column with a gradient in which the imidazole concentration was raised from 60 mM to 500 mM over a 20 min period at a flow rate of 1 mL/min; 1.5 mL fractions were collected.

Fractions containing *Citris mitis* GT His Tag enzyme activity were identified using the visual assay with sinapic acid and UDP-glucose that was previously described for the Grape GT (Example 5). Aliquots (~6 µl) of appropriate fractions were analyzed by SDS-PAGE, and visual inspection of Coomassie-stained gels identified a fraction in which the recombinant *Citrus mitis* GT His Tag protein was >90% pure. The column fraction was diluted to 2.5 mL with GT extraction buffer, and the entire sample was buffer exchanged on a PD-10 gel filtration column (Pharmacia, Piscataway, N.J.), pre-equilibrated with GT extraction buffer. The 3.5-mL desalted sample was supplemented with 5% glycerol and concentrated to a final volume of 200 µl using a Centricon-10 (Millipore Corp.). The final concentration of the purified recombinant *Citrus mitis* GT His Tag protein was 0.484 mg of protein per mL, which corresponds to a monomer concentration of 8.33 µM. Protein concentration was calculated using an extinction coefficient of 69,520 $M^{-1} M^{-1}$ at 280 nm, as determined by the GCG Peptidesort program using the amino acid composition given in SEQ ID NO:34.

The kinetic properties of the *Citrus mitis* GT His Tag protein were characterized using pHBA as a substrate as previously described in Example 7, but assays were initiated by addition of 0.0666 µM of the purified enzyme. The formation of the pHBA ester glucoside was monitored at 304 nm, and the data was fit to the Michaelis-Menten equation. Under these conditions, the apparent Km and Vmax values were 0.80 mM and 7.08 µM/min, respectively. Taking into account the amount of enzyme that was present in the assay, the latter value corresponds to a turnover number ($k_{cat}$) of ~1.77 $sec^{-1}$ when the enzyme is saturated with pHBA.

The relative substrate specificity for pHBA versus sinapic acid was also determined for the purified *Citrus mitis* GT His Tag protein under saturating conditions. For consistency, this was done as before spectrophotometrically at 25° C. in a quartz cuvette that contained 50 mM Tris-HCl (pH 7.3), 300 mM NaCl, 5 mM $MgCl_2$, 10 mM UDP-glucose, and a 10 mM final concentration of pHBA or sinapic acid; the final volume was 0.5 mL and 10 µL of purified enzyme was used to start the reaction. These are the same conditions that were used to determine the substrate specificity (pHBA versus sinapic acid) of the crude extracts that were characterized in Table 2. The results reveal that the purified *Citrus mitis* His Tag protein has essentially the same relative substrate specificity for pHBA versus sinapic acid (4.88) as the unmodified protein that was used in Table 4 (6.35), suggesting that the C-terminal extension does not significantly alter enzyme activity.

Finally, HPLC analysis (as described in Example 6) confirmed that the purified *Citrus mitis* GT His Tag protein only attaches glucose to the carboxyl group of pHBA; no pHBA phenolic glucoside was detected in the chromatograms. Taken together the above observations provide compelling evidence that the *Citrus mitis* GT, with or without a His Tag, is an excellent catalyst for pHBA ester glucoside formation.

Example 9

Generation of Transgenic Tobacco Plants that Overproduce pHBA

As already indicated, Applicants have discovered a novel subfamily of UDP-glucosyltransferases (that includes members from grape, eucalyptus, and citrus) that only attach glucose to the carboxyl group of small aromatic compounds, even ones that also have a hydroxyl group. The distinguishing feature of these enzymes is that they all exhibit a marked preference for pHBA as a substrate, in comparison to other hydroxybenzoic acid or hydroxycinnamic acid derivatives. This conclusion is not based on the standard definition of catalytic efficiency ($k_{cat}$/Km), but on an operational definition that takes into account other considerations that are important for overexpressing these proteins in heterologous plants to alter the partitioning of pHBA glucose conjugates, potentially affecting product accumulation. As indicated in the equation that is used to calculate catalytic efficiency (Kcat/Km), two enzymes with the same value for this parameter can have very different turnover numbers, depending on their respective Kms. However, if both enzymes are saturated with substrate, the one with the highest Kcat is the most effective catalyst for our purposes. Controlling the partitioning of glucose conjugates in transgenic plants that produce large amounts of pHBA required that the work focus on the maximum rate of glucosylation when the enzyme is saturated with pHBA.

In a similar vein, substrate inhibition (i.e., by the aglycone substrate) is also another very important consideration and something to be avoided if maximum production of pHBA is to be achieved. As shown in Table 2, the Grape GT is strongly inhibited by 10 mM sinapic acid (~80%), yet little, if any, substrate inhibition is observed with the same concentration of pHBA. Also apparent in Table 2, several of the other plant glucosyltransferases are also susceptible to substrate inhibition, albeit to various degrees. Finally, metabolic chaos and phenotypic abnormalities could result if a foreign protein that indiscriminately glucosylates key intermediates in the plant phenylpropanoid pathway was over-expressed in the cytosol. Thus, UDP-glucosyltransferases that are more active with hydroxycinnamic acid derivatives than they are with pHBA were not preferred.

The three UDP-glucosyltransferases disclosed herein satisfy these criteria in a test tube. The important question is: Will they behave as predicted in pHBA-overproducing plants? Most preferred embodiments of the invention would be transgenic plants that only accumulate the pHBA ester glucoside in any compartments of interest, including leaf, stem, and root tissue. To achieve this goal, the foreign GT will have to have a high enough turnover number to effectively compete with the endogenous plant enzymes that would normally partition pHBA to the phenolic glucoside. Described below are the first in vivo experiments with the Grape GT in CPL-expressing tobacco plants that over produce pHBA.

PCR-Cloning of *E. coli* CPL

Two PCR primers were used to amplify the *E. coli* ubiC gene from genomic DNA, while adding unique restriction sites to its flanking regions for subsequent ligation into a high copy number plasmid. This gene codes for chorismate pyruvate lyase, which is referred to below as CPL. The primers used for this purpose were based on the published DNA sequences of the *E. coli* ubiC gene (GenBank® Accession number M96268) and consisted of the following nucleotides:

Primer 17-: 5'-CTA CTC ATT Tca tat gTC ACA CCC CGC GTT AA-3'     (SEQ ID NO:35)

Primer 18-: 5'-CAT CTT ACT aga tct TTA GTA CAA CGG TGA CGC C-3'     (SEQ ID NO:36)

The underlined bases hybridize to the target gene, while lower case letters indicate the restriction sites (NdeI or BglII) that were added to the ends of the PCR primers.

Amplification of the *E. coli* ubiC gene was achieved using Primers 17 (SEQ ID NO:35) and 18 (SEQ ID NO:36), and genomic DNA from *E. coli* strain W3110 (Campbell et al., *Proc. Natl. Acad. Sci.* 75:2276–2284 (1978)). Primer 17 hybridizes at the start of the gene and introduces a NdeI site at the protein's initiation codon, while Primer 18 hybridizes at the opposite end and provides a BglII site just past the termination codon. The 100 µL PCR reactions contained ~100 ng of genomic DNA and both primers at a final concentration of 0.5 µM. The other reaction components were provided by the GeneAmp® PCR Reagent Kit (Perkin Elmer), according to the manufacturer's protocol. Amplification was carried out in a DNA Thermocycler 480 (Perkin Elmer) for 22 cycles, each comprising 1 min at 94° C., 1 min at 55° C., and 1 min at 72° C. Following the last cycle, there was a 7-min extension period at 72° C.

The PCR product was cut with NdeI and BglII, and the resulting fragment was ligated into the *E. coli* expression vector, pET-24a(+) (Novagen) that had been digested with NdeI and BamHI. The ligation reaction mixture was used to transform *E. coli* DH10B electocompetent cells (GibcoBRL-Life Technologies) using a BTX Transfector 100 (Biotechnologies and Experimental Research Inc.) according to the manufacturer's protocol; growth was selected on LB media that contained kanamycin (50 µg/mL). Transformants that contained plasmids with a CPL insert were identified through PCR reactions, using Primers 17 (SEQ ID NO:35) and 18 (SEQ ID NO:36) and individual resuspended colonies as the source of template; from hereon, this technique is simply referred to as "colony PCR". Plasmid DNA was isolated from a representative colony that yielded a PCR product of the correct size, and the entire insert corresponding to CPL was sequenced completely to check for PCR errors; none were found. The plasmid that was selected for further manipulation is referred to below as "pET24a-CPL". The nucleotide sequence of the ORF for CPL in the pET24a *E. coli* expression construct and its predicted primary amino acid sequence are set forth in SEQ ID NO:37 and SEQ ID NO:38, respectively.

Construction of a Chloroplast-Targeted Version of CPL: TP-CPL

It is known that chorismate is localized in chloroplasts and other types of plastids (Siebert et al., *Plant Physiol.* 112:811–819 (1996)) and it was therefore essential to provide CPL with an N-terminal chloroplast targeting sequence that would efficiently direct the foreign protein to chloroplasts, the site of chorismate production. This was accomplished by constructing a chimeric protein that consists of a chloroplast targeting sequence that is derived from the tomato Rubisco small subunit precursor protein fused to the initiator Met residue of CPL; the resulting fusion protein is referred to below as "TP-CPL". PCR was employed to generate a DNA fragment corresponding to the transit peptide of the Rubisco small subunit and first four amino acid residues of "mature" Rubisco. The target for amplification was the plasmid pTSS1-91-(#2)-IBI (Siebert et al., *Plant Physiol.* 112:811–819 (1996)), which contains a full-length cDNA clone of the tomato Rubisco small subunit precursor for rbcS2 (Sugita et al., *Mol Gen Genet.* 209:247–256 (1987); Siebert et al., *Plant Physiol.* 112:811–819 (1996)). The following primers were used this reaction:

```
Primer 19-: 5'-CTA CTC ACT TAG ATC Tcc atg gCT TCC TCT GTC ATT TCT-3'   (SEQ ID NO:39)

Primer 20-: 5'-CAT CTT ACT cat atg CCA CAC CTG CAT GCA GC-3'            (SEQ ID NO:40)
```

The underlined portion of Primer 19 (SEQ ID NO:39) hybridizes to the first 21 nucleotides of the Rubisco small subunit precursor and introduces an NcoI site (lower case letters) at the initiator Met residue at the start of the chloroplast targeting sequence. As indicated, this primer also contains a BglII site (bold letters) at its 5' end, that is just upstream from the NcoI site. Primer 20 (SEQ ID NO:40) hybridizes at the other end of the chloroplast targeting sequence to nucleotides 167–184 of the ORF of the Rubisco small subunit precursor. A unique NdeI site was engineered into this primer (lower case letters) to allow attachment of the PCR fragment containing the chloroplast targeting sequence to the NdeI site that is situated at the start codon of CPL in the pET-24a expression construct. The 100-µL PCR reaction contained ~75 ng of pTSS1-91-(#2)-IBI and Primers 19 (SEQ ID NO:39) and 20 (SEQ ID NO:40) both at a final concentration of ~0.9 µM. Amplification was carried out in a DNA Thermocycler 480 (Perkin Elmer) for 25 cycles, each comprising 1 min at 94° C., 1 min at 55° C., and 1 min at 72° C.; the last cycle was followed by a 7-min extension period at 72° C.

The PCR product was digested with BglII and NdeI, and ligated into pET24a-CPL that had been cleaved with the same restriction enzymes to remove a small DNA fragment (106 bp) that contained only vector sequence, including the T7 promoter. The ligation reaction mixture was introduced into *E. coli* DH10B using electroporation, and growth was selected on LB media with kanamycin (50 µg/mL). Transformants harboring plasmids with the inserted chloroplast targeting sequence were identified by colony PCR using Primers 18 (SEQ ID NO:36) and 19 (SEQ ID NO:39). A representative plasmid yielding a PCR product of the correct size was selected for further manipulation; this plasmid is referred to below as "pET24a-TP-CPL". To confirm the absence of PCR errors, the region of the-plasmid corresponding to the amplified chloroplast targeting sequence was sequenced completely using custom designed primers. The nucleotide sequence of the ORF for TP-CPL and its predicted primary amino acid sequence are set forth in SEQ ID NO:41 and SEQ ID NO:42, respectively.

Construction of the Expression Plasmid used for Tobacco and *Arabidopsis* Transformation A construct that could be used for constitutive expression in tobacco and arabidopsis was constructed by subcloning the DNA fragment corresponding to the full-length TP-CPL fusion protein into a modified version of plasmid pML63. The latter was derived from pML40, which contains the following genetic elements: a CaMV 35S promoter, a cab leader sequence, the uidA coding region, and the NOS polyadenylation signal sequence. Briefly, the CaMV 35S promoter is a 1.3 kb DNA fragment that extends 8 base pairs past the transcription start site (Odell et al., *Nature* 303:

810–812 (1985)). Operably linked to its 3' end is the cab leader sequence, a 60 bp untranslated double-stranded piece of DNA that was obtained from the chlorophyll a/b binding protein gene 22L (Harpster et al., *Mol. Gen. Genet* 212: 182–190 (1988)). Fused to the 3' end of the cab leader is the uidA gene (Jefferson et al. (1987) *EMBO J.* 6:3901) that encodes the protein β-glucuronidase (e.g., "GUS"). Finally, attached to 3' end of the GUS gene is an 800 bp DNA fragment containing the polyadenylation signal sequence from the nopaline synthase (e.g., "NOS") gene (Depicker et al., *J. Mol. Appl. Genet.* 1:561–564 (1982)). These DNA fragments, together comprising a 35S-GUS chimeric gene, were inserted by standard cloning techniques into the vector pGEM9Zf (–) (Promega; Madison Wis.) to yield plasmid pMH40.

Plasmid pML63, which is basically the same as pMH40 but has a truncated version of the 3' NOS terminator sequence, was generated in the following manner. First, pMH40 was digested with SalI and the two resulting DNA fragments of 4.03 kb and 2.9 kb were re-ligated to yield a plasmid, pML3, with the 35S promoter/cab22 leader/GUS gene/3' NOS terminator cassette in the opposite orientation. pML3 was then digested with Asp718 I and HindIII to release a 770 bp fragment that contained the 3' NOS terminator sequence. The latter was discarded and replaced with a shorter version that was generated by PCR using pMH40 as a template and Primers 21 (SEQ ID NO:43) and 22 (SEQ ID NO:44).

```
Primer 21-:
                                      (SEQ ID NO:43)
5'-CCC GGG GGT ACC TAA AGA AGG AGT GCG TCG AAG-3'

Primer 22-:
                                      (SEQ ID NO:44)
5'-GAT ATC AAG CTT TCT AGA GTC GAC ATC GAT CTA GTA
ACA TAG ATG A-3'
```

The PCR product was digested with HindIII and Asp718 I to yield a 298 bp fragment that contains 279 bp of the 3' NOS terminator sequence, starting at nucleotide 1277 (the TAA stop codon) and ending at nucleotide 1556 of the published sequence (Depicker et al., *J. Mol Appl Genet* 1:561–574 (1982)). Ligation of this PCR fragment into the truncated version of pML3 resulted in plasmid pML63.

As indicated above, pML63 contains the GUS coding region under the control of the 35S promoter and a truncated version of the 3' NOS terminator. It therefore contains all of the transcriptional information that is necessary for the constitutive expression of GUS in plants. To generate an analogous construct for TP-CPL, plasmid pML63 was digested with NcoI and EcoRI. This manipulation releases only the GUS gene insert, leaving the regulatory flanking sequences and the rest of the vector intact. Plasmid pet24a-TP-CPL was also treated with NcoI and EcoRI, which liberates the entire coding region of the TP-CPL fusion protein. The small DNA fragment (693 bp) corresponding to the latter was purified by agarose gel electrophoresis and subjected to a standard ligation reaction with the large vector fragment (4.63 bp) that was obtained from cutting pML63 with Nco I and EcoRI. The ligation reaction mixture was introduced into *E. coli* DH10B using electroporation, and growth was selected on LB media that contained ampicillin (100 µg/mL). Transformants harboring plasmids with the inserted TP-CPL coding sequence were identified by colony PCR using Primers 18 (SEQ ID NO:36) and 19 (SEQ ID NO:39). A representative plasmid that yielded a PCR product of the correct size was selected for further manipulation. This construct is referred to below as "TP-CPL-pML63".

The binary vector that was used for Agrobacterium-mediated, leaf disc transformation of tobacco was the plasmid pZBL1 (ATCC 209128). pZBL1 contains the origin of replication from pBR322, the bacterial nptI kanamycin resistance gene, the replication and stability regions of the *Pseudomonas aeruginosa* plasmid pVS1 (Itoh et al., *Plasmid* (1984), 11 (3), 206–220), T-DNA borders described by van den Elzen et al. (*Plant Mol. Biol.* (1985), 5(3), 149–154) wherein the OCS enhancer (extending from –320 to –116 of the OCS promoter (Greve et al., *J. Mol. Appl. Genet.* 1:499–511(1983)) that is part of the right border fragment is removed, and a NOS/P-nptII-OCS 3' gene inserted to serve as a kanamycin resistant plant selection marker.

For expression of TP-CPL, plasmid pZBL1 was digested with Sal I which cuts at a unique site between the right and left borders that is ideally situated for the insertion of foreign genes and stable integration into the plant genome. To minimize the possibility of re-ligation without an insert, the cut vector was dephosphorylated using Calf Intestinal Alkaline Phosphatase (GibcoBRL-Life Technologies) according to the manufacturer's recommendations. Plasmid TP-CPL-pML63 was also digested with SalI to generate the fragment that would be inserted into the binary vector. This treatment releases the entire transcriptional unit for the TP-CPL fusion gene (e.g., 35S promoter/cab22 leader/TP-CPL/3' NOS terminator) as a 2.4 kb DNA fragment. The latter was purified by agarose gel electrophoresis and subjected to a standard ligation reaction with the dephosphorylated 11.0 kb fragment that was obtained from pZBL1 as described above. The ligation reaction mixture was introduced into *E. coli* DH10B using electroporation, and growth was selected on LB media with kanamycin (50 µg/mL).

Transformants harboring plasmids with the TP-CPL fusion gene were identified by colony PCR using Primers 18 (SEQ ID NO:36) and 19 (SEQ ID NO:39), and the orientation of the insert was determined by restriction digestion analysis using KpnI. The plasmid that was selected for further manipulation, referred to below as "TP-CPL-pZBL1". As described below, this expression construct was used to transform tobacco and arabidopsis for overproduction of pHBA.

Generation of Transgenic TP-CPL-Expressing Tobacco Plants

Plasmid TP-CPL-pZBL1 was introduced into *Agrobacterium tumefaciens* strain LBA4404 (Hoekema et al., *Nature* 303:179–180 (1983)) using the freeze-thaw transformation procedure (Holsters et al., (1978) *Mol. Gen. Genet.* 163: 181–187)). The cells were plated at 28° C. on YEP media (10 g Tryptone, 10 g Yeast Extract, and 5 g NaCl per liter) that also contained kanamycin (1000 µg/mL) and rifampicin (20 µg/mL). Colonies harboring the binary construct were identified by PCR using appropriate primers.

Potted tobacco plants (*Nicotiana tabacum* cv. Xanthi) for leaf disk infections were grown in a growth chamber maintained for a 14 h, 21° C. day/10 h, 18° C. night cycle, with approximately 80% relative humidity, under mixed cool white fluorescent and incandescent lights. Agrobacterium-mediated, leaf disk transformations were performed essentially as described by De Blaere et al., (*Meth. Enzymol.* 153:277–292) with the following modifications. Leaf disks, 8 mM in diameter, were prepared from whole leaves using a sterile paper punch and 4-to 6-week-old plants. Leaf disks were inoculated by submerging them for 30 min in concentrated solution of Agrobacterium harboring TP-CPL-pZBL1 resuspended to an $OD_{600}$ of 0.8 in Murashige's Minimal Organics Media. Inoculated leaf disks were placed directly on media, that contained (per liter) 30 g of sucrose, 1 mg of 6-benzylaminopurine (BAP), 0.1 mg of napthaleneacetic acid, 8 g of agar, and 1 package of Murashige's Minimal Organics Medium that was obtained from GibcoBRL-Life Technologies (cat. #23118-029). After incubation for 3 d at 28° C. in the light, leaf disks were transferred to fresh media of the same composition that also contained kanamycin (300 μg/mL) and cefotaxime (500 μg/mL) to select for the growth of transformed tobacco cells and eliminate residual Agrobacterium. Leaf disks were incubated under the growth conditions described above for 3 weeks and were then transferred at 3-week intervals to fresh media of the same composition until optimal shoot size was obtained for root induction. Shoots were rooted on media containing (per liter) 1 package of Murashige's Minimal Organics Medium, 8 g of agar, and 10 g of sucrose. Approximately 4 weeks later, the plants were transferred to soil and allowed to grow to maturity in a growth chamber under the conditions described above.

Preparation of Tobacco Leaf Samples and HPLC Analysis of pHBA Glucose Conjugates.

Healthy leaf tissue (50–100 mg fresh weight) was rapidly removed from the distal one third portion of the leaf and placed in a Biopulverizer™ H Tube (cat. # 6570-201 or 6540-401) that contained a ceramic bead; both of the latter were obtained from QBiogen (Carlsbad, Calif.). After the addition of 1 mL of 50% methanol (v/v), the tubes were capped and mechanically agitated at room temperature for 40 sec, using a FastPrep® FP120 (QBiogen) tissue disruption apparatus that was operating at a speed of 5 m/sec. The tubes were then placed on a rotary shaker and vigorously agitated at 400 rpm for 1 h at room temperature. The extract was clarified by centrifugation (10,000×g, 10 min) using a conventional tabletop microfuge, and the supernatant which contained both pHBA glucose conjugates was carefully removed to an empty tube.

In the next step, a 50-μl aliquot of the methanol extract was transferred to a fresh microfuge tube, and the sample was taken to complete dryness under vacuum in a Speed-Vac® (Thermo Savant, Holbrook, N.Y.), using the optional heat setting. The dry residue was dissolved in 100 μl of 5 mM Tris-HCl (pH 8), and the sample was passed through a 0.22 μm cellulose acetate filter to remove small particles; a Spin-X Centrifuge Tube Filter (Costar®-Corning Inc. Life Sciences, Acton, Mass.; cat. #8160) was used for this purpose.

An aliquot (10–80 μl) of the filtered sample was then applied to a Vydac 218TP54 Protein and Peptide C18 column (Grace Vydac, Hesperia, Calif.) that was pre-equilibrated at 1 mL/min with 90% Buffer A (0.1% formic acid in water) and 10% Buffer B (methanol). Following sample injection, the column was developed at a 1 mL/min with a linear gradient of 10–50% Buffer B, over a 20-min period. Elution of pHBA glucose conjugates was monitored spectrophotometrically at 254 nm. Chemically synthesized pHBA phenolic and ester glucoside standards were used to calibrate the HPLC runs for retention times, and extinction coefficients for both compounds were accurately determined under the conditions employed. Peak areas were integrated using the software package provided with the Hewlett Packard Chemstation, and values obtained with known amounts of the chemical standards were used to quantitate micrograms of pHBA glucosides per injection. After accounting for the fraction of the original methanol extract that was injected on the column, the numbers were corrected to reflect recovery from the entire leaf sample that was extracted. This, coupled with an individual measurement of the dry weight of the leaf tissue analyzed (e.g., obtained from the same leaf, from the same plant, on the same day of analysis), enabled the expression of pHBA-glucosides as a percentage the total dry weight. To calculate the total amount of pHBA that was attached to glucose and express this number as a percentage of the total dry weight (i.e., "pHBA (% of dry weight)"), the phenolic and ester glucoside were added together and multiplied by 0.46. This manipulation corrects for the mass of the associated glucose moiety, which is 54% of the total mass of both glucose conjugates.

Analysis of Transgenic Tobacco Plants Expressing TP-CPL

As described above, TP-CPL was introduced into tobacco (*Nicotiana tabacum*) using agrobacterium-mediated, leaf disc transformation to determine its influence on the accumulation of pHBA glucosides. The analysis was conducted on leaf tissue that was obtained from 15 tobacco plants (primary transformants) that resulted from different transformation events. After 5 weeks in soil, the plants exhibited various levels of pHBA glucosides, ranging from 0–2.3% of the total dry weight. Phenotypic variation is typically observed in nearly all plant transformation experiments, and presumably reflects different levels of gene expression that result from so-called "positional" effects (e.g., stable integration of the trait gene at different locations in the genome) and transgene copy number. That a similar phenomena also occurred in the present study is supported by Western blot analysis of the tobacco transformants using antisera directed against purified recombinant *E. coli* CPL. For example, although the majority of the plants (14 of 15) had immunologically detectable levels of the foreign protein, there was considerable variation in the levels of expression. Generally speaking, however, there was a positive correlation between the strength of the Western signal and the accumulation of pHBA glucosides, consistent with previous observations (Siebert et al., *Plant Physiol.* 112:811–819 (1996)); Sommer et al., *Plant Cell Physiol.* 39(11):1240–1244 (1998); Sommer et al., *Plant Cell Reports* 17:891–896 (1998)). The Western blot analysis described above also confirmed that the chloroplast-targeting sequence (transit peptide) is efficiently cleaved from the TP-CPL fusion protein when the latter is expressed in tobacco.

The mean pHBA glucoside content (±SEM) of the 5-week-old tobacco plants was 1.12%±0.186% of dry weight. However, one of the plants (transformant #34) had a pHBA glucoside content of 2.3% of dry weight. Like all the other transgenic tobacco plants expressing TP-CPL, the accumulation of pHBA glucosides in transformant #34 continued to increase as the plant matured. Indeed, after growing in soil for 13 weeks the leaf content of pHBA glucosides in this particular plant reached a level of about 8% of dry weight. The latter value corresponds to a total pHBA content of ~3.7% of dry weight, after correcting for the mass of the associated glucose molecule. As described in more detail below, primary transformant line 34 (CPL line 34) was self-crossed and the resulting T1 seeds were used to generate a pHBA-overproducing tobacco plant for trait-stacking experiments with the Grape GT. CPL line 34 resulted from a single integration event and was hemizygous for CPL, based on the observed segregation pattern (kanamycin resistance) of the T1 seeds from the self-crossed plant.

Example 10

Expression of the Grape GT in CPL-Expressing, pHBA-Overproducing Tobacco Plants Preparation of the Constitutive Grape GT Expression Construct To generate a construct for constitutive expression of the Grape GT in tobacco and arabidopsis, a 1465 bp BamHI/DraI DNA fragment, containing the full-length Grape GT ORF and 25 bp of 5' untranslated DNA immediately upstream from the initiation codon, was excised from the original cDNA plasmid (vmb1na.pk009.c8) and cloned into the binary vector pBE856 (SCP1-FlpM) that was cut with BamHI and HpaI. This resulted in replacement of the FlpM recombinase ORF in pBE856 with the Grape GT ORF, situated between the constitutive SCP1 promoter and 3' untranslated region of the potato proteinase inhibitor II (PIN II) gene. Ligation of the two blunt ends (DraI and HpaI) restored the disrupted termination codon of the Grape GT. The resulting binary vector, Grape GT expression construct, which is henceforth referred to as "pBE856 (SCP1-Grape GT)", was used for tobacco and arabidopsis transformations as described below.

Plasmid pBE856 (SCP-FlpM) was previously constructed by cloning a 2172 bp XbaI-EcoRI fragment containing a chimeric SCP1:FlpM:3' Pin gene into the multiple cloning site of the binary vector pBE673 (described below), after cleavage of the latter with XbaI and EcoRI. The SCP1:FlpM:Pin gene is comprised of a synthetic 35S promoter (SCP1) (Bowen et al., Synthetic constitutive promoters for high-level expression of foreign genes in plants. U.S. (2000), 31 pp., Cont.-in-part of U.S. Ser. No. 661,601, abandoned. CODEN: USXXAM U.S. Pat. No. 6,072,050 A 20000606), which is fused at its 3' end to the ORF of the FlpM recombinase, which is fused at its 3' end to the 3' PIN region derived from the *Solanum tuberosum* proteinase inhibitor II gene (GenBank® Accession L37519).

Plasmid pBE673 was derived from pBin 19 (GenBank® Accession No. U09365) by replacing an 1836 bp Bsu36a-ClaI fragment of pBin19, which contains the 3' end of the nopaline synthase (nos) promoter, the npt II (kanamycin resistance) ORF, and the 3' nos region, with a 949 bp Bsu36I-ClaI fragment that contains (5' to 3'): a 106 bp fragment comprising the 3' end of nos promoter (nucleotides 468–574 described in GenBank® accession nos. V00087 and J01541; see also Bevan et al., *Nucleic Acids Res.* 11 (2), 369–385 (1983)), a 5 bp GATCC sequence, a 551 bp fragment corresponding to the *Streptomyces hygroscopicus* phosphothricin acetyl transferase (basta resistance) ORF (GenBank® Accession No. X17220) except that the termination codon was changed from TGA to TAG, an 8 bp TCCGTACC sequence, and a 279 bp 3' nos region (nucleotides 1824–2102 of GenBank® Accession Nos. V00087 and J01541 described above).

Tobacco Transformation

Plasmid pBE856 (SCP1-Grape GT) was introduced into *Agrobacterium tumefaciens* strain LBA4404 (Hoekema et al., *Nature* 303:179–180 (1983) using a freeze-thaw transformation procedure (Holsters et al., *Mol. Gen. Genet.* 163:181–187). The cells were plated at 28° C. on LB media that contained kanamycin (50 μg/mL) and rifampicin (20 μg/mL), and one of the resulting single colonies was arbitrarily selected for tobacco transformation as described below.

T1 seeds from transgenic tobacco line CPL #34 which harbors the TP-CPL expression construct, were surface-sterilized, germinated, and grown under sterile conditions on MS media that contained kanamycin (0.2 mg/mL). Plants regenerated from stem explants containing two vegetative nodes were grown in Magenta boxes on MS media that contained kanamycin (0.05 mg/mL) and Timentin™ (0.1 mg/mL) (GlaxoSmithKline, Research Triangle Part, NC). The plants were grown for 4 weeks in a temperature- and light-regulated growth chamber set to 16 h, 23° C. d/8 h, 21° C. night cycles.

A 50-mL culture of the *Agrobacterium tumefaciens* strain harboring pBE856 (SCP1-Grape GT) was grown in LB media for 36 h at 30° C. The cells were harvested by centrifugation (7000×g), washed twice with 50 mL sterile MS medium, and finally resuspended in 40 mL of the same solution. Leaves from one of the regenerated TP-CPL tobacco plants described above were harvested under sterile conditions, cut into pieces of approximately 1.5 cm², and incubated in the agrobacterium suspension for 30 min at room temperature. Leaf explants were placed adaxial side down on shoot induction plates (Murashige's Minimal Organics Medium (GibcoBRL-Life Technologies), 3% sucrose, 1 mg/l benzyl aminopurine, 0.1 mg/l naphthalene-acetic acid, 0.8% agar) and incubated at room temperature for three d. Leaf explants were transferred to shoot induction media containing 5 mg/L glufosinate-ammonium (Fluka/Sigma Aldrich, St. Louis, Mo.), 25 mg/l kanamycin and 100 mg/L Timentin™ (GlaxoSmithKline) and subcultured to new media every three weeks. Plates were placed in growth chambers set to 16 h, 23° C. d/8 h; 21° C. night cycles. Excisable shoots were transferred to root induction media (Murashige's Minimal Organics Medium, 1% sucrose, 0.8% agar). Rooted shoots were transferred to soil, and the resulting plants were grown in a greenhouse. Five "CPL alone" control plants (C1–C5) were also regenerated at the same time from the same plant using the exact same procedure, but in this case the leaves were not incubated with agrobacterium and the glufosinate selection step was omitted.

Preparation of Tobacco Leaf Samples and HPLC Analysis of pHBA Glucose Conjugates.

Healthy leaf tissue (50–100 mg fresh weight) was rapidly removed from the distal third portion of the leaf and placed in a Biopulverizer™ H Tube (cat. # 6570–201 or 6540–401) that contained a ceramic bead; both of the latter were obtained from QBiogen (Carlsbad, Calif.). After the addition of 1 mL of 50% methanol (v/v), the tubes were capped and mechanically agitated at room temperature for 40 s, using a FastPrep® FP120 (QBiogen) tissue disruption apparatus that was operating at a speed of 5 m/s. The tubes were then placed on a rotary shaker and vigorously agitated at 400 rpm for 1 h at room temperature. The extract was clarified by centrifugation (10,000×g, 10 min) using a conventional tabletop microfuge, and the supernatant which contained both pHBA glucose conjugates was carefully removed to an empty tube.

In the next step, a 50-μl aliquot of the methanol extract was transferred to a fresh microfuge tube, and the sample was taken to complete dryness under vacuum in a Speed-Vac® (Thermo Savant, Holbrook, N.Y.), using the optional heat setting. The dry residue was dissolved in 100 μl of 5 mM Tris-HCl (pH 8), and the sample was passed through a 0.22 μm cellulose acetate filter to remove small particles; a Spin-X Centrifuge Tube Filter (Costar®-Corning Inc. Life Sciences, Acton, Mass.; cat. #8160) was used for this purpose.

An aliquot (10–80 µl) of the filtered sample was then applied to a Vydac 218TP54 Protein and Peptide C18 column (Grace Vydac, Hesperia, Calif.) that was pre-equilibrated at 1 mL/min with 90% Buffer A (0.1% formic acid in water) and 10% Buffer B (methanol). Following sample injection, the column was developed at a 1 mL/min with a linear gradient of 10–50% Buffer B, over a 20-min period. Elution of pHBA glucose conjugates was monitored spectrophotometrically at 254 nm.

Chemically synthesized pHBA phenolic and ester glucoside standards were used to calibrate the HPLC runs for retention times, and extinction coefficients for both compounds were accurately determined under the conditions employed. Peak areas were integrated using the software package provided with the Hewlett Packard Chemstation, and values obtained with known amounts of the chemical standards were used to quantitate micrograms of pHBA glucosides per injection. After accounting for the fraction of the original methanol extract that was injected on the column, the numbers were corrected to reflect recovery from the entire leaf sample that was extracted. This, coupled with an individual measurement of the dry weight of the leaf tissue analyzed (e.g., obtained from the same leaf, from the same plant, on the same day of analysis), enabled the expression of pHBA-glucosides as a percentage the total dry weight. To calculate the total amount of pHBA that was attached to glucose and express this number as a percentage of the total dry weight (i.e., "pHBA (% of dry weight)), the phenolic and ester glucoside were added together and multiplied by 0.46. This manipulation corrects for the mass of the associated glucose moiety, which is 54% of the total mass of both glucose conjugates.

UDP-Glucosyltransferase Assays

Leaf extracts from pHBA overproducing transgenic tobacco plants, with and without the Grape GT, were prepared in the following manner. Leaf samples (~0.2 g wet weight tissue) were homogenized with ~0.26 mL of an ice-cold solution containing 50 mM Tris-HCl (pH 7.5 at room temperature), 0.1% β-mercaptoethanol, 1 mM EDTA, and 75 mg/mL polyvinylpolypyrrolidone. All subsequent steps were conducted at 0–4° C., unless otherwise indicated. After centrifugation to remove debris (15,000×g, 10 min), the supernatant was filtered through a Spin-X Centrifuge Tube Filter (Costar®-Corning Inc. Life Sciences; cat. #8160), and supplemented with 6% glycerol. An aliquot of the filtrate (~200 µl) was then exchanged into Buffer Q (50 mM Tris-HCl, pH 7.6, 10 mM sodium sulfite, 1 mM EDTA, 300 mM NaCl, 6% glycerol, & 5 mM DTT) using a Microcon 10 concentrator (Millipore Corp.) and the following procedure: the sample was concentrated ~10-fold and diluted with 200 µL Buffer Q, and this wash step was repeated three times to yield the final preparation that was assayed for UDP-glucosyltransferase activity. pHBA ester glucoside forming activity was monitored spectrophotometrically as described in Example 4. The following assay conditions were used: Initial rates of enzyme activity were measured at 25° C. in a quartz cuvette (0.5 mL final reaction volume) that contained 50 mM Tris-HCl (pH 7.3), 300 mM NaCl, 5 mM $MgCl_2$, 10 mM UDP-glucose, 5 mM pHBA, and 25 µl of the above cell-free extracts. Reactions were initiated with the latter, and product formation as a function of time was calculated using the extinction coefficient for the pHBA glucose ester described in Example 4. Initial rates of glucosyltransferase activity were normalized for the protein concentration of the various extracts, and the results are expressed in terms of specific activity (i.e., pkats/mg of total protein). Protein concentrations were determined by the Bradford Method using bovine serum albumin as a standard.

CPL Enzyme Assays

Tobacco leaf extracts were prepared as described above, and CPL enzyme activity was measured at room temperature using a continuous spectrophotometric assay that monitors the conversion of chorismate to pHBA at 246 nm. Reactions were carried out in a 500-µl quartz cuvette that contained the following components: 50 mM Tris-HCl, pH 8.0, 200 mM NaCl, 100 µM purified chorismate, and 10–50 µl of leaf extract; the latter was used to start the reaction. The formation of pHBA was monitored at 246 nm, and initial velocities were used to calculate CPL enzyme activity (pkat/mg of protein), using an extinction coefficient of 10,946 $cm^{-1}$ $M^{-1}$. Protein was determined by the Bradford Method as described above.

Preparation of Tobacco Stalk Samples and HPLC Analysis of pHBA Glucose Conjugates All steps were conducted at room temperature. Forty-day-old tobacco plants growing in soil were cut at the base right above the ground and the leaves and associated stems were discarded. The entire stalk material (12–28 g fresh weight) was carefully weighed and cross-sectionally cut into small pieces (~1 cm long) using a pair of scissors. The tissue was transferred to a Waring blender and 9.0 mL of 50% methanol was added for each gram of tissue. The sample was homogenized three times at high speed (15-s pulses), and the resulting homogenate was then incubated for 1 h at room temperature with occasional stirring.

Following this procedure, the homogenate was subjected to three more 15-s pulses in the Waring blender, and a small aliquot of the methanol extract (~400 µl) was removed to a 1.5-mL polypropylene microfuge tube for further processing. Debris was removed by centrifugation (15,000×g, 10 min), and a 50-µl aliquot of the supernatant was transferred to a fresh microfuge tube. The sample was taken to complete dryness under vacuum in a Speed-Vac® (Thermo Savant), using the optional heat setting. The dry residue was dissolved in 100 µl of 5 mM Tris-HCl (pH 8), and the sample was filtered and subjected to HPLC analysis for pHBA glucosides as described above for methanol-extracted leaf tissue.

Characterization and Properties of Transgenic Tobacco Plants with CPL and Grape GT.

As already described, a glufosinate-selectable expression construct containing the Grape GT behind a synthetic 35S promoter (SCP1) was introduced into a CPL-expressing tobacco plant that originated from a single kanamycin-resistant seed obtained from self-crossed CPL #34. Fifty-five independent primary transformants containing both transgenes were regenerated and transferred to soil. As controls, five "CPL alone" plants were also regenerated at the same time using the exact same procedure, but without transformation or glufosinate selection. When the plants were 14 days old, leaf samples were extracted with 50% methanol and analyzed for pHBA glucose conjugates (Table 5). In the "CPL alone" control plants, the pHBA glucose ester accounted for 55.4±1.3% of the total pHBA glucose conjugates. In contrast, virtually all of the double transformants had a much higher percentage of the pHBA ester glucoside. Indeed, this compound was the only pHBA glucose conjugate that was detected in twelve of the plants that contained both genes.

These observations provide compelling evidence that the Grape GT effectively competes with the endogenous glucosyltransferases that normally form the pHBA phenolic glucoside, at least at this early stage of development.

Table 5 shows expression of the Grape GT in pHBA-overproducing plants increases the percentage of the pHBA ester glucoside. Methanol-extracted leaf tissue from 14-day-old plants was analyzed. "Total pHBA" represents the total amount of pHBA that was present in the two glucose conjugates, after correcting for the associated glucose moiety (i.e., the sum of the phenolic glucoside and ester glucoside multiplied by 0.46, as described in Example 10). The top line of the table shows the mean (±SEM) values for 5 "CPL alone" control plants.

TABLE 5

| Transgenic Plant | Total pHBA (% of Dry Weight) | pHBA Glucose Ester (% of Total pHBA Glucose Conjugates) |
|---|---|---|
| Control (n = 5) | 0.32 ± 0.04 | 55.4 ± 1.3 |
| 45 | 0.721 | 74 |
| 25 | 0.684 | 87 |
| 55 | 0.875 | 88 |
| 6 | 0.747 | 90 |
| 37 | 0.764 | 90 |
| 38 | 0.864 | 93 |
| 43 | 0.896 | 93 |
| 50 | 0.638 | 93 |
| 49 | 0.936 | 93 |
| 13 | 0.675 | 94 |
| 40 | 1.084 | 94 |
| 20 | 0.840 | 94 |
| 9 | 0.904 | 94 |
| 54 | 1.209 | 94 |
| 12 | 1.002 | 94 |
| 15 | 0.667 | 94 |
| 51 | 1.049 | 95 |
| 27 | 0.990 | 95 |
| 18 | 0.908 | 95 |
| 42 | 1.071 | 95 |
| 5 | 1.105 | 96 |
| 32 | 1.017 | 96 |
| 23 | 1.324 | 96 |
| 31 | 1.019 | 96 |
| 35 | 1.071 | 96 |
| 7 | 1.296 | 96 |
| 8 | 1.155 | 96 |
| 22 | 1.014 | 96 |
| 14 | 1.146 | 96 |
| 3 | 1.561 | 97 |
| 1 | 1.207 | 97 |
| 33 | 1.367 | 97 |
| 10 | 1.548 | 98 |
| 28 | 1.372 | 98 |
| 48 | 1.461 | 98 |
| 52 | 1.588 | 98 |
| 44 | 1.468 | 98 |
| 46 | 1.552 | 98 |
| 34 | 2.226 | 99 |
| 21 | 1.894 | 99 |
| 30 | 0.707 | 100 |
| 26 | 0.831 | 100 |
| 41 | 0.986 | 100 |
| 19 | 1.105 | 100 |
| 36 | 1.174 | 100 |
| 29 | 1.209 | 100 |
| 4 | 1.243 | 100 |
| 53 | 1.508 | 100 |
| 11 | 1.537 | 100 |
| 47 | 1.564 | 100 |
| 2 | 1.582 | 100 |
| 39 | 1.945 | 100 |

Unexpectedly, most of the double transformants also had significantly higher levels of total pHBA, and there was a reasonable correlation between this parameter and the fractional percentage of the ester glucoside (Table 5). For example, focusing on the extremes, the total pHBA content of the control plants was 0.32%±0.04% (based on dry weight), which is typical for plants at this age. In contrast, all 20 plants harboring the Grape GT that contained 98–100% ester glucoside had an average pHBA content of 1.42±0.08%. Indeed, the pHBA content of one of the plants (line 34) was 2.23% of DW, which is nearly a 7-fold increase over the control population.

Shown in Table 6 are UDP-glucosyltransferase activities for four double transformants and two "CPL alone" control plants. As already indicated, the spectrophotometric assay developed for these measurements specifically monitors the formation of the pHBA glucose ester. As anticipated, the "CPL alone" control plants, which had only accumulated 52–59% of their total pHBA as the ester glucoside (Table 5), exhibited the least amount of enzyme activity (Table 6). On the other hand, double transformant line 34, which had 99% ester glucoside and the highest level of pHBA (2.2% of dry weight) as shown in Table 5, also had the highest UDP-glucosyltransferase activity—at least 10 times greater than either of the "CPL alone" control plants. Although not perfect, here is also a reasonable correlation between in vitro UDP-glucosyltransferase activity (Table 6) and in vivo partitioning to the pHBA ester glucoside (Table 5) for the three other double transformants.

Table 6 shows pHBA ester glucoside forming activity in leaf extracts prepared from four different CPL/Grape GT double transformants (lines 34, 39, 47, and 53) and two "CPL alone" control plants (C-1 and C-2). The plants were thirty three days old at the time of analysis. Initial rates of pHBA glucose ester formation are expressed as pkats/mg of total extract protein.

TABLE 6

| Transgenic Plant | pHBA-GT Activity (pkats/mg) | |
|---|---|---|
| C-1 | 28.6 | |
| C-5 | 37.8 | Ave. = 33.2 |
| 34 | 382 | |
| 39 | 281 | |
| 47 | 319 | |
| 53 | 234 | Ave. = 304 |

To rule out the possibility that the increased levels of pHBA in the double transformants simply reflect higher levels of CPL gene expression, leaf extracts were prepared from several of the plants and CPL enzyme activity was measured, using a continuous spectrophotometric assay that monitors the conversion of chorismate to pHBA at 246 nm. The plants had been growing in soil for 34 d at the time of analysis. The initial velocities for double transformants lines 39, 47, and 53 (three of the highest pHBA overproducers) were 187, 222, and 167 pkats/mg of protein, respectively, while the values for two "CPL alone" control plants ranged from 138–210 pkats/mg of protein. Based on this observation, Applicants concluded that stacking the two transgenes together did not result in higher levels of CPL gene expression, and that some other factor must be responsible for the elevated levels of pHBA that were observed in the plants with the Grape GT.

Previous experiments with fully mature CPL-expressing tobacco plants have shown that the phenolic glucoside is the only pHBA glucose conjugate in stem tissue. It was therefore of interest to see if the Grape GT could effectively compete with the naturally occurring UDP-glucosyltransferases that are present in a tissue that is largely devoted to lignin biosynthesis, to partition pHBA to the desired ester glucoside. To address this question, one of the double transformants (line 44) and a CPL control plant that were both about five and a half weeks old were sacrificed, and the entire stalk material from each of the plants was extracted with 50% methanol and analyzed by HPLC. Consistent with previous results, the control extract only contained the pHBA phenolic glucoside. In contrast, the ester glucoside was the predominant species (>90%) in the stalk extract that was prepared from the double transformant. This observation, coupled with the results obtained with leaf tissue, strongly suggest that we have created transgenic tobacco plants that for all intents and purposes, only contain the pHBA ester glucoside, at least at this stage of development.

Table 7 summarizes the situation after six and a half weeks in soil for the 14 double transformants that we continued to monitor. The leaf content of pHBA had increased dramatically since the initial screening, and a number of the plants still had essentially no phenolic glucoside. More important, the leaf content of pHBA in transformant line 21 had already reached 4.3% of the total dry weight, which is very close to the 4.6% threshold level that was previously established with tobacco plants that only express CPL. However, the latter value was only observed in a fully mature 13-week-old tobacco plant, not at this early stage of development.

Table 7 shows pHBA accumulation in the CPL/Grape GT double transformants. Methanol-extracted leaf tissue was analyzed for pHBA glucose conjugates; the plants were 46 days old at the time of analysis. "Total pHBA" represents the total amount of pHBA that was present in the two glucose conjugates, after correcting for the associated glucose moiety (i.e., the sum of the phenolic glucoside and ester glucoside multiplied by 0.46, as described in Example 10). The top line of the table shows the mean values (±SEM) for four "CPL alone" control plants.

TABLE 7

Figure 3:
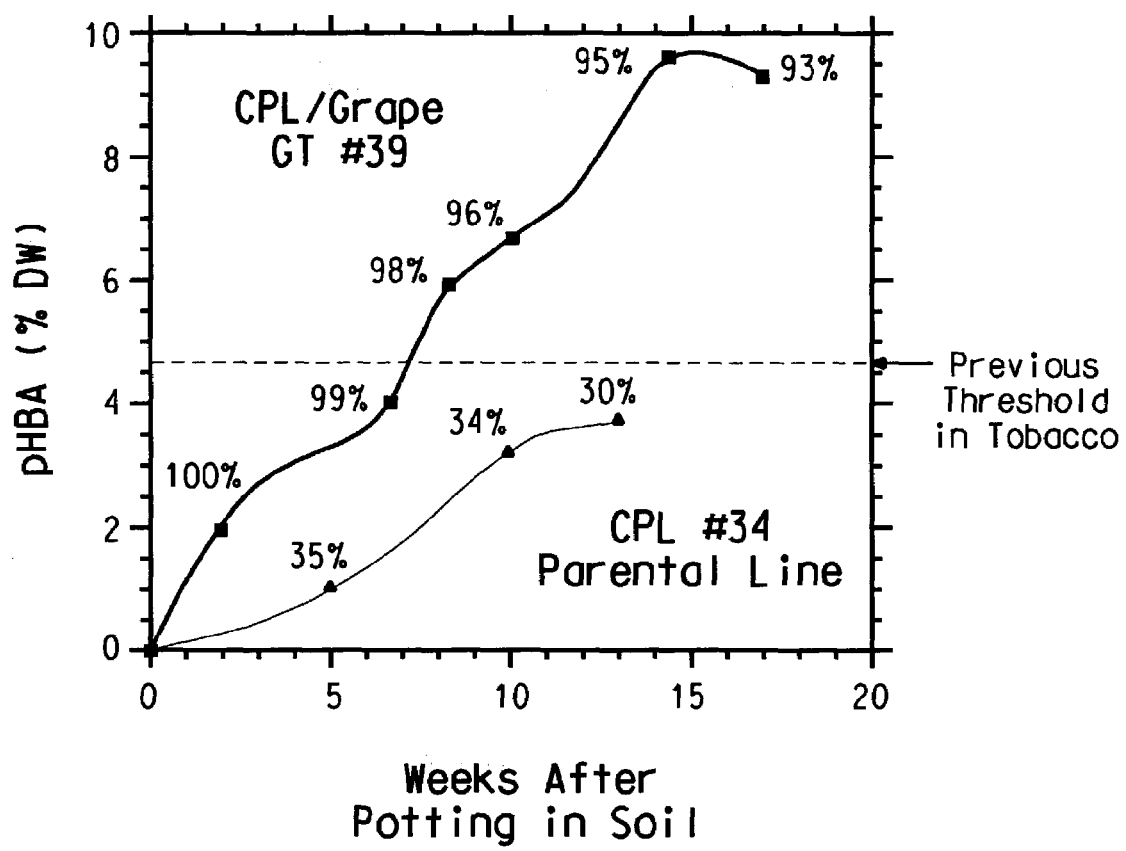
FIG. 3 shows the developmental time course for pHBA accumulation in leaf tissue obtained from a tobacco CPL/Grape GT double transformant and the parental line that the Grape GT was introduced into.

| Transgenic Plant | Total pHBA (% of DW] | pHBA Glucose Ester [% of Total pHBA Glucose Conjugates] |
|---|---|---|
| CPL Controls (n = 4) | 0.68 ± 0.25 | 43.5 ± 4.5 |
| 25 | 1.512 | 60 |
| 6 | 1.579 | 72 |
| 2 | 2.462 | 86 |
| 15 | 1.842 | 87 |
| 3 | 2.572 | 90 |
| 10 | 3.149 | 95 |
| 46 | 2.843 | 96 |
| 34 | 3.491 | 96 |
| 52 | 3.571 | 97 |
| 21 | 4.308 | 98 |
| 53 | 3.870 | 98 |
| 47 | 3.863 | 98 |
| 11 | 4.101 | 99 |
| 39 | 4.187 | 99 | pHBA levels in the double transformants continued to rise as the plants matured. Indeed, this phenomenon is observed with CPL-expressing tobacco plants, and the increase with age can be quite dramatic, especially in leaf tissue. In light of the combined results of Tables 5–7, Applicants focused on double transformant line 39. In all of the earlier measurements, this plant consistently exhibited very high leaf levels of pHBA, and accumulated virtually all of the compound as the ester glucoside. As shown in FIG. 3, there was a significant increase in the pHBA leaf content of double transformant line 39 during the course of development. When this plant was fully mature, it constituted nearly 10% of dry weight. Thus, simply by introducing the Grape GT into CPL-expressing tobacco plants, Applicants were able to exceed the previously established threshold level of pHBA accumulation in leaf tissue (4.6% DW) by more than a factor of two.

FIG. 3 also shows the developmental time course for pHBA accumulation in leaf tissue for CPL line 34. As already indicated, the latter is the parental line that the Grape GT was introduced into. Even when this plant was fully mature, the maximum leaf content of pHBA was only ~3.7% DW, which is almost 3 times lower than the value obtained with the double transformant. Additionally, the ratio of ester glucoside to total pHBA glucose conjugates in double transformant line 39 was about 3-fold higher than CPL line 34 at all stages of development (FIG. 3).

Leaf samples were collected from double transformant line 39 and CPL line 34 at various stages of development as indicated. The leaf tissue was extracted with methanol and analyzed for glucose conjugates using HPLC. "pHBA (% DW)" represents the total amount of pHBA that was present in the two glucose conjugates, after correcting for the associated glucose moiety (i.e., the sum of the phenolic glucoside and ester glucoside multiplied by 0.46, as described in Example 10). The number above each time point in FIG. 3 is the percentage of ester glucoside to total pHBA glucose conjugates.

In contrast to leaf levels of pHBA, CPL enzyme activity in leaf tissue did not increase as double transformant line 39 continued to grow (Table 8). Indeed, if anything, there was a slight decrease in CPL-specific activity (~25%) in the leaf extract prepared from the 119-day-old plant compared to the 34-day-old plant. The same trend was also observed with the CPL control plant. However, at all stages of development, double transformant line 39 and the CPL control plant had virtually identical amounts of CPL enzyme activity (i.e., the values differed by less 15% at all time points) (Table 8). In addition to confirming the results that were obtained with the 34-day-old plants described above, the more detailed study in Table 8 provides further proof that the elevated leaf levels of pHBA in the double transformants did not result from higher levels of CPL gene expression.

Table 8 shows the developmental time course for CPL enzyme activity in leaf tissue. Leaf extracts were prepared from double transformant line 39 and a CPL control plant at various stages of development. CPL enzyme activities were determined at room temperature using the spectrophotometric assay described in Example 10. Each assay was run in duplicate or triplicate and the average values are shown; variation between replicates was typically <10%. CPL enzyme activity is expressed as pKats per mg of total leaf extract protein.

TABLE 8

| Age of Plants (d in soil) | CPL Control Plant (pkats/mg) | Double transformant #39 (pkats/mg) |
|---|---|---|
| 34 | 210 | 187 |
| 56 | 153 | 177 |
| 96 | 140 | 145 |
| 119 | 137 | 142 |

Although double transformant line 39 and the CPL control plant had essentially the same amount of CPL enzyme activity as measured in leaf extracts (Table 8), this doesn't necessarily reflect the situation in vivo. CPL enzyme assays are conducted under optimal conditions, and measure initial velocities in the presence of excess substrate and absence of products. Thus, the initial rate of product formation in the in vitro assay is strictly proportional to the amount of enzyme that is added to the cuvette. Consequently, if two plants had identical levels of CPL gene expression, leaf extracts prepared from these plants would theoretically yield the same initial velocity in the in vitro assay. However, a number of researchers have shown that CPL is highly susceptible to product inhibition by pHBA (Bechthold et al., *Archives of Biochemistry and Biophysics* 288(1):39–47 (1991); Holden et al., *Biochimica et Biophysica Acta* 1594:160–167 (2002)). Applicants confirmed these observations. The inhibitory constant (Ki) for pHBA is only ~2 μM, which is 10-fold lower than the Km for chorismate.

Based on the above considerations and estimated concentration of non-glucosylated pHBA ("free pHBA") in CPL-expressing tobacco plants, it seems very likely that CPL is largely product-inhibited in vivo, even though most of the pHBA is converted to glucose conjugates by endogenous plant UDP-glucosyltransferases. If this scenario is correct, the most logical explanation for the higher levels of pHBA observed in the double transformants is relief of product inhibition. When the Grape GT is expressed at very high levels, CPL-generated pHBA is glucosylated at a faster rate, and the steady-state level of free pHBA is lower. With less product inhibition, the catalytic efficiency of CPL is increased, and the same amount of enzyme is able to convert more chorismate to pHBA in the same amount of time.

Example 11

Expression of the Grape GT in CPL-Expressing, pHBA-Overproducing *Arabidopsis* Plants Generation of pHBA-Overproducing *Arabidopsis* Plants The artificial fusion protein, TP-CPL, was introduced into *Arabidopsis* and pHBA glucoside levels were determined. The binary construct described in Example 9, TP-CPL-pZBL1, was transformed into *Agrobacterium tumefaciens* strain C58 C1 Rif (also known as strain GV3101), carrying the disarmed Ti (virulence) plasmid pMP90 (Koncz et al., *Mol. Gen. Genet.* 204:383–396 (1986)) by electroporation, using available protocols (Meyer et al., *Science* 264:1452–1455 (1994)). The MP90 strain carrying the binary vector with the CPL expression construct was used to transform wild type *Arabidopsis thaliana* plants of the ecotype Columbia, using a published protocol of the vacuum infiltration technique (Clough et al., *Plant J.* 16(6):735–43 (1998)). Transgenic seedlings were identified under sterile conditions on standard plant growth media using kanamycin (50 μg/mL) for selection. Kanamycin resistant seedlings were transferred to soil and cultivated under a 12-h light/12-h dark photoperiod at 100 E $m^{-2}s^{-1}$ at 18° C. (dark) and 21 C. (light) in a soil/perlite mixture. Through this procedure, a population of 301 primary transformants derived from independent transformation events was generated. Six weeks after transfer to soil, the transgenic *Arabidopsis* plants were analyzed for pHBA glucosides using reverse phase HPLC as described below.

Fresh cut leaf material was homogenized in 50% MeOH (5 μL per mg wet weight), and the resulting extracts were clarified by low-speed centrifugation. An aliquot of the leaf extract was then applied to a Nova-Pak C18 column (60 angstrom pore size, 4 μm particle size) using a gradient of acetonitrile (6%–48%) that contained 1.5% phosphoric acid. The pHBA phenolic and ester glucosides were detected by UV absorption at 254 nm, and quantitated using extinction coefficients that were obtained from authentic chemical standards. Of the 272 transgenic Arabidopsis plants that were analyzed, 239 (or ~88%) contained detectable levels of the pHBA phenolic glucoside and pHBA glucose ester, both present in about equal amounts. The mean leaf content of pHBA glucose conjugates for the entire population of transgenic arabidopsis plants was 3.35%±0.13% of the total dry weight.

Based on the results of this survey, one of the primary transformants that accumulated large amounts of pHBA was selected for further manipulation. The pHBA glucoside leaf content of this plant (line 41) was 7.5% DW, which is equivalent to 3.42% free pHBA. Line 41 was self-crossed and T2 seeds were germinated on media containing kanamycin. The segregation pattern for kanamycin resistance of the T2 plants was ~3:1 (resistant to sensitive), indicating that the original primary transformant (T1 plant) had resulted from a single integration event. T3 seeds were collected from T2 progeny. T3 seed batches derived from T2 plants that were homozygous for the T-DNA insertion were identified. These T3 seed batches no longer segregated kanamycin-sensitive progeny when germinated on media containing kanamycin. All the resulting progeny from these T3 seed batches were therefore also homozygous for CPL. As described below, one of the T3 seed batches that only gave rise to kanamycin-resistant progeny was used for trait-stacking experiments with the Grape GT.

Introduction of the Grape GT into pHBA-overproducing Arabidopsis Plants.

The same Grape GT expression construct that was used for tobacco transformation in Example 10, pBE856 (SCP1-Grape GT), was introduced into *Agrobacterium tumefaciens* strain C58 C1 Rif, carrying the disarmed Ti (virulence) plasmid pMP90 (Koncz et al., *Mol. Gen. Genet.* 204:383–396 (1986)). Briefly, 1 ug plasmid DNA was mixed with 100 uL of electro-competent cells on ice. The cell suspension was transferred to a 100-μl electroporation cuvette (1 mm gap width) and electroporated using a BIO-RAD electroporator set to 1 kV, 400 Ω and 25 μF. The cells were transferred to 1 mL LB medium, incubated for 2 h at 30° C., and were then plated onto LB medium containing 50 ug $mL^{-1}$ kanamycin and 10 ug $mL^{-1}$ rifampicin. The plates were incubated at 30° C. for 60 h. Recombinant agrobacterium cultures (500 mL LB, 50 ug $mL^{-1}$ kanamycin and 10 ug $mL^{-1}$ rifampicin) were inoculated from single colonies of transformed agrobacterium cells and grown at 30° C. for 60 h. Cells were harvested by centrifugation (5000×g, 10 min) and resuspended in 1 L of 5% (W/V) sucrose containing 0.05% (v/v) Silwet. *Arabidopsis* plants homozygous for TP-CPL, which were obtained from one of the line 41 T3 seed batches that only gave rise to kanamycin-resistant progeny as described above, were grown in soil at a density of 30 plants per 100 $cm^2$ pot in metromix 360 soil mixture for 4 weeks (22° C., 16 h light/8 h dark, 100 μE $m^{-2}s^{-1}$). The plants were repeatedly dipped into the agrobacterium suspension described above and kept in a dark, high humidity environment for 24 h. The plants were then grown for 3–4 weeks under the standard growth conditions described above.

Following this procedure, the plant material was harvested and dried for one week at ambient temperatures in paper bags. The seeds were then harvested using a 0.425 mm mesh brass sieve. One and a half grams of cleaned arabidopsis seed, corresponding to about 75000 seed were sterilized by washes in 45 mL of 80% ethanol, 0.01% Triton X-100, followed by 45 mL of 30% (V/V) household bleach in water, 0.01% Triton X-100 and finally by repeated rinsing in sterile water. Aliquots of ~7500 seed were transferred to 13 mm Petri dishes containing sterile plant growth medium, which consisted of 0.5×MS salts, 1.5% (w/v) sucrose, 0.05 MES/KOH, pH 5.8, 200 ug mL$^{-1}$ timentin, and 10 ug mL$^{-1}$ phosphinotricine, solidified with agar (10 gl$^{-1}$). Homogeneous dispersion of the seed on the medium was facilitated by mixing the aqueous seed suspension with a equal volume of melted plant growth medium. The plates were incubated under standard growth conditions for 10 d. Phosphinotricine-resistant seedlings were transferred to plant growth medium without phosphinotricine and grown for fourteen days before transfer to soil.

Characterization of the Arabidopsis CPL/Grape GT Double Transformants

Approximately 4 weeks after transfer to soil, leaf samples were collected from 45 of the primary transformants and methanol extracts were prepared for HPLC analysis to determine the content of pHBA glucosides. The goal was to identify the plants that had converted the majority of their pHBA to the glucose ester. Based on the results of this survey, a subset of the plants was tested for UDP-glucosyltransferase activity with pHBA as a substrate, using leaf extracts and the spectrophotometric assay that is described in Example 10. As already indicated, this assay only detects the formation of the pHBA ester glucoside, and provides a convenient way to identify the plants that express the highest levels of the Grape GT. Based on the combined results of these two analyses, one of the primary transformants (Line 1) was selected for further manipulation. This plant had at least five times more pHBA ester glucoside-forming activity in leaf extracts than the CPL control plants, and the pHBA ester glucoside was the predominant product in leaf tissue (92% of the total pHBA conjugates).

To determine the stability of the Grape GT transgene and characterize the phenotype in greater detail, Line 1 was allowed to self-cross and seeds were collected. The seeds were germinated in soil and the resulting plants were grown at 50% relative humidity, using a 14 h light (20° C.)/10 h (18° C.) dark cycle; the light intensity was ~80 µE m$^{-2}$s$^{-1}$. To serve as a control for this experiment, seeds from line 41 (the CPL-expressing line that the Grape GT was introduced into) were planted at the same time and the resulting plants were grown under identical conditions.

As described in more detail below, the plants were analyzed after 5 weeks of growth, and the results of this experiment are summarized in Table 9. All measurements were conducted with leaf tissue. Line 1 is genetically identical to Line 41, with the exception of the Grape GT. Both lines are homozygous for CPL and the integration site for the transgene is the same.

As shown in Table 9, the arabidopsis CPL/Grape GT double transformants (line 1) had a much higher percentage of pHBA ester glucoside than the CPL control plants (line 41). The double transformants also had eleven times more pHBA ester glucoside forming activity than Line 41. The most important observation, however, is the stimulatory effect of the Grape GT on pHBA accumulation. Thus, the total leaf content of pHBA in line 1 was more than 2.5-fold greater than the CPL control plants (Table 9). Furthermore, this is not because CPL gene expression was higher in the double transformants, since both sets of plants yielded similar amounts of CPL enzyme activity in leaf extracts (Table 9). Similar to the situation in tobacco (Example 10), the most likely explanation for the higher leaf levels of pHBA in the arabidopsis double transformants relates to product inhibition of CPL. In the presence of the Grape GT, the steady-state level of free pHBA is probably lower and CPL is less inhibited. Consequently, the double transformants convert more chorismate-to pHBA in the same amount of time than the CPL control plants. In other words, CPL is a more efficient catalyst in the presence of the Grape GT, since the former is subject to less product inhibition.

Table 9 shows characterization of transgenic arabidopsis plants that express CPL and the Grape GT (Line 1). Line 41 expresses CPL only, and is the parental line into which the Grape GT was introduced. Both sets of plants were 5 weeks old at the time of analysis. All measurements were conducted with leaf tissue. CPL enzyme activity and pHBA ester glucoside-forming activity ("GT Activity") were measured as described in Example 10. Three different siblings from both lines were assayed for each parameter, and the values in the table represent the mean±SE.

TABLE 9

| Plant | CPL Activity (pkats/mg) | GT Activity (pkats/mg) | Total pHBA (% DW) | Glucose Ester (% total glucose conjugates) |
|---|---|---|---|---|
| Line 41 | 172 ± 22 | 14.3 ± 1.0 | 1.03 ± 0.03 | 71.0 ± 1.0 |
| Line 1 | 154 ± 16 | 159 ± 18 | 2.60 ± 0.51 | 95.0 ± 1.5 |

Taken together, these experiments provide a compelling demonstration of the in vivo utility of the Grape GT in pHBA-overproducing plants. The virtually identical results obtained in tobacco and arabidopsis strongly suggests that this approach would work with many other plant species as well. Finally, the experiments described herein suggest a general trait-stacking strategy that could be used to partition other plant-generated hydroxybenzoic acid derivatives (i.e., gallic acid) or hydroxycinnamic acid derivatives (i.e., pHCA) to their corresponding ester glucosides, using an appropriate UDP-glucosyltransferase. As already indicated, one of the major advantages of having plants that only form the pHBA ester glucoside is that it is very easy to recover free pHBA from this compound compared to the phenolic glucoside. The fact that it is easier to cleave off the associated glucose molecule from the ester glucoside could represent a substantial cost savings in the recovery and purification of free pHBA using a plant-based platform, and this is probably also true for other hydroxybenzoic acid and hydroxycinnamic acid derivatives.

Figure 4A:
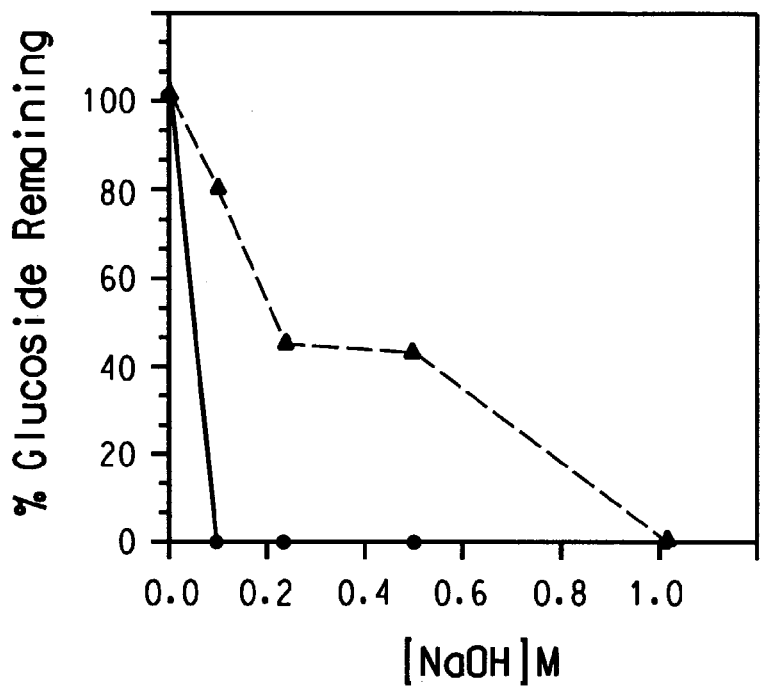
FIGS. 4a and 4b show acid and base hydrolysis of pHBA phenolic glucoside and pHBA ester glucoside.
Figure 4B:
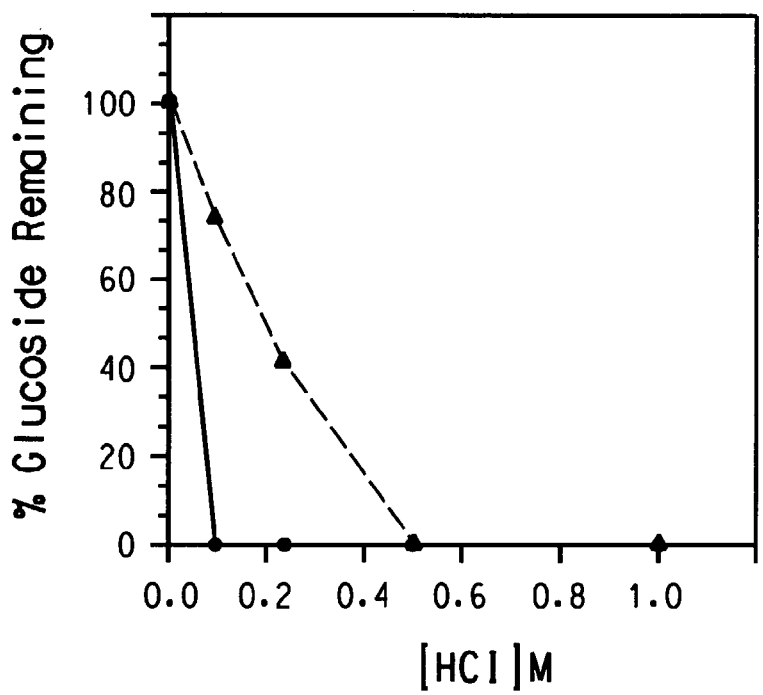

As shown in FIGS. 4a and 4b, the pHBA glucose ester is far more susceptible to acid and base hydrolysis than the pHBA phenolic glucoside. The pHBA phenolic glucoside and pHBA glucose ester were incubated for 48 h at 60° C. with indicated concentrations of NaOH (Panel A) or HCL (Panel B). The initial concentration of both compounds was 0.19 mM and the total reaction volume was 106 mL. Reactions were conducted in tightly sealed polypropylene tubes to prevent evaporative loss. Following acid or base hydrolysis, the samples were analyzed by HPLC for pHBA glucose conjugates and free pHBA, using the same column and gradient that is described in Example 10. Prior to HPLC analysis, the acid hydrolyzed samples were diluted with an equal volume of NaOH that contained a 0.2 mM excess of NaOH relative to the original concentration of HCL. The base hydrolyzed samples were analyzed directly. Chemically synthesized pHBA phenolic and ester glucoside standards and free pHBA were used to calibrate the HPLC runs for retention times, and extinction coefficients for all three compounds were accurately determined under the conditions employed. Peak areas were integrated using the software package provided with the Hewlett Packard Chemstation, and values obtained with known amounts of the chemical standards were used to quantitate compounds of interest in the acid and base hydrolyzed samples. In FIGS. 4a and 4b, filled triangles correspond to the pHBA phenolic glucoside and filled circles correspond to the pHBA glucose ester.

What is claimed is:

1. An isolated nucleic acid molecule encoding a UDP-glucosyltransferase enzyme selected from the group consisting of:
   (a) an isolated nucleic acid molecule encoding the amino acid sequence of SEQ ID NO:18 or SEQ ID NO:22;
   (b) an isolated nucleic acid molecule that hybridizes with (a) under the following stringent hybridization conditions: 0.1×SSC, 0.1% SDS at 65° C., and washed with 2×SSC, 0.1% SDS followed by 0.1×SSC, 0.1% SDS; and
   (c) an isolated nucleic acid molecule that is a full length complement of (a) or (b).

2. An isolated nucleic acid molecule encoding a UDP-glucosyltransferase enzyme having the amino, acid sequence SEQ ID NO:31.

3. An isolated nucleic acid molecule encoding a UDP-glucosyltransferase enzyme having:
   a) at least 95% identity to the amino acid sequence of SEQ ID NO:18 or at least 95% identity to the amino acid sequence of SEQ ID NO:22;
   b) activity to catalyze the production of pHBA ester glucoside from pHBA;
   c) at least a 4.88-fold substrate preference for pHBA over sinapic acid at a 10 mM substrate concentration; and
   d) a turnover number of at least 1.77 sec$^{-1}$ for the conversion of pHBA to pHBA ester glucoside.

4. The isolated nucleic acid molecule of claim 1 or claim 3 selected from the group consisting of SEQ ID NO:17 and SEQ ID NO:21.

5. The isolated nucleic acid molecule of claim 2 having the nucleic acid sequence of SEQ ID NO:30.

6. An isolated nucleic acid molecule comprising
   (a) a nucleotide sequence encoding an UDP-glucosyltransferase enzyme having at least 95% identity over the length of 478 amino acids based on the Smith-Waterman method of alignment when compared to a polypeptide having the sequence of SEQ ID NO:18, or
   (b) a nucleotide sequence comprising the complement of the nucleotide sequence of (a).

7. An isolated nucleic acid molecule comprising
   (a) a nucleotide sequence encoding an UDP-glucosyltransferase enzyme having at least 95% identity over the length of 511 amino acids based on the Smith-Waterman method of alignment when compared to a polypeptide having the sequence of SEQ ID NO:22, or
   (b) a nucleotide sequence comprising the complement of the nucleotide sequence of (a).

8. A chimeric gene comprising the isolated nucleic acid molecule of any one of claims 1–3 operably linked to suitable regulatory sequences.

9. An isolated transformed host cell comprising the chimeric gene of claim 8.

10. The transformed host cell of claim 9 wherein the host cell is
    (a) a microorganism selected from the group consisting of *Escherichia*, *Klebsiella*, *Salmonella*, *Agrobacterium*, *Saccharomyces*, *Pichia*, *Pseudomonas*, and *Bacillus*; or
    (b) a green plant cell selected from the group consisting of eucalyptus (*Eucalyptus grandis*), tobacco (*Nicotiana* spp.), arabidopsis (*Arabidopsis thaliana*) sugarbeet (*Beta* spp.), sugarcane (*Saccharum* spp.), kenaf (*Hibiscus cannabinus* L), castor (*Ricinus* spp.), miscanthus (*Miscanthus* spp.), and Elephant grass (*Pennisetum* spp.).

11. The transformed host cell of claim 10 further comprising one or both nucleic acid fragments selected from the group consisting of:
    a) a nucleic acid fragment for chorismate pyruvate lyase enzyme activity, the nucleic acid fragment encoding a polypeptide having the amino acid sequence of SEQ ID NO:38; and
    b) a nucleic acid fragment for 4-hydroxycinnamoyl-CoA hydratase/lyase enzyme activity, the nucleic acid fragment encoding a polypeptide having the amino acid sequence of SEQ ID NO:46,
each nucleic acid fragment operably linked to suitable regulatory sequences.

* * * * *